US008716319B2

(12) United States Patent  (10) Patent No.: US 8,716,319 B2
Abelman et al.  (45) Date of Patent: May 6, 2014

(54) SUBSTITUTED HETEROCYCLIC COMPOUNDS

(75) Inventors: Matthew Abelman, Mountain View, CA (US); Robert Jiang, Cupertino, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 423 days.

(21) Appl. No.: 12/702,825

(22) Filed: Feb. 9, 2010

(65) Prior Publication Data

US 2010/0197684 A1  Aug. 5, 2010

Related U.S. Application Data

(63) Continuation of application No. 12/167,558, filed on Jul. 3, 2008, now abandoned.

(60) Provisional application No. 60/958,632, filed on Jul. 5, 2007.

(51) Int. Cl.
*A01N 43/40* (2006.01)
*A61K 31/44* (2006.01)
*C07D 213/803* (2006.01)

(52) U.S. Cl.
USPC .......................................... 514/356; 546/321

(58) Field of Classification Search
None
See application file for complete search history.

(56) References Cited

U.S. PATENT DOCUMENTS

| | | | |
|---|---|---|---|
| 3,845,770 A | 11/1974 | Theeuwes et al. | |
| 3,867,393 A * | 2/1975 | Meyer et al. | 546/321 |
| 4,326,525 A | 4/1982 | Swanson et al. | |
| 4,532,248 A | 7/1985 | Franckowiak et al. | |
| 4,596,873 A | 6/1986 | Sulkowski et al. | |
| 4,874,760 A | 10/1989 | Yamada et al. | |
| 4,902,514 A | 2/1990 | Barclay et al. | |
| 4,918,074 A | 4/1990 | Tsuda et al. | |
| 4,992,445 A | 2/1991 | Lawter et al. | |
| 5,001,139 A | 3/1991 | Lawter et al. | |
| 5,023,252 A | 6/1991 | Hseih | |
| 5,616,345 A | 4/1997 | Geoghegan et al. | |
| 5,760,073 A | 6/1998 | Urbahns et al. | |
| 6,303,607 B1 | 10/2001 | Wolff et al. | |
| 6,369,062 B1 | 4/2002 | Wolff et al. | |
| 6,451,355 B1 | 9/2002 | Reisner | |
| 6,479,496 B1 | 11/2002 | Wolff | |
| 6,503,911 B2 | 1/2003 | Wolff et al. | |
| 6,525,057 B2 | 2/2003 | Wolff et al. | |
| 6,528,511 B2 | 3/2003 | Wolff et al. | |
| 6,562,826 B1 | 5/2003 | Wolff | |
| 6,617,328 B2 | 9/2003 | Wolff et al. | |
| 6,620,814 B2 | 9/2003 | Wolff | |
| 6,852,724 B2 | 2/2005 | Wolff | |
| 6,864,258 B2 | 3/2005 | Wolff | |
| 2003/0022890 A1 | 1/2003 | Atwal et al. | |
| 2004/0063717 A1 | 4/2004 | Wolff et al. | |
| 2006/0177502 A1 | 8/2006 | Sastry et al. | |
| 2008/0009503 A1 | 1/2008 | Wolff et al. | |
| 2008/0109040 A1 | 5/2008 | Belardinelli | |
| 2008/0153840 A1 | 6/2008 | Belardinelli | |
| 2008/0193530 A1 | 8/2008 | Wolff et al. | |
| 2008/0214555 A1 | 9/2008 | Jerling | |
| 2008/0248112 A1 | 10/2008 | Wolff et al. | |
| 2008/0255031 A1 | 10/2008 | Dhalla et al. | |
| 2008/0299195 A1 | 12/2008 | Wolff et al. | |
| 2009/0012103 A1 | 1/2009 | Abelman | |
| 2009/0176772 A1 | 7/2009 | Blackburn | |

FOREIGN PATENT DOCUMENTS

| | | |
|---|---|---|
| EP | 0111453 | 6/1984 |
| EP | 0111455 | 6/1984 |
| EP | 0163240 A2 | 12/1985 |
| WO | WO-8504172 A1 | 9/1985 |
| WO | WO-2005/025507 | 3/2005 |
| WO | WO-2006/122156 | 11/2006 |
| WO | WO-2007/051062 A | 5/2007 |
| WO | WO-2009/006580 A1 | 1/2009 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Vippagunta et. al. Advanced Drug Delivery Reviews 48 (2001) 3-26.*
Chawla et. al. Current Research & Information on Pharmaceutical Science, 2004, 5(1), p. 9-12.*
Newman et. al.; Drug Discovery Today; 2003, 8(19) p. 898-905.*
Rabe, et. al., Justus Liebigs Annalen der Chemie (1909), 360, 265-88.*
Hinkel, et. al., Journal of the Chemical Society, Transactions (1920), 117, 137-40.*
Antaki, H., Journal of the Chemical Society (1963), (Oct.), 4877-9.*
International Preliminary Report on Patentability for PCT/US2009/030486, International Filing Date Jan. 8, 2009, dated Jan. 5, 2011.
Banker, G.S. et al. (1996), *Modern Pharmaceutics*, 3rd Edition, p. 596.

(Continued)

*Primary Examiner* — Jeffrey H Murray
(74) *Attorney, Agent, or Firm* — Francis O. Ginah; J. Elin Hartrum

(57) ABSTRACT

The present invention relates to novel heterocyclic compounds and to their use in the treatment of various disease states, including cardiovascular diseases and diabetes. In particular embodiments, the structure of the compounds is given by Formula (I):

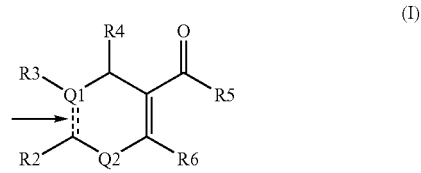

(I)

wherein Q1, Q2, R2, R3, R4, R5, and R6 are as described herein.
The invention also relates to methods for the preparation of the compounds, and to pharmaceutical compositions containing such compounds.

4 Claims, 3 Drawing Sheets

(56) References Cited

OTHER PUBLICATIONS

Chawla, G. et al. (2004), "Challenges in Polymorphism of Pharmaceuticals", *Current Research & Information on Pharmaceutical Science*, vol. 5(1), p. 9.

Dorwald, F.Z. (1005), *Side Reactions in Organic Synthesis*, Wiley: VCH, Weinheim, p. IX of Preface.

Drizin, I. et al. (2002) "Structure-Activity Studies for a Novel Series of Tricyclic Dihydropyrimidines as K-ATP Channel Operators (KCOS)" *Bioorganic & Medicinal Chemistry Letters*, 12: 1481-1484.

International Search Report for PCT/US2008/069173, International Filing Date Jul. 3, 2008, mailing date of Oct. 30, 2008.

International Search Report for PCT/US2009/030486, International Filing Date Jan. 8, 2009, mailing date Apr. 28, 2009.

Newman, A.W. et al. (2003), "Solid-state analysis of the active pharmaceutical ingredient in drug products", *Drug Discovery Today*, vol. 8(19), p. 898.

Office Action for U.S. Appl. No. 12/167,558, mailed Apr. 2, 2009.

Office Action for U.S. Appl. No. 12/167,558, mailed Aug. 11, 2009.

Office Action for U.S. Appl. No. 12/350,841, mailed May 28, 2009.

Pirisino, R. et al. (1979), "Pharmacological activity of some pyrazolo[1,5-a] pyrimidines", *Farmaco, Edizione Scientifica*, vol. 34(9), pp. 802-807.

Response to Office Action mailed Apr. 2, 2009, for U.S. Appl. No. 12/167,568 dated May 29, 2009.

Vippagunta, S.R. et al. (2001) "Crystalline Solids", *Advanced Drug Delivery Reviews*, vol. 48, pp. 3-26.

Wolff, M.E. (1995) *Burger's Medicinal Chemistry and Drug Discovery*, 5th Edition, vol. 1, pp. 975-977.

\* cited by examiner

SUBSTITUTED HETEROCYCLIC COMPOUNDS

This application is a continuation of U.S. patent application Ser. No. 12/167,558, filed Jul. 3, 2008, which claims priority to U.S. Provisional Patent Application Ser. No. 60/958,632, filed Jul. 5, 2007, the entirety of which is herein incorporated by reference.

FIELD

The present invention relates to novel heterocyclic compounds and to their use in the treatment of various disease states, including cardiovascular diseases and diabetes. The invention also relates to methods for their preparation, and to pharmaceutical compositions containing such compounds.

SUMMARY

Accordingly, in typical embodiments the present invention provides novel substituted heterocyclic compounds that function as late sodium channel blockers. In typical embodiments the invention relates to compounds of Formula (I):

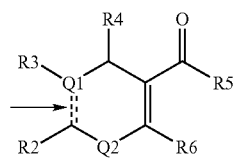

wherein:
Q1 is carbon or nitrogen,
Q2 is oxygen or R1-N<, where R1 is hydrogen or optionally substituted lower alkyl;
the double dotted line indicated by the arrow is a single bond or a double bond;
R2 is hydrogen, optionally substituted lower alkyl, optionally substituted alkyl, optionally substituted alkenyl, optionally substituted alkynyl, optionally substituted cycloalkyl, optionally substituted heterocyclyl, optionally substituted aryl, optionally substituted heteroaryl, or —NR21R22, where R21 and R22 are independently hydrogen, lower alkyl, optionally substituted alkyl, optionally substituted alkenyl, optionally substituted alkynyl;
R3 is hydrogen, lower alkyl, optionally substituted alkyl, optionally substituted alkenyl, optionally substituted alkynyl, optionally substituted cycloalkyl, optionally substituted heterocyclyl, optionally substituted aryl, optionally substituted heteroaryl, cyano, —C(O)—R31, or —C(O)—O—R31, where R31 is hydrogen, lower alkyl, optionally substituted alkyl, optionally substituted alkenyl, optionally substituted alkynyl, optionally substituted cycloalkyl, optionally substituted heterocyclyl, optionally substituted aryl, or optionally substituted heteroaryl;
or R2 and R3 taken together with Q1 and the carbon to which R2 is attached form a 5 or 6 membered heterocyclyl, heteroaryl, cycloalkyl, or a saturated or unsaturated carbocyclic moiety, all of which are optionally substituted, for example by halo, optionally substituted lower alkyl, optionally substituted alkyl, optionally substituted alkenyl, optionally substituted alkynyl, optionally substituted alkoxy, optionally substituted cycloalkyl, optionally substituted aryl;
R4 is optionally substituted alkyl, optionally substituted alkenyl, optionally substituted alkynyl, optionally substituted cycloalkyl, optionally substituted heterocyclyl, optionally substituted aryl, or optionally substituted heteroaryl, provided that any substituent of R4 may itself be optionally substituted, for example by halo, optionally substituted lower alkyl, optionally substituted alkyl, optionally substituted alkenyl, optionally substituted alkynyl, optionally substituted alkoxy, optionally substituted cycloalkyl, optionally substituted aryl;
R5 is optionally substituted alkyl, optionally substituted alkenyl, optionally substituted alkynyl, optionally substituted cycloalkyl, optionally substituted heterocyclyl, optionally substituted aryl, optionally substituted heteroaryl, —O—R51, or —NR52R53, where R51 is optionally substituted alkyl, optionally substituted alkenyl, optionally substituted alkynyl, optionally substituted cycloalkyl, optionally substituted heterocyclyl, optionally substituted aryl, optionally substituted heteroaryl, where R52 and R53 are each independently hydrogen, lower alkyl, optionally substituted alkyl, optionally substituted alkenyl, optionally substituted alkynyl, optionally substituted cycloalkyl, optionally substituted heterocyclyl, optionally substituted aryl, optionally substituted heteroaryl, or R52 and R53 taken together with the nitrogen to which they are both directly attached form 5 or 6 membered heterocyclyl or heteroaryl moiety, which is optionally substituted by halo, optionally substituted alkyl, optionally substituted alkenyl, optionally substituted alkynyl, optionally substituted alkoxy, optionally substituted cycloalkyl, optionally substituted heterocyclyl, optionally substituted aryl, or optionally substituted heteroaryl;
R6 is hydrogen, lower alkyl, optionally substituted alkyl, optionally substituted alkenyl, optionally substituted alkynyl, optionally substituted cycloalkyl, optionally substituted heterocyclyl, optionally substituted aryl, or optionally substituted heteroaryl, —NR61R62, where R61 and R62 are independently hydrogen, lower alkyl, optionally substituted alkyl, optionally substituted alkenyl, optionally substituted alkynyl;
or R5 and R6 taken together with the carbons to which R5 and R6 are directly attached and the carbon directly attached to both of the carbons to which R5 and R6 are directly attached form a 5 or 6 membered heterocyclyl, heteroaryl, cycloalkyl, or a saturated or unsaturated carbocyclic moiety, all of which are optionally substituted by halo, optionally substituted lower alkyl, optionally substituted alkyl, optionally substituted alkenyl, optionally substituted alkynyl, optionally substituted alkoxy, optionally substituted cycloalkyl, optionally substituted aryl, optionally substituted heterocyclyl, optionally substituted aryl, or optionally substituted heteroaryl.

In certain embodiments the invention provides pharmaceutical formulations comprising a therapeutically effective amount of a compound of Formula (I) and at least one pharmaceutically acceptable excipient.

Some embodiments provide a method of using the compounds of Formula (I) in the treatment of a disease or condition in a mammal that is amenable to treatment by a late sodium channel blocker. The compounds of the invention and their therapeutically acceptable salts, esters, tautomeric forms are potentially of use as medicaments for the treatment of certain diseases, such as, cardiovascular diseases such as atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease, and intermittent claudication. Such diseases may also include diabetes, and conditions related to diabetes, e.g. diabetic peripheral neuropathy. Such diseases may also include conditions affecting the neuromuscular system resulting in pain, seizures, or paralysis.

BRIEF DESCRIPTION OF THE DRAWINGS

These and other features of the invention will be understood from the description of representative embodiments of the method herein and the disclosure of illustrative materials for carrying out the method, taken together with the Figures, wherein.

DETAILED DESCRIPTION

Figure 1:
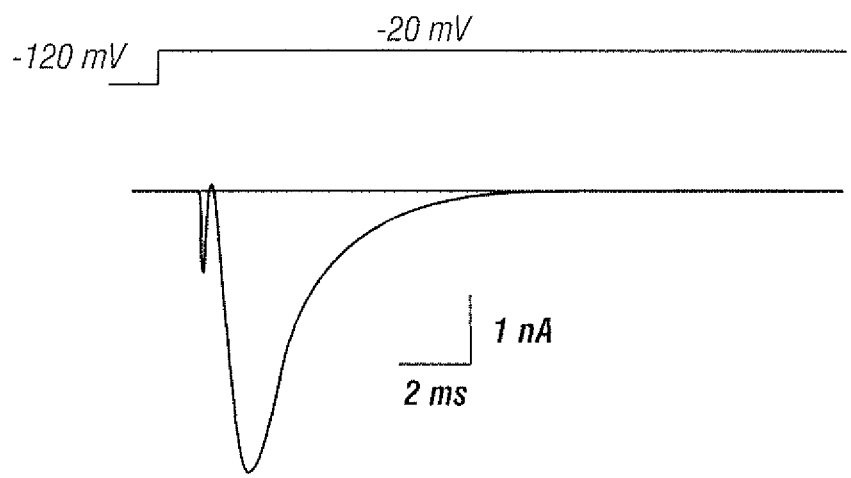
FIG. 1 shows a typical response due to activation of $Na_v 1.5$ sodium channel in a sodium current assay.

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having 1, 2, 3, 4 or 5 substituents, (typically 1, 2, or 3 substituents) selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or
2) an alkyl group as defined above that is interrupted by 1-10 atoms (e.g. 1, 2, 3, 4, or 5 atoms) independently chosen from oxygen, sulfur and NRa—, where Ra is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or
3) an alkyl group as defined above that has both 1, 2, 3, 4 or 5 substituents as defined above and is also interrupted by 1-10 atoms (e.g. 1, 2, 3, 4, or 5 atoms) as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (typically 1, 2, or 3 substituents), as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, typically having from 1 to 20 carbon atoms (e.g. 1-10 carbon atoms, or 1, 2, 3, 4, 5 or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "lower alkylene" refers to a diradical of a branched or unbranched saturated hydrocarbon chain, typically having 1, 2, 3, 4, 5, or 6 carbon atoms.

The term "substituted alkylene" refers to:
(1) an alkylene group as defined above having 1, 2, 3, 4, or 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, acyloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or
(2) an alkylene group as defined above that is interrupted by 1-10 groups (e.g. 1, 2, 3, 4, or 5 groups) independently chosen from —O—, —S—, sulfonyl, —C(O)—, —C(O)O—, —C(O)N—, and —NRa—, where Ra is chosen from hydrogen, optionally substituted alkyl, cycloalkyl, cycloalkenyl, aryl, heteroaryl and heterocyclyl; or
(3) an alkylene group as defined above that has both 1, 2, 3, 4 or 5 substituents as defined above and is also interrupted by 1-10 groups as defined above. Examples of substituted alkylenes are chloromethylene (—CH(Cl)—), aminoethylene (—$CH(NH_2)CH_2$—), methylaminoethylene (—$CH(NHMe)CH_2$—), 2-carboxypropylene isomers (—$CH_2CH(CO_2H)CH_2$—), ethoxyethyl (—$CH_2CH_2O$—$CH_2CH_2$—), ethylmethylaminoethyl (—CH$_2$CH$_2$—N(CH$_3$)—CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl as defined above. This term is exemplified by groups such as methoxy, ethoxy, n-propoxy, iso-propoxy, n-butoxy, iso-butoxy, t-butoxy, n-hexyloxy, and the like.

The term "alkylthio" refers to the group R—S—, where R is as defined for alkoxy.

The term "alkenyl" refers to a monoradical of a branched or unbranched unsaturated hydrocarbon group typically having from 2 to 20 carbon atoms (more typically from 2 to 10 carbon atoms, e.g. 2 to 6 carbon atoms) and having from 1 to 6 carbon-carbon double bonds, e.g. 1, 2, or 3 carbon-carbon double bonds. Typical alkenyl groups include ethenyl (or vinyl, i.e. —CH═CH$_2$), 1-propylene (or allyl, —CH$_2$CH═CH$_2$), isopropylene (—C(CH$_3$)═CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, typically having from 2 to 20 carbon atoms (more typically from 2 to 10 carbon atoms, e.g. 2 to 6 carbon atoms) and having from 1 to 6 carbon-carbon triple bonds e.g. 1, 2, or 3 carbon-carbon triple bonds. Typical alkynyl groups include ethynyl (—C≡CH), propargyl (or propynyl, —C≡CCH3), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, CF$_3$, amino, substituted amino, cyano, or —S(O)$_n$Ra, in which Ra is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl, fluorenyl, and anthryl). Typical aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, acyloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —$NH_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl are as defined herein, and may be optionally further substituted by alkyl, alkenyl, alkynyl, alkoxy, halogen, $CF_3$, amino, substituted amino, cyano, or —$S(O)_nR$, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. The term "substituted cycloalkyl" also includes cycloalkyl groups wherein one or more of the annular carbon atoms of the cycloalkyl group is a carbonyl group (i.e. an oxygen atom is oxo to the ring). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a group comprising 1 to 15 carbon atoms and 1 to 4 heteroatoms selected from oxygen, nitrogen, and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, 1,2,3,4-tetrahydronaphthalene.

Unless otherwise constrained by the definition for the heteroaryl substituent, such heteroaryl groups can be optionally substituted with 1 to 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2. Heterocyclic groups can have a single ring or multiple condensed rings.

Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

A compound of a given Formula (e.g. the "compound of Formula (I)") is intended to encompass the compounds of the invention as disclosed, and the pharmaceutically acceptable salts, pharmaceutically acceptable esters, hydrates, polymorphs, and prodrugs of such compounds. Additionally, the compounds of the invention may possess one or more asymmetric centers, and can be produced as a racemic mixture or as individual enantiomers or diastereoisomers. The number of stereoisomers present in any given compound of a given Formula depends upon the number of asymmetric centers present (there are 2n stereoisomers possible where n is the number of asymmetric centers). The individual stereoisomers may be obtained by resolving a racemic or non-racemic mixture of an intermediate at some appropriate stage of the synthesis, or by resolution of the compound by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

In many cases, the compounds of this invention are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Coronary diseases" or "cardiovascular diseases" refer to diseases of the cardiovasculature arising from any one or more than one of for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes, and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs, or calves when walking, climbing stairs, or exercising. The pain is called intermittent claudication. When listing the symptom intermittent claudication, it is intended to include both PAD and PVD Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia, and the ventricular tachycardias (VTs), including idiopathic ventricular tachycardia, ventricular fibrillation, pre-excitation syndrome, and Torsade de Pointes (TdP), Nomenclature Names of compounds of the present invention are provided using ChemDraw Ultra v. 10.0 (CambridgeSoft, Cambridge, Mass.). Other compounds or radicals may be named with common names, or systematic or non-systematic names. The naming and numbering of the compounds of the invention is illustrated with a representative compound of Formula I (PT-148)

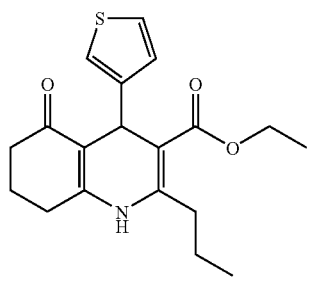

which is named ethyl 5-oxo-2-propyl-4-(thiophen-3-yl)-1, 4,5,6,7,8-hexahydroquinoline-3-carboxylate.

Accordingly, in typical embodiments the present invention provides novel substituted heterocyclic compounds that function as late sodium channel blockers. In typical embodiments the invention relates to compounds of Formula (I):

(I)

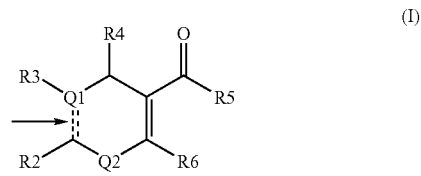

wherein:
Q1 is carbon or nitrogen,
Q2 is oxygen or R1-N<, where R1 is hydrogen or optionally substituted lower alkyl;
the double dotted line indicated by the arrow is a single bond or a double bond;
R2 is hydrogen, optionally substituted lower alkyl, optionally substituted alkyl, optionally substituted alkenyl, optionally substituted alkynyl, optionally substituted cycloalkyl, optionally substituted heterocyclyl, optionally substituted aryl, optionally substituted heteroaryl, or —NR21R22, where R21 and R22 are independently hydrogen, lower alkyl, optionally substituted alkyl, optionally substituted alkenyl, optionally substituted alkynyl;
R3 is hydrogen, lower alkyl, optionally substituted alkyl, optionally substituted alkenyl, optionally substituted alkynyl, optionally substituted cycloalkyl, optionally substituted heterocyclyl, optionally substituted aryl, optionally substituted heteroaryl, cyano, —C(O)—R31, or —C(O)—O—R31, where R31 is hydrogen, lower alkyl, optionally substituted alkyl, optionally substituted alkenyl, optionally substituted alkynyl, optionally substituted cycloalkyl, optionally substituted heterocyclyl, optionally substituted aryl, or optionally substituted heteroaryl;
or R2 and R3 taken together with Q1 and the carbon to which R2 is attached form a 5 or 6 membered heterocyclyl, heteroaryl, cycloalkyl, or a saturated or unsaturated carbocyclic moiety, all of which are optionally substituted, for example by halo, optionally substituted lower alkyl, optionally substituted alkyl, optionally substituted alkenyl, optionally substituted alkynyl, optionally substituted alkoxy, optionally substituted cycloalkyl, optionally substituted aryl;
R4 is optionally substituted alkyl, optionally substituted alkenyl, optionally substituted alkynyl, optionally substituted cycloalkyl, optionally substituted heterocyclyl, optionally substituted aryl, or optionally substituted heteroaryl, provided that any substituent of R4 may itself be optionally substituted, for example by halo, optionally substituted lower alkyl, optionally substituted alkyl, optionally substituted alkenyl, optionally substituted alkynyl, optionally substituted alkoxy, optionally substituted cycloalkyl, optionally substituted aryl;
R5 is optionally substituted alkyl, optionally substituted alkenyl, optionally substituted alkynyl, optionally substituted cycloalkyl, optionally substituted heterocyclyl, optionally substituted aryl, optionally substituted heteroaryl, —O—R51, or —NR52R53, where R51 is optionally substituted alkyl, optionally substituted alkenyl, optionally substituted alkynyl, optionally substituted cycloalkyl, optionally substituted heterocyclyl, optionally substituted aryl, optionally substituted heteroaryl, where R52 and R53 are each independently hydrogen, lower alkyl, optionally substituted alkyl, optionally substituted alkenyl, optionally substituted alkynyl, optionally substituted cycloalkyl, optionally substituted heterocyclyl, optionally substituted aryl, optionally substituted heteroaryl, or R52 and R53 taken together with the nitrogen to which they are both directly attached form 5 or 6 membered heterocyclyl or heteroaryl moiety, which is optionally substituted by halo, optionally substituted alkyl, optionally substituted alkenyl, optionally substituted alkynyl, optionally substituted alkoxy, optionally substituted cycloalkyl, optionally substituted heterocyclyl, optionally substituted aryl, or optionally substituted heteroaryl;

R6 is hydrogen, lower alkyl, optionally substituted alkyl, optionally substituted alkenyl, optionally substituted alkynyl, optionally substituted cycloalkyl, optionally substituted heterocyclyl, optionally substituted aryl, or optionally substituted heteroaryl, —NR61R62, where R61 and R62 are independently hydrogen, lower alkyl, optionally substituted alkyl, optionally substituted alkenyl, optionally substituted alkynyl;

or R5 and R6 taken together with the carbons to which R5 and R6 are directly attached and the carbon directly attached to both of the carbons to which R5 and R6 are directly attached form a 5 or 6 membered heterocyclyl, heteroaryl, cycloalkyl, or a saturated or unsaturated carbocyclic moiety, all of which are optionally substituted by halo, optionally substituted lower alkyl, optionally substituted alkyl, optionally substituted alkenyl, optionally substituted alkynyl, optionally substituted alkoxy, optionally substituted cycloalkyl, optionally substituted aryl, optionally substituted heterocyclyl, optionally substituted aryl, or optionally substituted heteroaryl.

In certain embodiments R2 is hydrogen, lower alkyl, optionally substituted alkyl, optionally substituted alkenyl, optionally substituted alkynyl, optionally substituted cycloalkyl, optionally substituted heterocyclyl, optionally substituted aryl, optionally substituted heteroaryl, or —NR21R22, where R21 and R22 are independently hydrogen, lower alkyl, optionally substituted alkyl, optionally substituted alkenyl, or optionally substituted alkynyl.

In some embodiments R2 is optionally substituted lower alkyl or —NR21R22, where R21 and R22 are independently hydrogen, optionally substituted lower alkyl, or optionally substituted alkyl. In particular embodiments R2 is amino, substituted amino, methyl, ethyl, 1-propyl, 2-propyl, or (2-aminoethoxy)methyl.

In certain embodiments R3 is hydrogen, lower alkyl, optionally substituted alkyl, optionally substituted alkenyl, optionally substituted alkynyl, optionally substituted cycloalkyl, optionally substituted heterocyclyl, optionally substituted aryl, optionally substituted heteroaryl, cyano, —C(O)—R31, or —C(O)—O—R31, where R31 is hydrogen, lower alkyl, optionally substituted alkyl, optionally substituted alkenyl, optionally substituted alkynyl, optionally substituted cycloalkyl, optionally substituted heterocyclyl, optionally substituted aryl, optionally substituted aralkyl, or optionally substituted heteroaryl.

In some embodiments, R3 is optionally substituted lower alkyl, optionally substituted alkyl, optionally substituted aryl, optionally substituted heteroaryl, cyano, —C(O)—R31, or —C(O)—O—R31, where R31 is hydrogen, optionally substituted lower alkyl, optionally substituted alkyl, optionally substituted alkenyl, optionally substituted cycloalkyl, optionally substituted heterocyclyl, optionally substituted aryl, optionally substituted aralkyl, or optionally substituted heteroaryl. In particular embodiments R3 is optionally substituted lower alkyl, cyano, —C(O)—R31, or —C(O)—O—R31, where R31 is optionally substituted lower alkyl, methyl, ethyl, 1-propyl, 2-propyl, 2-methoxyethyl, benzyl, substituted benzyl, or 3,4-dimethoxybenzyl.

In certain embodiments R2 and R3 taken together with Q1 and the carbon to which R2 is attached form a 5 or 6 membered heterocyclyl, heteroaryl, cycloalkyl, or an aromatic or non-aromatic carbocyclic moiety, all of which are optionally substituted by halo, cyano, optionally substituted lower alkyl, optionally substituted alkyl, optionally substituted alkenyl, optionally substituted alkynyl, optionally substituted alkoxy, optionally substituted cycloalkyl, optionally substituted aryl, optionally substituted heteroaryl, or optionally substituted heterocyclyl. In certain such embodiments R2 and R3 taken together with Q1 and the carbon to which R2 is directly attached form a tetrazole ring; such embodiments may be represented by the Formula (II):

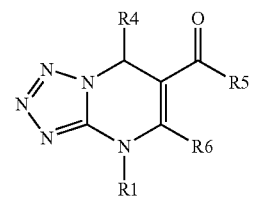

Formula (II)

wherein R1, R4, R5, and R6 are as described above with relation to Formula (I).

In certain embodiments R2 and R3 taken together with Q1 and the carbon to which R2 is directly attached form a pyrazole ring; some such embodiments may be represented by the Formula (III) or Formula (IV):

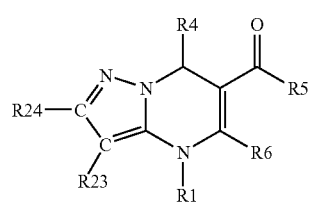

Formula (III)

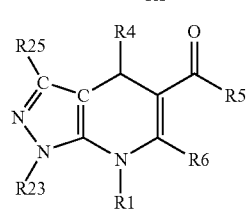

Formula (IV)

wherein R1, R4, R5, and R6 are as described above with relation to Formula (I), and R23, R24 (if present), and R25 (if present) are each independently hydrogen, cyano, halo, optionally substituted lower alkyl, optionally substituted alkyl, optionally substituted alkenyl, optionally substituted alkynyl, optionally substituted alkoxy, optionally substituted cycloalkyl, optionally substituted aryl, optionally substituted aralkyl, optionally substituted heteroaryl, or optionally substituted heterocyclyl. In particular embodiments R23, R24, and R25 are each independently methyl, ethyl, 1-propyl, 2-propyl, cyano, optionally substituted thiophenyl, optionally substituted furanyl, or optionally substituted phenyl (e.g. methylphenyl), or R23 and R24 taken together with the carbon atoms to which they are attached form an optionally substituted phenyl ring, an optionally substituted carbocyclic ring, or an optionally substituted heteroaryl ring.

In certain embodiments R2 and R3 taken together with Q1 and the carbon to which R2 is directly attached form an imidazole ring; some such embodiments may be represented by the Formula (V):

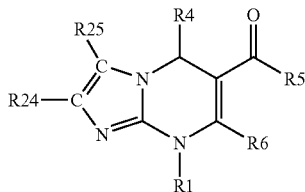

Formula (V)

wherein R1, R4, R5, and R6 are as described above with relation to Formula (I), and R24 and R25 are each independently hydrogen, cyano, halo, optionally substituted lower alkyl, optionally substituted alkyl, optionally substituted alkenyl, optionally substituted alkynyl, optionally substituted alkoxy, optionally substituted cycloalkyl, optionally substituted aryl, optionally substituted aralkyl, optionally substituted heteroaryl, or optionally substituted heterocyclyl. In particular embodiments R24 and R25 are each independently methyl, ethyl, 1-propyl, 2-propyl, cyano, optionally substituted thiophenyl, optionally substituted furanyl, or optionally substituted phenyl (e.g. methylphenyl), or R24 and R25 taken together with the carbon atoms to which they are attached form an optionally substituted phenyl ring, an optionally substituted carbocyclic ring, or an optionally substituted heteroaryl ring.

In certain embodiments R2 and R3 taken together with Q1 and the carbon to which R2 is directly attached form a five or six membered carbocyclic ring; some such embodiments may be represented by the Formula (VI):

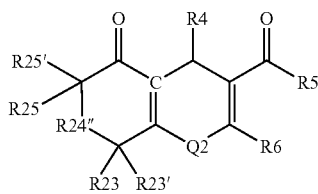

Formula (VI)

wherein Q2, R4, R5, and R6 are as described above with relation to Formula (I); R24" is a covalent bond connecting the two carbons to which R24" is attached or is —CR24R24'-; R23, R24 (if present), and R25 are each independently hydrogen, optionally substituted lower alkyl, optionally substituted alkoxy, optionally substituted aryl, optionally substituted aralkyl, optionally substituted heteroaryl, or optionally substituted heterocyclyl; and R23', R24' (if present), and R25' are each independently hydrogen or optionally substituted lower alkyl. In particular embodiments, R24" is a covalent bond connecting the two carbons to which R24" is attached or is —CR24R24'-; R23, R24 (if present), and R25 are each independently hydrogen, methyl, ethyl, optionally substituted phenyl, optionally substituted thiophenyl, optionally substituted furany; and R23', R24' (if present), and R25' are each independently hydrogen, methyl, or ethyl.

In certain embodiments R4 is optionally substituted alkyl, optionally substituted alkenyl, optionally substituted alkynyl, optionally substituted cycloalkyl, optionally substituted heterocyclyl, optionally substituted aryl, or optionally substituted heteroaryl. In certain embodiments R4 is aryl substituted with one or more groups selected from aryl, lower alkyl, alkyl, heteroaryl, halo, heterocyclyl, amino, and carboxyl, wherein said one or more groups are optionally substituted with alkyl, aryl, heteroaryl, heterocyclyl, halo, or carboxyl. In particular embodiments R4 is optionally substituted phenyl, optionally substituted biphenyl, optionally substituted naphthalenyl, optionally substituted anthracenyl, optionally substituted thiophenyl, optionally substituted (uranyl, optionally substituted benzofuranyl, optionally substituted benzothiophenyl, optionally substituted quinolinyl, optionally substituted pyrazinyl, or optionally substituted pyridinyl.

In certain embodiments R5 is optionally substituted alkyl, optionally substituted alkenyl, optionally substituted alkynyl, optionally substituted cycloalkyl, optionally substituted heterocyclyl, optionally substituted aryl, optionally substituted heteroaryl, —O—R51, or —NR52R53, where R51 is optionally substituted alkyl, optionally substituted alkenyl, optionally substituted alkynyl, optionally substituted cycloalkyl, optionally substituted heterocyclyl, optionally substituted aryl, optionally substituted heteroaryl, where R52 and R53 are each independently hydrogen, lower alkyl, optionally substituted alkyl, optionally substituted alkenyl, optionally substituted alkynyl, optionally substituted cycloalkyl, optionally substituted heterocyclyl, optionally substituted aryl, optionally substituted heteroaryl, or R52 and R53 taken together with the nitrogen to which they are both directly attached form 5 or 6 membered heterocyclyl or heteroaryl moiety, which is optionally substituted by halo, optionally substituted alkyl, optionally substituted alkenyl, optionally substituted alkynyl, optionally substituted alkoxy, optionally substituted cycloalkyl, optionally substituted heterocyclyl, optionally substituted aryl, or optionally substituted heteroaryl.

In particular embodiments, R5 is —O—R51, wherein R51 is optionally substituted lower alkyl, optionally substituted alkyl, optionally substituted benzyl, optionally substituted biphenyl, optionally substituted diphenylmethyl, methyl, ethyl, 1-propyl, 2-propyl. In particular embodiments, R5 is —NR52R53, where R52 and R53 are each independently hydrogen, lower alkyl, optionally substituted alkyl, optionally substituted cycloalkyl, optionally substituted aryl, optionally substituted benzyl, or R52 and R53 taken together with the nitrogen to which they are both directly attached form 5 or 6 membered heterocyclyl or heteroaryl moiety, which is optionally substituted by halo, alkyl, alkenyl, alkynyl, alkoxy, aryl, or cycloalkyl (each of which may be optionally substituted).

In certain embodiments, R6 is hydrogen, lower alkyl, optionally substituted alkyl, optionally substituted alkenyl, optionally substituted alkynyl, optionally substituted cycloalkyl, optionally substituted heterocyclyl, optionally substituted aryl, or optionally substituted heteroaryl, —NR61R62, where R61 and R62 are independently hydrogen, lower alkyl, optionally substituted alkyl, optionally substituted alkenyl, or optionally substituted alkynyl. In particular embodiments, R6 is methyl, trifluoromethyl, ethyl, 1-propyl, 2-propyl, n-butyl, sec-butyl, tert-butyl, 2-hydroxyethyl, 3-methoxyethyl, or (2-amino)ethoxymethyl.

In certain embodiments, R5 and R6 taken together with the carbons to which R5 and R6 are directly attached and the carbon directly attached to both of the carbons to which R5 and R6 are directly attached form a 5 or 6 membered heterocyclyl, heteroaryl, cycloalkyl, or a saturated or unsaturated carbocyclic moiety, all of which are optionally substituted by halo, optionally substituted lower alkyl, optionally substituted alkyl, optionally substituted alkenyl, optionally substituted alkynyl, optionally substituted alkoxy, optionally substituted cycloalkyl, optionally substituted aryl, optionally substituted heterocyclyl, or optionally substituted heteroaryl.

In particular embodiments, R5 and R6 taken together form a bridging group having the structure: —R54-R55-R56-R63-, where:

R54 is bound directly to the carbonyl carbon of Formula (I) and is —O—, —NR54'-, or —CR54'R54"-, where R54' and R54" are independently hydrogen, lower alkyl, or optionally substituted alkyl, optionally substituted alkenyl, optionally substituted alkynyl, optionally substituted alkoxy, optionally substituted cycloalkyl, or optionally substituted aryl.

R55 taken together with R56 is a covalent bond connecting R54 to R63, or

R55 is a covalent bond connecting R54 to R56 or is —CR55'R55"-, where R55' and R55" are independently hydrogen, lower alkyl, or optionally substituted alkyl, optionally substituted alkenyl, optionally substituted alkynyl, optionally substituted alkoxy, optionally substituted cycloalkyl, or optionally substituted aryl; and R56 is —CR56'R56"- where R56' and R56" are independently hydrogen, lower alkyl, or optionally substituted alkyl, optionally substituted alkenyl, optionally substituted alkynyl, optionally substituted alkoxy, optionally substituted cycloalkyl, or optionally substituted aryl.

R63 is —CR63'R63" where R63' and R63" are independently hydrogen, lower alkyl, or optionally substituted alkyl, optionally substituted alkenyl, optionally substituted alkynyl, optionally substituted alkoxy, optionally substituted cycloalkyl, or optionally substituted aryl.

In particular embodiments, R5 and R6 taken together form a bridging group having the structure: —N(R57)(R57')-C(O)—N(R64)(R64'), where R57, R57', R64, and R64' are independently hydrogen, lower alkyl, or optionally substituted alkyl, optionally substituted alkenyl, optionally substituted alkynyl, optionally substituted alkoxy, optionally substituted cycloalkyl, or optionally substituted aryl.

Where a given group is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

In typical embodiments, the compounds provided by the present invention are effective in the treatment of conditions known to respond to administration of late sodium channel blockers, including cardiovascular diseases such as atrial and ventricular arrhythmias, Prinzmetal's (variant) angina, stable angina, unstable angina, ischemia and reperfusion injury in cardiac, kidney, liver and the brain, exercise induced angina, congestive heart disease, and myocardial infarction. In some embodiments, compounds provided by the present invention which function as late sodium channel blockers may be used in the treatment of diseases affecting the neuromuscular system resulting in pain, seizures, or paralysis, or in the treatment of diabetes and disease states related to diabetes, such as diabetic peripheral neuropathy.

Certain compounds of the invention may also possess a sufficient activity in modulating neuronal sodium channels and may have appropriate pharmacokinetic properties such that they may active with regard to the central and/or peripheral nervous system. Consequently, some compounds of the invention may also be of use in the treatment of pain of neuropathic origin.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a hydrate of an addition salt, a tautomeric form, a polymorph, an enantiomer, a mixture of enantiomers, a stereoisomer or mixture of stereoisomers (pure or as a racemic or non-racemic mixture) of a compound described herein, e.g. a compound of Formulae (I), (II), (III), (IV), (V), (VI), further e.g. a compound listed in Table 1, below.

Pharmaceutical Compositions

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992, 445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Synthetic Reaction Parameters

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

SYNTHESIS OF EXAMPLE COMPOUNDS

The compounds of the invention may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formulae (I)-(VI), may be accomplished as described in the following examples. If available, reagents may be purchased commercially, e.g. from Sigma Aldrich or other chemical suppliers.

General Syntheses

Typical embodiments of compounds in accordance with the present invention may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups (e.g. R1, R2, R3, R4, R5 and/or R6) are defined, the necessary starting materials generally may be determined by inspection. Starting materials are typically obtained from commercial sources or synthesized using published methods. Note that in the following examples, general syntheses may be shown using groups denoted with subscripts (e.g. $R_1$, $R_2$, $R_3$, etc.) These are distinguished from the groups described herein that do not have subscripts (e.g. R1, R2, R3 etc.). In the syntheses generally described herein, the groups denoted with subscripts are used to describe the general form of the reaction. For synthesizing compounds which are embodiments of the present invention, inspection of the structure of the compound to be synthesized will provide the identity of each substituent group. The identity of the final product will generally render apparent the identity of the necessary starting materials by a simple process of inspection, given the examples herein.

Example 1

Example 1A

General Method for Synthesis of Compounds of Formula (II)

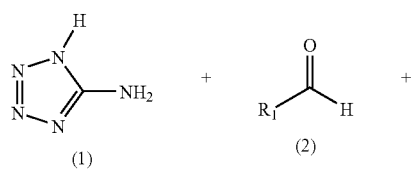

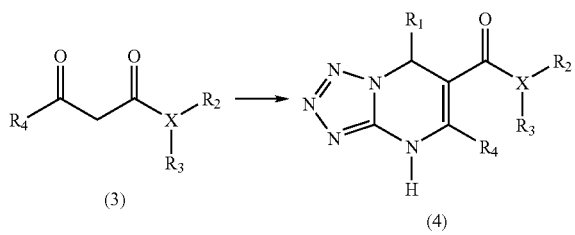

Referring to the above reaction, 5-aminotetrazole (1) is reacted with an aldehyde (2) and a beta-keto compound (3) to give the product (4), which is a compound of Formula (II). Given a desired product (4) for which the substituent groups $R_1$, $X(R_2)(R_3)$, and $R_4$ are defined, the necessary starting materials (2) and (3) may be determined by inspection. As used herein, a "beta-keto compound" is a compound that has a structure which includes a first carbonyl group and a second carbonyl group that is beta to the first carbonyl; the first carbonyl is typically part of an ester or amide group. In some cases of the beta-keto compound (3), X is a nitrogen and $R_2$ and $R_3$ may be substituents (such as are described elsewhere herein) bound to the nitrogen, such that the beta-keto compound (3) is a beta-keto amide. In certain other cases, X taken together with $R_3$ is an oxygen and $R_2$ may be a substituent (such as described elsewhere herein) bound to the oxygen, such that the beta-keto compound (3) is a beta-keto ester.

To a solution of 5-aminotetrazole (1) (10.0 mmole) and triethylamine (1.8 mmole) in hot ethanol (20 ml) was added the aldehyde (2) (10.0 mmole) followed by the beta-keto compound (3) (10.0 mmole). The mixture was heated at reflux for 15 h. A precipitate was usually observed and upon cooling the mixture to room temperature, it was filtered and washed with ethanol then ethyl ether to provide the desired product as a white powder. Yields typically were in the range of between 5-90% depending upon substituents of the aldehyde (2) and the beta-keto compound (3).

Example 1B

Preparation of a Compound of Formula (II) in which R4 is Napthyl, R5 is Ethoxy, and R6 is 2-propyl Synthesis of ethyl 5-isopropyl-7-(naphthalen-1-yl)-4,7-dihydrotetrazolo[1,5-a]pyrimidine-6-carboxylate (PT-013)

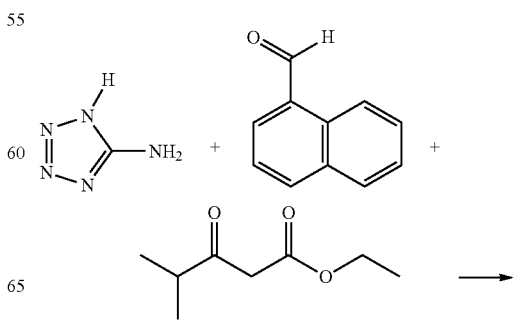

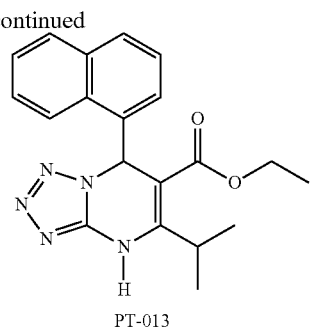

PT-013

The 5-aminotetrazole (850 mg; 10.0 mmole) is dissolved in hot ethanol (25 ml) with triethylamine (1.8 mmole; 0.25 ml). When all solids are dissolved (about ten minutes of heating at 82° C.), 1-naphthaldehyde (1.36 ml; 10.0 mmole) is added followed by ethyl isopropylacetoacetate (1.60 ml; 10.0 mmole). The clear solution is maintained at reflux for 15 h. The ethanol is removed in vacuo and the residue is dissolved in ethyl acetate. The ethyl acetate phase is added to a separatory funnel and subsequently washed with 1M HCl, water, then brine. The organic phase is dried over $MgSO_4$ and filtered. The organic phase is reduced in volume in vacuo to get an oil. A 1:1 mixture of ethyl acetate and hexanes was added to the viscous oil and stirred with a spatula to provide a precipitate. The solid was filtered to provide the product (0.700 g, 19%) as a white powder. $^1$H NMR (400 MHz; $CDCl_3$) d 11.0 (bs, 1H); 7.88 (d, 1H, J=8.2 Hz); 7.82 (d, 1H, J=8.2 Hz); 7.70-7.36 (m, 5H); 4.5 (m, 1H); 3.92-3.80 (m, 2H); 1.55 (d, 3H, J=6.7 Hz); 1.40 (d, 3H, J=7.0 Hz); 0.74 (at, 3H, J=7.0 Hz). LC MS shows MH+ at 364 and 2 MH+ at 727.

Example 1C

Preparation of a Compound of Formula (II) Varying R4, R5, R6

Similarly, by essentially following the procedures set out in Examples 1A and 1B above, but replacing the aldehyde (2) with other aldehydes of general formula $R_1$—C(O)H and/or replacing the beta-keto compound (3) with other beta-keto compounds having the necessary substituents to result in the indicated products, the following compounds of Formula (II) were prepared:

TABLE 1

| ID (PT-nnn) | Name of Compound |
| --- | --- |
| PT-001 | 1,2,3,4-tetrahydronaphthalen-1-yl 5-methyl-7-(naphthalen-1-yl)-4,7-dihydrotetrazolo[1,5-a]pyrimidine-6-carboxylate |
| PT-002 | cyclopropyl(phenyl)methyl 5-methyl-7-(naphthalen-1-yl)-4,7-dihydrotetrazolo[1,5-a]pyrimidine-6-carboxylate |
| PT-003 | 4-phenoxybenzyl 5-methyl-7-(naphthalen-1-yl)-4,7-dihydrotetrazolo[1,5-a]pyrimidine-6-carboxylate |
| PT-004 | biphenyl-4-ylmethyl 5-methyl-7-(naphthalen-1-yl)-4,7-dihydrotetrazolo[1,5-a]pyrimidine-6-carboxylate |
| PT-005 | biphenyl-2-ylmethyl 5-methyl-7-(naphthalen-1-yl)-4,7-dihydrotetrazolo[1,5-a]pyrimidine-6-carboxylate |
| PT-006 | biphenyl-3-ylmethyl 5-methyl-7-(naphthalen-1-yl)-4,7-dihydrotetrazolo[1,5-a]pyrimidine-6-carboxylate |
| PT-007 | bis(4-fluorophenyl)methyl 5-methyl-7-(naphthalen-1-yl)-4,7-dihydrotetrazolo[1,5-a]pyrimidine-6-carboxylate |
| PT-008 | ethyl 5-methyl-7-(naphthalen-2-yl)-4,7-dihydrotetrazolo[1,5-a]pyrimidine-6-carboxylate |
| PT-009 | ethyl 7-(naphthalen-1-yl)-5-(trifluoromethyl)-4,7-dihydrotetrazolo[1,5-a]pyrimidine-6-carboxylate |
| PT-010 | ethyl 5-ethyl-7-(naphthalen-1-yl)-4,7-dihydrotetrazolo[1,5-a]pyrimidine-6-carboxylate |
| PT-011 | ethyl 5-ethyl-7-(naphthalen-2-yl)-4,7-dihydrotetrazolo[1,5-a]pyrimidine-6-carboxylate |
| PT-012 | ethyl 5-isopropyl-7-(naphthalen-2-yl)-4,7-dihydrotetrazolo[1,5-a]pyrimidine-6-carboxylate |
| PT-013 | ethyl 5-isopropyl-7-(naphthalen-1-yl)-4,7-dihydrotetrazolo[1,5-a]pyrimidine-6-carboxylate |
| PT-014 | 2,2,2-trifluoroethyl 5-methyl-7-(naphthalen-1-yl)-4,7-dihydrotetrazolo[1,5-a]pyrimidine-6-carboxylate |
| PT-016 | ethyl 7-(thiophen-2-yl)-5-(trifluoromethyl)-4,7-dihydrotetrazolo[1,5-a]pyrimidine-6-carboxylate |
| PT-017 | ethyl 7-(benzo[b]thiophen-3-yl)-5-methyl-4,7-dihydrotetrazolo[1,5-a]pyrimidine-6-carboxylate |
| PT-018 | ethyl 5-methyl-7-(3-methylbenzo[b]thiophen-2-yl)-4,7-dihydrotetrazolo[1,5-a]pyrimidine-6-carboxylate |
| PT-019 | ethyl 7-(benzofuran-2-yl)-5-methyl-4,7-dihydrotetrazolo[1,5-a]pyrimidine-6-carboxylate |
| PT-020 | isopropyl 5-methyl-7-(naphthalen-2-yl)-4,7-dihydrotetrazolo[1,5-a]pyrimidine-6-carboxylate |
| PT-021 | isopropyl 5-methyl-7-(naphthalen-1-yl)-4,7-dihydrotetrazolo[1,5-a]pyrimidine-6-carboxylate |
| PT-022 | tert-butyl 5-methyl-7-(naphthalen-2-yl)-4,7-dihydrotetrazolo[1,5-a]pyrimidine-6-carboxylate |
| PT-023 | tert-butyl 5-methyl-7-(naphthalen-1-yl)-4,7-dihydrotetrazolo[1,5-a]pyrimidine-6-carboxylate |
| PT-024 | benzyl 5-methyl-7-(3-phenoxyphenyl)-4,7-dihydrotetrazolo[1,5-a]pyrimidine-6-carboxylate |

TABLE 1-continued

| ID (PT-nnn) | Name of Compound |
|---|---|
| PT-025 | benzyl 7-(biphenyl-2-yl)-5-methyl-4,7-dihydrotetrazolo[1,5-a]pyrimidine-6-carboxylate |
| PT-026 | benzyl 7-(biphenyl-3-yl)-5-methyl-4,7-dihydrotetrazolo[1,5-a]pyrimidine-6-carboxylate |
| PT-027 | benzyl 5-methyl-7-(naphthalen-1-yl)-4,7-dihydrotetrazolo[1,5-a]pyrimidine-6-carboxylate |
| PT-028 | benzyl 5-methyl-7-(naphthalen-2-yl)-4,7-dihydrotetrazolo[1,5-a]pyrimidine-6-carboxylate |
| PT-029 | 4-iodobenzyl 5-methyl-7-(naphthalen-1-yl)-4,7-dihydrotetrazolo[1,5-a]pyrimidine-6-carboxylate |
| PT-030 | benzyl 7-(2-methoxynaphthalen-1-yl)-5-methyl-4,7-dihydrotetrazolo[1,5-a]pyrimidine-6-carboxylate |
| PT-031 | benzyl 5-methyl-7-(4-methylnaphthalen-1-yl)-4,7-dihydrotetrazolo[1,5-a]pyrimidine-6-carboxylate |
| PT-032 | benzyl 7-(4-(dimethylamino)naphthalen-1-yl)-5-methyl-4,7-dihydrotetrazolo[1,5-a]pyrimidine-6-carboxylate |
| PT-033 | benzyl 7-(4,6-dimethoxynaphthalen-1-yl)-5-methyl-4,7-dihydrotetrazolo[1,5-a]pyrimidine-6-carboxylate |
| PT-034 | benzyl 7-(benzo[d][1,3]dioxol-4-yl)-5-methyl-4,7-dihydrotetrazolo[1,5-a]pyrimidine-6-carboxylate |
| PT-035 | benzyl 7-(2,3-dihydrobenzo[b][1,4]dioxin-6-yl)-5-methyl-4,7-dihydrotetrazolo[1,5-a]pyrimidine-6-carboxylate |
| PT-036 | benzyl 7-(2,3-dihydrobenzo[b][1,4]dioxin-5-yl)-5-methyl-4,7-dihydrotetrazolo[1,5-a]pyrimidine-6-carboxylate |
| PT-037 | benzyl 5-methyl-7-(quinolin-8-yl)-4,7-dihydrotetrazolo[1,5-a]pyrimidine-6-carboxylate |
| PT-038 | benzyl 5-methyl-7-(quinolin-5-yl)-4,7-dihydrotetrazolo[1,5-a]pyrimidine-6-carboxylate |
| PT-039 | benzyl 7-(anthracen-9-yl)-5-methyl-4,7-dihydrotetrazolo[1,5-a]pyrimidine-6-carboxylate |
| PT-040 | benzyl 5-methyl-7-(thiophen-2-yl)-4,7-dihydrotetrazolo[1,5-a]pyrimidine-6-carboxylate |
| PT-041 | benzyl 5-methyl-7-(thiophen-3-yl)-4,7-dihydrotetrazolo[1,5-a]pyrimidine-6-carboxylate |
| PT-042 | benzyl 7-(benzo[b]thiophen-3-yl)-5-methyl-4,7-dihydrotetrazolo[1,5-a]pyrimidine-6-carboxylate |
| PT-043 | benzyl 7-(benzo[b]thiophen-2-yl)-5-methyl-4,7-dihydrotetrazolo[1,5-a]pyrimidine-6-carboxylate |
| PT-044 | benzyl 5-methyl-7-(3-methylbenzo[b]thiophen-2-yl)-4,7-dihydrotetrazolo[1,5-a]pyrimidine-6-carboxylate |
| PT-045 | benzyl 7-(benzofuran-2-yl)-5-methyl-4,7-dihydrotetrazolo[1,5-a]pyrimidine-6-carboxylate |
| PT-046 | 4-cyanobenzyl 5-methyl-7-(naphthalen-1-yl)-4,7-dihydrotetrazolo[1,5-a]pyrimidine-6-carboxylate |
| PT-047 | R)-1-phenylethyl 5-methyl-7-(naphthalen-1-yl)-4,7-dihydrotetrazolo[1,5-a]pyrimidine-6-carboxylate |
| PT-048 | (S)-1-phenylethyl 5-methyl-7-(naphthalen-1-yl)-4,7-dihydrotetrazolo[1,5-a]pyrimidine-6-carboxylate |
| PT-049 | (S)-((S)-1-phenylethyl) 5-methyl-7-(naphthalen-1-yl)-4,7-dihydrotetrazolo[1,5-a]pyrimidine-6-carboxylate |
| PT-050 | (R)-((S)-1-phenylethyl) 5-methyl-7-(naphthalen-1-yl)-4,7-dihydrotetrazolo[1,5-a]pyrimidine-6-carboxylate |
| PT-051 | 4-(trifluoromethyl)benzyl 5-methyl-7-(naphthalen-1-yl)-4,7-dihydrotetrazolo[1,5-a]pyrimidine-6-carboxylate |
| PT-052 | 4-(trifluoromethoxy)benzyl 5-methyl-7-(naphthalen-1-yl)-4,7-dihydrotetrazolo[1,5-a]pyrimidine-6-carboxylate |
| PT-053 | (S)-1-phenylethyl 7-(2-methoxynaphthalen-1-yl)-5-methyl-4,7-dihydrotetrazolo[1,5-a]pyrimidine-6-carboxylate |
| PT-054 | (S)-1-phenylethyl 7-(4-(dimethylamino)naphthalen-1-yl)-5-methyl-4,7-dihydrotetrazolo[1,5-a]pyrimidine-6-carboxylate |
| PT-055 | (S)-1-phenylethyl 7-(anthracen-9-yl)-5-methyl-4,7-dihydrotetrazolo[1,5-a]pyrimidine-6-carboxylate |
| PT-056 | (S)-1-phenylethyl 7-(benzo[b]thiophen-2-yl)-5-methyl-4,7-dihydrotetrazolo[1,5-a]pyrimidine-6-carboxylate |
| PT-057 | (S)-1-phenylethyl 7-(benzo[b]thiophen-2-yl)-5-methyl-4,7-dihydrotetrazolo[1,5-a]pyrimidine-6-carboxylate |
| PT-058 | (S)-1-phenylethyl 7-(benzofuran-2-yl)-5-methyl-4,7-dihydrotetrazolo[1,5-a]pyrimidine-6-carboxylate |
| PT-059 | (S)-1-phenylethyl 7-(benzofuran-2-yl)-5-methyl-4,7-dihydrotetrazolo[1,5-a]pyrimidine-6-carboxylate |
| PT-061 | 3,4-dimethoxybenzyl 5-methyl-7-(naphthalen-1-yl)-4,7-dihydrotetrazolo[1,5-a]pyrimidine-6-carboxylate |
| PT-062 | 2,3-dihydro-1H-inden-1-yl 5-methyl-7-(naphthalen-1-yl)-4,7-dihydrotetrazolo[1,5-a]pyrimidine-6-carboxylate |
| PT-063 | 1-phenylpropyl 5-methyl-7-(naphthalen-1-yl)-4,7-dihydrotetrazolo[1,5-a]pyrimidine-6-carboxylate |

TABLE 1-continued

| ID (PT-nnn) | Name of Compound |
| --- | --- |
| PT-064 | 1-phenylpropan-2-yl 5-methyl-7-(naphthalen-1-yl)-4,7-dihydrotetrazolo[1,5-a]pyrimidine-6-carboxylate |
| PT-065 | 2-phenylpropan-2-yl 5-methyl-7-(naphthalen-1-yl)-4,7-dihydrotetrazolo[1,5-a]pyrimidine-6-carboxylate |
| PT-067 | N-benzyl-5-methyl-7-(naphthalen-1-yl)-4,7-dihydrotetrazolo[1,5-a]pyrimidine-6-carboxamide |
| PT-068 | N-benzyl-5-methyl-7-(naphthalen-2-yl)-4,7-dihydrotetrazolo[1,5-a]pyrimidine-6-carboxamide |
| PT-069 | N'-benzoyl-5-methyl-7-(naphthalen-1-yl)-4,7-dihydrotetrazolo[1,5-a]pyrimidine-6-carbohydrazide |
| PT-071 | 5-methyl-7-(naphthalen-1-yl)-N-((S)-1-phenylethyl)-4,7-dihydrotetrazolo[1,5-a]pyrimidine-6-carboxamide |
| PT-072 | 9-(naphthalen-1-yl)-5,6,7,9-tetrahydrotetrazolo[5,1-b]quinazolin-8(4H)-one |
| PT-192 | ethyl 5-methyl-7-(naphthalen-1-yl)-4,7-dihydrotetrazolo[1,5-a]pyrimidine-6-carboxylate |
| PT-196 | benzyl 5-methyl-7-(quinolin-2-yl)-4,7-dihydrotetrazolo[1,5-a]pyrimidine-6-carboxylate |
| PT-197 | benzyl 5-methyl-7-(quinolin-4-yl)-4,7-dihydrotetrazolo[1,5-a]pyrimidine-6-carboxylate |
| PT-201 | diethyl 7,7'-(1,4-phenylene)bis(5-methyl-4,7-dihydrotetrazolo[1,5-a]pyrimidine-6-carboxylate) |
| PT-202 | diethyl 7,7'-(1,3-phenylene)bis(5-methyl-4,7-dihydrotetrazolo[1,5-a]pyrimidine-6-carboxylate) |
| PT-251 | 2-(4-(methoxycarbonyl)phenoxy)ethyl 5-methyl-7-(naphthalen-1-yl)-4,7-dihydrotetrazolo[1,5-a]pyrimidine-6-carboxylate |
| PT-255 | 2-(6-(benzyloxycarbonyl)-5-methyl-4,7-dihydrotetrazolo[1,5-a]pyrimidin-7-yl)phenylboronic acid |
| PT-256 | 2-(6-(benzyloxycarbonyl)-5-methyl-4,7-dihydrotetrazolo[1,5-a]pyrimidin-7-yl)thiophen-3-ylboronic acid |
| PT-260 | 2,3-dihydro-1H-inden-2-yl 5-methyl-7-(naphthalen-1-yl)-4,7-dihydrotetrazolo[1,5-a]pyrimidine-6-carboxylate |
| PT-262 | 2-methoxybenzyl 7-(2,6-dimethylphenyl)-5-methyl-4,7-dihydrotetrazolo[1,5-a]pyrimidine-6-carboxylate |
| PT-264 | 2-methyl-1-phenylpropan-2-yl 5-methyl-7-(naphthalen-1-yl)-4,7-dihydrotetrazolo[1,5-a]pyrimidine-6- |
| PT-277 | 3-(6-(benzyloxycarbonyl)-5-methyl-4,7-dihydrotetrazolo[1,5-a]pyrimidin-7-yl)thiophen-2-ylboronic acid |
| PT-278 | 3-cyanobenzyl 5-methyl-7-(naphthalen-1-yl)-4,7-dihydrotetrazolo[1,5-a]pyrimidine-6-carboxylate |
| PT-279 | 4-((1H-pyrazol-1-yl)methyl)benzyl 5-methyl-7-(naphthalen-1-yl)-4,7-dihydrotetrazolo[1,5-a]pyrimidine-6-carboxylate |
| PT-280 | 4-((1H-pyrazol-1-yl)methyl)benzyl 5-methyl-7-(thiophen-2-yl)-4,7-dihydrotetrazolo[1,5-a]pyrimidine-6-carboxylate |
| PT-283 | 4-((1H-pyrazol-1-yl)methyl)benzyl 7-(4-(dimethylamino)naphthalen-1-yl)-5-methyl-4,7-dihydrotetrazolo[1,5-a]pyrimidine-6-carboxylate |
| PT-284 | 4-((1H-pyrazol-1-yl)methyl)benzyl 7-(4-methoxynaphthalen-1-yl)-5-methyl-4,7-dihydrotetrazolo[1,5-a]pyrimidine-6-carboxylate |
| PT-289 | 4-(1H-pyrazol-1-yl)benzyl 5-methyl-7-(naphthalen-1-yl)-4,7-dihydrotetrazolo[1,5-a]pyrimidine-6-carboxylate |
| PT-300 | 4-(6-(benzyloxycarbonyl)-5-methyl-4,7-dihydrotetrazolo[1,5-a]pyrimidin-7-yl)phenylboronic acid |
| PT-304 | 4-chloro-2-methoxybenzyl 5-methyl-7-(naphthalen-1-yl)-4,7-dihydrotetrazolo[1,5-a]pyrimidine-6-carboxylate |
| PT-306 | 4-chloro-2-methoxybenzyl 7-(2,6-dichlorophenyl)-5-methyl-4,7-dihydrotetrazolo[1,5-a]pyrimidine-6-carboxylate |
| PT-307 | 4-chloro-2-methoxybenzyl 7-(2,6-dimethylphenyl)-5-methyl-4,7-dihydrotetrazolo[1,5-a]pyrimidine-6-carboxylate |
| PT-308 | 4-chloro-2-methoxybenzyl 7-(2-bromophenyl)-5-methyl-4,7-dihydrotetrazolo[1,5-a]pyrimidine-6-carboxylate |
| PT-309 | 5-methyl-7-(naphthalen-1-yl)-N'-(2-phenylacetyl)-4,7-dihydrotetrazolo[1,5-a]pyrimidine-6-carbohydrazide |
| PT-310 | 5-methyl-7-(naphthalen-1-yl)-N-phenethyl-4,7-dihydrotetrazolo[1,5-a]pyrimidine-6-carboxamide |
| PT-319 | allyl 5-methyl-7-(naphthalen-1-yl)-4,7-dihydrotetrazolo[1,5-a]pyrimidine-6-carboxylate |
| PT-339 | benzyl 5-methyl-7-(2-(4-(methylsulfonyl)piperazin-1-yl)phenyl)-4,7-dihydrotetrazolo[1,5-a]pyrimidine-6-carboxylate |
| PT-340 | benzyl 5-methyl-7-(2-(4-methylpiperazin-1-yl)phenyl)-4,7-dihydrotetrazolo[1,5-a]pyrimidine-6-carboxylate |
| PT-341 | benzyl 5-methyl-7-(2-(4-methylpiperazin-1-yl)thiazol-5-yl)-4,7-dihydrotetrazolo[1,5-a]pyrimidine-6-carboxylate |
| PT-342 | benzyl 5-methyl-7-(2-(piperidin-1-yl)phenyl)-4,7-dihydrotetrazolo[1,5-a]pyrimidine-6-carboxylate |
| PT-343 | benzyl 5-methyl-7-(2,4,6-trimethoxyphenyl)-4,7-dihydrotetrazolo[1,5-a]pyrimidine-6-carboxylate |
| PT-345 | benzyl 5-methyl-7-(2-morpholinophenyl)-4,7-dihydrotetrazolo[1,5-a]pyrimidine-6-carboxylate |

TABLE 1-continued

| ID (PT-nnn) | Name of Compound |
|---|---|
| PT-346 | benzyl 5-methyl-7-(2-morpholinothiazol-5-yl)-4,7-dihydrotetrazolo[1,5-a]pyrimidine-6-carboxylate |
| PT-347 | benzyl 5-methyl-7-(2-nitro-4-(trifluoromethyl)phenyl)-4,7-dihydrotetrazolo[1,5-a]pyrimidine-6-carboxylate |
| PT-353 | benzyl 5-methyl-7-(4-(methylsulfonyl)-2-nitrophenyl)-4,7-dihydrotetrazolo[1,5-a]pyrimidine-6-carboxylate |
| PT-355 | benzyl 5-methyl-7-(4-(methylsulfonyl)phenyl)-4,7-dihydrotetrazolo[1,5-a]pyrimidine-6-carboxylate |
| PT-356 | benzyl 5-methyl-7-(4-(methylthio)phenyl)-4,7-dihydrotetrazolo[1,5-a]pyrimidine-6-carboxylate |
| PT-357 | benzyl 5-methyl-7-(4-(trifluoromethoxy)phenyl)-4,7-dihydrotetrazolo[1,5-a]pyrimidine-6-carboxylate |
| PT-358 | benzyl 5-methyl-7-(4-(trifluoromethyl)phenyl)-4,7-dihydrotetrazolo[1,5-a]pyrimidine-6-carboxylate |
| PT-359 | benzyl 5-methyl-7-(4-(trifluoromethylthio)phenyl)-4,7-dihydrotetrazolo[1,5-a]pyrimidine-6-carboxylate |
| PT-364 | benzyl 5-methyl-7-(thiazol-2-yl)-4,7-dihydrotetrazolo[1,5-a]pyrimidine-6-carboxylate |
| PT-365 | benzyl 5-methyl-7-(thiazol-5-yl)-4,7-dihydrotetrazolo[1,5-a]pyrimidine-6-carboxylate |
| PT-373 | benzyl 7-(2-((R)-3-(ethoxycarbonyl)piperidin-1-yl)-4-methoxyphenyl)-5-methyl-4,7-dihydrotetrazolo[1,5-a]pyrimidine-6-carboxylate |
| PT-374 | benzyl 7-(2-(2-(dimethylamino)ethoxy)phenyl)-5-methyl-4,7-dihydrotetrazolo[1,5-a]pyrimidine-6-carboxylate |
| PT-384 | benzyl 7-(2,4-bis(trifluoromethyl)phenyl)-5-methyl-4,7-dihydrotetrazolo[1,5-a]pyrimidine-6-carboxylate |
| PT-385 | benzyl 7-(2,4-dimethoxyphenyl)-5-methyl-4,7-dihydrotetrazolo[1,5-a]pyrimidine-6-carboxylate |
| PT-386 | benzyl 7-(2-bromobenzo[b]thiophen-3-yl)-5-methyl-4,7-dihydrotetrazolo[1,5-a]pyrimidine-6-carboxylate |
| PT-387 | benzyl 7-(2-bromophenyl)-5-methyl-4,7-dihydrotetrazolo[1,5-a]pyrimidine-6-carboxylate |
| PT-389 | benzyl 7-(2-cyano-4-methoxyphenyl)-5-methyl-4,7-dihydrotetrazolo[1,5-a]pyrimidine-6-carboxylate |
| PT-391 | benzyl 7-(2-fluorophenyl)-5-methyl-4,7-dihydrotetrazolo[1,5-a]pyrimidine-6-carboxylate |
| PT-392 | benzyl 7-(2-hydroxy-6-methoxyphenyl)-5-methyl-4,7-dihydrotetrazolo[1,5-a]pyrimidine-6-carboxylate |
| PT-395 | benzyl 7-(2-methoxy-4-nitrophenyl)-5-methyl-4,7-dihydrotetrazolo[1,5-a]pyrimidine-6-carboxylate |
| PT-398 | benzyl 7-(3,3'-bithiophen-5-yl)-5-methyl-4,7-dihydrotetrazolo[1,5-a]pyrimidine-6-carboxylate |
| PT-400 | benzyl 7-(3-bromofuran-2-yl)-5-methyl-4,7-dihydrotetrazolo[1,5-a]pyrimidine-6-carboxylate |
| PT-401 | benzyl 7-(3-bromothiophen-2-yl)-5-methyl-4,7-dihydrotetrazolo[1,5-a]pyrimidine-6-carboxylate |
| PT-402 | benzyl 7-(4-(1H-imidazol-1-yl)phenyl)-5-methyl-4,7-dihydrotetrazolo[1,5-a]pyrimidine-6-carboxylate |
| PT-405 | benzyl 7-(4-(2-(dimethylamino)ethoxy)phenyl)-5-methyl-4,7-dihydrotetrazolo[1,5-a]pyrimidine-6-carboxylate |
| PT-406 | benzyl 7-(4-(2-methoxyethoxy)phenyl)-5-methyl-4,7-dihydrotetrazolo[1,5-a]pyrimidine-6-carboxylate |
| PT-408 | benzyl 7-(4-(dimethylamino)-2-methoxyphenyl)-5-methyl-4,7-dihydrotetrazolo[1,5-a]pyrimidine-6-carboxylate |
| PT-409 | benzyl 7-(4-(dimethylamino)-2-nitrophenyl)-5-methyl-4,7-dihydrotetrazolo[1,5-a]pyrimidine-6-carboxylate |
| PT-410 | benzyl 7-(4-(dimethylamino)phenyl)-5-methyl-4,7-dihydrotetrazolo[1,5-a]pyrimidine-6-carboxylate |
| PT-411 | benzyl 7-(4-(methoxycarbonyl)-2-nitrophenyl)-5-methyl-4,7-dihydrotetrazolo[1,5-a]pyrimidine-6-carboxylate |
| PT-412 | benzyl 7-(4-(methoxycarbonyl)phenyl)-5-methyl-4,7-dihydrotetrazolo[1,5-a]pyrimidine-6-carboxylate |
| PT-414 | benzyl 7-(4,5-dimethylthiophen-2-yl)-5-methyl-4,7-dihydrotetrazolo[1,5-a]pyrimidine-6-carboxylate |
| PT-416 | benzyl 7-(4-bromo-2-fluorophenyl)-5-methyl-4,7-dihydrotetrazolo[1,5-a]pyrimidine-6-carboxylate |
| PT-417 | benzyl 7-(4-cyano-2-methoxyphenyl)-5-methyl-4,7-dihydrotetrazolo[1,5-a]pyrimidine-6-carboxylate |
| PT-418 | benzyl 7-(4-cyanophenyl)-5-methyl-4,7-dihydrotetrazolo[1,5-a]pyrimidine-6-carboxylate |
| PT-419 | benzyl 7-(4-methoxy-2-nitrophenyl)-5-methyl-4,7-dihydrotetrazolo[1,5-a]pyrimidine-6-carboxylate |
| PT-421 | benzyl 7-(4-methoxynaphthalen-1-yl)-5-methyl-4,7-dihydrotetrazolo[1,5-a]pyrimidine-6-carboxylate |
| PT-422 | benzyl 7-(9-ethyl-9H-carbazol-3-yl)-5-methyl-4,7-dihydrotetrazolo[1,5-a]pyrimidine-6-carboxylate |

TABLE 1-continued

| ID (PT-nnn) | Name of Compound |
|---|---|
| PT-423 | bis(4-fluorophenyl)methyl 5-methyl-7-(thiophen-2-yl)-4,7-dihydrotetrazolo[1,5-a]pyrimidine-6-carboxylate |
| PT-426 | cyclopropylmethyl 7-(2-bromobenzo[b]thiophen-3-yl)-5-methyl-4,7-dihydrotetrazolo[1,5-a]pyrimidine-6-carboxylate |
| PT-457 | ethyl 5-methyl-7-(2-(2-methyl-1H-imidazol-1-yl)phenyl)-4,7-dihydrotetrazolo[1,5-a]pyrimidine-6-carboxylate hydrochloride |
| PT-458 | ethyl 5-methyl-7-(2-(4-sulfamoylphenoxy)phenyl)-4,7-dihydrotetrazolo[1,5-a]pyrimidine-6-carboxylate |
| PT-459 | ethyl 5-methyl-7-(2-(pyridin-3-yl)phenyl)-4,7-dihydrotetrazolo[1,5-a]pyrimidine-6-carboxylate |
| PT-460 | ethyl 5-methyl-7-(2-(pyridin-4-yl)phenyl)-4,7-dihydrotetrazolo[1,5-a]pyrimidine-6-carboxylate |
| PT-461 | ethyl 5-methyl-7-(2-(pyrimidin-5-yl)phenyl)-4,7-dihydrotetrazolo[1,5-a]pyrimidine-6-carboxylate |
| PT-462 | ethyl 5-methyl-7-(2-(thiophen-2-yl)phenyl)-4,7-dihydrotetrazolo[1,5-a]pyrimidine-6-carboxylate |
| PT-464 | ethyl 5-methyl-7-(3-phenoxyphenyl)-4,7-dihydrotetrazolo[1,5-a]pyrimidine-6-carboxylate |
| PT-475 | ethyl 7-(2-(1H-1,2,4-triazol-1-yl)phenyl)-5-methyl-4,7-dihydrotetrazolo[1,5-a]pyrimidine-6-carboxylate |
| PT-476 | ethyl 7-(2-(1H-imidazol-1-yl)phenyl)-5-methyl-4,7-dihydrotetrazolo[1,5-a]pyrimidine-6-carboxylate hydrochloride |
| PT-477 | ethyl 7-(2-(1H-pyrazol-1-yl)phenyl)-5-methyl-4,7-dihydrotetrazolo[1,5-a]pyrimidine-6-carboxylate hydrochloride |
| PT-484 | ethyl 7-(2-(4-(ethoxycarbonyl)piperidin-1-yl)phenyl)-5-methyl-4,7-dihydrotetrazolo[1,5-a]pyrimidine-6-carboxylate |
| PT-485 | ethyl 7-(2-(4-cyanophenoxy)phenyl)-5-methyl-4,7-dihydrotetrazolo[1,5-a]pyrimidine-6-carboxylate |
| PT-486 | ethyl 7-(2,6-dichlorophenyl)-5-methyl-4,7-dihydrotetrazolo[1,5-a]pyrimidine-6-carboxylate |
| PT-487 | ethyl 7-(2,6-dimethylphenyl)-5-methyl-4,7-dihydrotetrazolo[1,5-a]pyrimidine-6-carboxylate |
| PT-489 | ethyl 7-(2-bromobenzo[b]thiophen-3-yl)-5-methyl-4,7-dihydrotetrazolo[1,5-a]pyrimidine-6-carboxylate |
| PT-492 | ethyl 7-(2-iodophenyl)-5-methyl-4,7-dihydrotetrazolo[1,5-a]pyrimidine-6-carboxylate |
| PT-498 | ethyl 7-(3-bromothiophen-2-yl)-5-methyl-4,7-dihydrotetrazolo[1,5-a]pyrimidine-6-carboxylate |
| PT-501 | ethyl 7-(4-(dimethylamino)-2-nitrophenyl)-5-methyl-4,7-dihydrotetrazolo[1,5-a]pyrimidine-6-carboxylate |
| PT-504 | ethyl 7-(4-methoxynaphthalen-1-yl)-5-methyl-4,7-dihydrotetrazolo[1,5-a]pyrimidine-6-carboxylate |
| PT-506 | isopropyl 7-(2-bromobenzo[b]thiophen-3-yl)-5-methyl-4,7-dihydrotetrazolo[1,5-a]pyrimidine-6-carboxylate |
| PT-512 | methyl 5-methyl-7-(naphthalen-1-yl)-4,7-dihydrotetrazolo[1,5-a]pyrimidine-6-carboxylate |
| PT-513 | methyl 5-methyl-7-(thiophen-2-yl)-4,7-dihydrotetrazolo[1,5-a]pyrimidine-6-carboxylate |
| PT-514 | methyl 5-methyl-7-phenyl-4,7-dihydrotetrazolo[1,5-a]pyrimidine-6-carboxylate |
| PT-517 | methyl 7-(2-bromo-5-chlorobenzo[b]thiophen-3-yl)-5-methyl-4,7-dihydrotetrazolo[1,5-a]pyrimidine-6-carboxylate |
| PT-518 | methyl 7-(2-bromobenzo[b]thiophen-3-yl)-5-methyl-4,7-dihydrotetrazolo[1,5-a]pyrimidine-6-carboxylate |
| PT-519 | methyl 7-(2-iodophenyl)-5-methyl-4,7-dihydrotetrazolo[1,5-a]pyrimidine-6-carboxylate |
| PT-520 | methyl 7-(3-bromobenzo[b]thiophen-2-yl)-5-methyl-4,7-dihydrotetrazolo[1,5-a]pyrimidine-6-carboxylate |
| PT-521 | methyl 7-(5-(4-methoxyphenyl)thiophen-2-yl)-5-methyl-4,7-dihydrotetrazolo[1,5-a]pyrimidine-6-carboxylate |
| PT-522 | methyl 7-(5-bromothiophen-2-yl)-5-methyl-4,7-dihydrotetrazolo[1,5-a]pyrimidine-6-carboxylate |
| PT-525 | thiophen-2-ylmethyl 5-methyl-7-(naphthalen-1-yl)-4,7-dihydrotetrazolo[1,5-a]pyrimidine-6-carboxylate |

Given a desired product, such as for example set out in the above table, the necessary starting materials generally may be determined by inspection, based on the general procedure set out in Example 1A.

Example 1D

Preparation of a Compound of Formula (II) Varying R4, R5, R6

Similarly, by essentially following the procedures set out in Examples 1A and 1B above, but optionally replacing the aldehyde (2) with other aldehydes of general formula R$_1$—C(O)H and/or replacing the beta-keto compound (3) with other beta-keto compounds, further compounds of Formula (II) may be prepared.

Example 2

Example 2A

Preparation of Materials

Beta-keto compounds (such as the beta-keto compound (3) in Example 1) used in the synthesis of compounds of the invention typically are either purchased commercially or may be synthesized using known methods. An example of one synthesis is described here:

Synthesis of benzyl 3-oxybutanoate

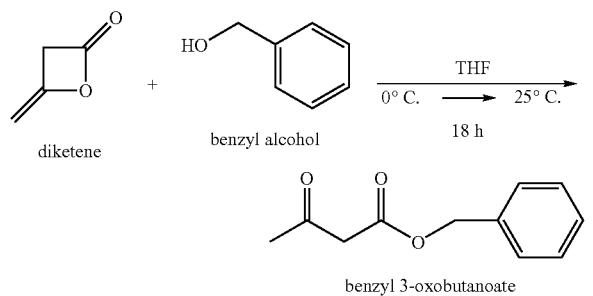

To a solution of benzyl alcohol (50 mmoles) in dry THF (100 ml) cooled to 0° C. was added diketene (50 mmoles) followed by DMAP (2.5 mmoles). The reddish solution is allowed to warm to room temperature in the ice bath over 18 h. The reaction solution is then reduced in vacuo, and ethyl acetate (300 ml) is then added. The organic phase is washed with sodium bicarbonate solution, water, 1M HCl solution, then brine. The organic phase is decanted and reduced in vacuo to provide the beta-ketoester typically as a pinkish oil.

It is noted that various different beta-keto compound products may be obtained by essentially following the procedure set out in this Example above, but optionally replacing the benzyl alcohol with another alcohol (e.g. having the general structure HO—R', where R' may be, e.g. optionally substituted alkyl) or with an amine (e.g. having the general structure H—NR'R", wherein R' and R" may be, e.g. independently hydrogen or optionally substituted alkyl, or R' and R" taken together with the nitrogen may form a heterocyclic ring). If another alcohol is used, the product will be a beta-ketoester; and if an amine is used, the product will be a beta-ketoamide. For example, the benzyl alcohol may be replaced with 4-chlorobenzyl amine, in which case the product of the above reaction is 4-chlorobenzyl 3-oxobutanoate. When preparing beta-ketoamides, DMAP is not necessary and the products are typically solids.

Another example of a synthesis of a beta-keto compound in which the beta-keto compound is a beta-keto hydrazide is given here:

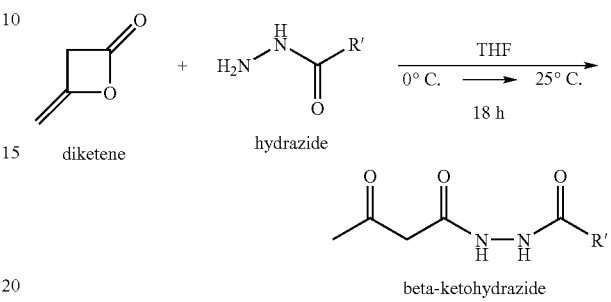

The synthesis for this reaction essentially follows the procedure for synthesis of beta-keto amides as described earlier in this Example, but with the replacement of the amine by the hydrazide. The R' group may be, e.g. optionally substituted lower alkyl, benzyl, phenylethyl, or other substituent group. In the examples herein, Similarly, still other beta-keto compounds (such as the beta-keto compound (3) in Example 1) may be obtained by essentially following the procedure set out in this Example above, but replacing the starting materials with other alcohol, amine, or hydrazide starting materials.

Example 2B

Preparation of Materials

Aldehyde compounds (such as the aldehyde (2) in Example 1) used in the synthesis of compounds of the invention typically are either purchased commercially or may be synthesized using known methods. An example of one synthesis is described here:

Synthesis of 2-(benzyloxy)benzaldehyde

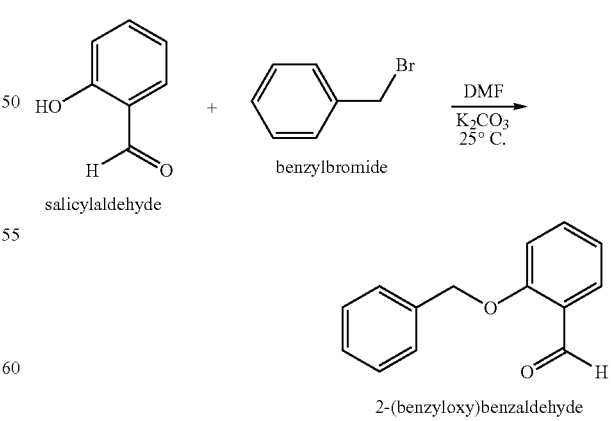

Salicylaldehyde (50 mmoles) was dissolved in dry dimethylformamide (DMF) (100 ml) at room temperature. Benzyl bromide (75 mmoles) was then added followed by the potassium carbonate (125 mmoles) and the mixture stirred at room temperature for 48 h. The mixture is then filtered to remove the potassium carbonate and the filtrate is mixed with ethyl acetate. The organic phase is washed with water (3×200 ml), brine and dried over MgSO$_4$. The solution is then filtered and evaporated in vacuo to provide the crude material. Solid products are washed with ethyl ether to provide the clean desired product or in the case of aldehydes which are oils, they are purified by silica gel chromatography.

It is noted that various different product aldehydes may be obtained by essentially following the procedure set out in this Example above, but optionally replacing the salicylaldehyde with a substituted salicylaldehyde and/or optionally replacing the benzyl bromide with a substituted benzyl bromide. For example, the benzylbromide may be replaced with ethyl 4-(bromomethyl)benzoate, in which case the product of the above reaction is ethyl 4-((2-formylphenoxy)methyl)benzoate. As another example, the salicylaldehyde may be replaced with 5-bromo-2-hydroxybenzaldehyde or 2-hydroxy-4-methoxybenzaldehyde, in which case the product of the above reaction is 2-(benzyloxy)-5-bromobenzaldehyde or 2-(benzyloxy)-4-methoxybenzaldehyde, respectively. Similarly, still other aldehyde products (e.g. compounds of the general formula R$_1$—C(O)H) may be obtained by essentially following the procedure set out in this Example above, but replacing the starting materials with other substituted starting materials.

Example 3

Preparation of a Compound of Formula (II) Varying R4, R5, R6

The variations in the beta-keto compounds and aldehydes described in Examples 2A and 2B, respectively, may be used in the synthesis of compounds of Formula (II) as described in Example 1. By essentially following the procedures set out in Example 1 above, but replacing the aldehyde (2) with other aldehydes of general formula R$_1$—C(O)H (such as described in Example 2B) and/or replacing the beta-keto compound (3) with other beta-keto compounds (such as described in Example 2B) having the necessary substituents to result in the indicated products, the following compounds of Formula (II) were prepared:

TABLE 2

| ID (PT-nnn) | Name of Compound |
| --- | --- |
| PT-268 | 3-((2-(6-(ethoxycarbonyl)-5-methyl-4,7-dihydrotetrazolo[1,5-a]pyrimidin-7-yl)phenoxy)methyl)benzoic acid |
| PT-269 | 3-((3-(6-(ethoxycarbonyl)-5-methyl-4,7-dihydrotetrazolo[1,5-a]pyrimidin-7-yl)phenoxy)methyl)benzoic acid |
| PT-282 | 4-((1H-pyrazol-1-yl)methyl)benzyl 7-(2-(benzyloxy)phenyl)-5-methyl-4,7-dihydrotetrazolo[1,5-a]pyrimidine-6-carboxylate |
| PT-285 | 4-((2-(6-(ethoxycarbonyl)-5-methyl-4,7-dihydrotetrazolo[1,5-a]pyrimidin-7-yl)phenoxy)methyl)benzoic acid |
| PT-286 | 4-((3-(6-(ethoxycarbonyl)-5-methyl-4,7-dihydrotetrazolo[1,5-a]pyrimidin-7-yl)phenoxy)methyl)benzoic acid |
| PT-290 | 4-(2-(5-methyl-7-(naphthalen-1-yl)-4,7-dihydrotetrazolo[1,5-a]pyrimidine-6-carbonyloxy)ethoxy)benzoic acid |
| PT-299 | 4-(6-(benzyloxycarbonyl)-5-methyl-4,7-dihydrotetrazolo[1,5-a]pyrimidin-7-yl)benzoic acid |
| PT-377 | benzyl 7-(2-(4-(ethoxycarbonyl)benzyloxy)phenyl)-5-methyl-4,7-dihydrotetrazolo[1,5-a]pyrimidine-6-carboxylate |
| PT-380 | benzyl 7-(2-(benzyloxy)-4-methoxyphenyl)-5-methyl-4,7-dihydrotetrazolo[1,5-a]pyrimidine-6-carboxylate |
| PT-381 | benzyl 7-(2-(benzyloxy)-5-bromophenyl)-5-methyl-4,7-dihydrotetrazolo[1,5-a]pyrimidine-6-carboxylate |
| PT-382 | benzyl 7-(2-(benzyloxy)-6-methoxyphenyl)-5-methyl-4,7-dihydrotetrazolo[1,5-a]pyrimidine-6-carboxylate |
| PT-383 | benzyl 7-(2-(benzyloxy)phenyl)-5-methyl-4,7-dihydrotetrazolo[1,5-a]pyrimidine-6-carboxylate |
| PT-480 | ethyl 7-(2-(3-(methoxycarbonyl)benzyloxy)phenyl)-5-methyl-4,7-dihydrotetrazolo[1,5-a]pyrimidine-6-carboxylate |
| PT-482 | ethyl 7-(2-(4-(ethoxycarbonyl)benzyloxy)phenyl)-5-methyl-4,7-dihydrotetrazolo[1,5-a]pyrimidine-6-carboxylate |
| PT-495 | ethyl 7-(3-(3-(methoxycarbonyl)benzyloxy)phenyl)-5-methyl-4,7-dihydrotetrazolo[1,5-a]pyrimidine-6-carboxylate |
| PT-497 | ethyl 7-(3-(4-(ethoxycarbonyl)benzyloxy)phenyl)-5-methyl-4,7-dihydrotetrazolo[1,5-a]pyrimidine-6-carboxylate |
| PT-516 | methyl 7-(2-(4-(ethoxycarbonyl)benzyloxy)phenyl)-5-methyl-4,7-dihydrotetrazolo[1,5-a]pyrimidine-6-carboxylate |

Example 4

Example 4A

General Method for Synthesis of Compounds of Formula (III)

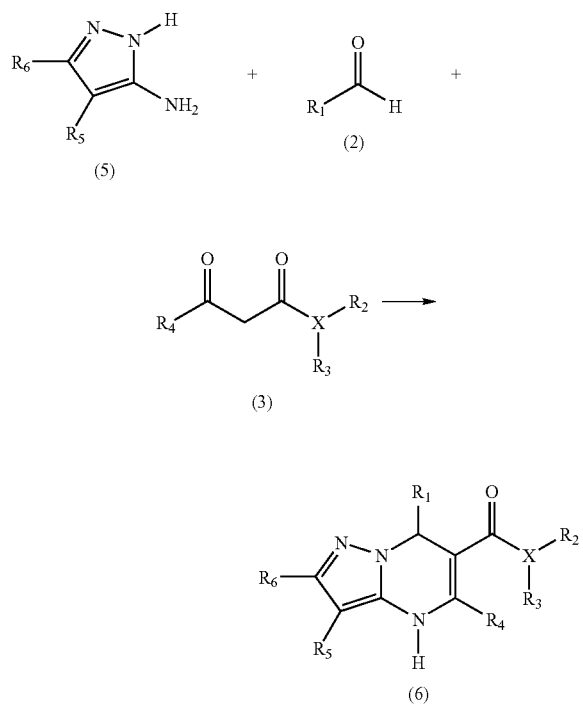

Referring to the above reaction, the aminopyrazole (5) is reacted with an aldehyde (2) and a beta-keto compound (3) to give the product (6), which is a compound of Formula (III). Given a desired product (6) for which the substituent groups $R_1$, $X(R_2)(R_3)$, $R_4$, $R_5$ and $R_6$ are defined, the necessary starting materials (2), (3) and (5) may be determined by inspection. In certain cases, X is a nitrogen and $R_2$ and $R_3$ may be substituents (such as are described elsewhere herein) bound to the nitrogen, such that the beta-keto compound (3) is a beta-keto amide. In certain other cases, X taken together with $R_3$ is an oxygen and $R_2$ may be a substituent (such as described elsewhere herein) bound to the oxygen, such that the beta-keto compound (3) is a beta-keto ester.

To a solution of the aminopyrazole (5) (10.0 mmole) and triethylamine (1.8 mmole) in hot ethanol (15 ml) was added the aldehyde (2) (10.0 mmole) followed by the beta-keto compound (3) (10.0 mmole). The solution was maintained at reflux for 15 h. In cases in which a precipitate formed, the mixture was cooled to room temperature, and the mixture was filtered and washed with ethanol and ethyl ether to provide the desired product (6). In cases in which no precipitate formed in the flask, the mixture was cooled to room temperature and the ethanol stripped in vacuo, and the crude viscous material was purified on a 150 g $SiO_2$ flash column using 30% ethyl acetate:hexanes as eluent. The purified material was washed with a 1:1 mixture of ethyl ether and hexanes in a filter funnel to provide the desired product (6).

Example 4B

Preparation of a Compound of Formula (III) in which R4 is Napthyl, R5 is Ethoxy, and R6 is Methyl Synthesis of ethyl 3-cyano-5-methyl-7-(naphthalen-1-yl)-4,7-dihydropyrazolo[1,5-a]pyrimidine-6-carboxylate (PT-091)

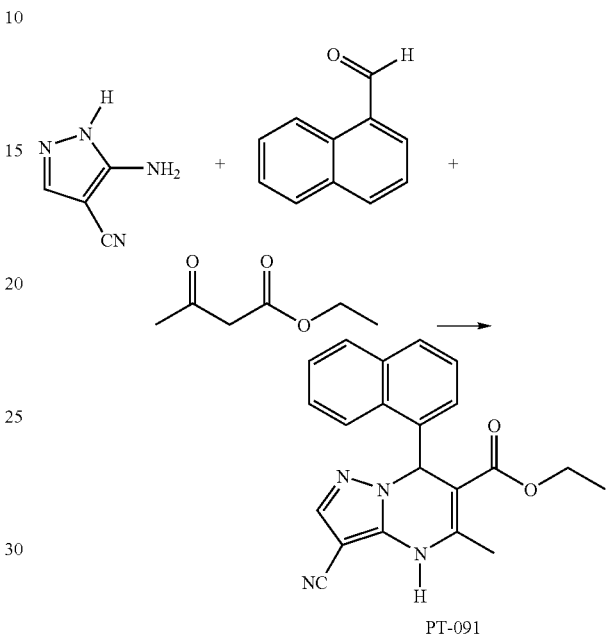

To a solution of 2-amino-3-cyano-1H-pyrazole (1.08 g, 10.0 mmole) and triethylamine (0.25 ml, 1.8 mmole) in hot ethanol (15 ml) was added 1-naphthaldehyde (1.36 ml, 10.0 mmole) followed by ethylacetoacetate (1.28 ml, 10.0 mmole). The solution was maintained at reflux for 15 h. No precipitate had formed in the flask. The mixture was cooled to room temperature and the ethanol stripped in vacuo. The crude viscous material was purified on a 150 g $SiO_2$ flash column using 30% ethyl acetate:hexanes as eluent. The purified material was washed with a 1:1 mixture of ethyl ether and hexanes in a filter funnel to provide the desired product (0.422 mg, 12%) as a white powder. $^1H$ NMR (400 MHz; DMSO-d6) d 10.90 (bs, 1H); 8.6 (d, 1H, J=8.6 Hz); 7.94 (d, 1H, J=8.2 Hz); 7.86 (d, 1H, J=7.4 Hz); 7.72 (s, 1H); 7.64 (at, 1H, J=7.0 Hz); 7.56 (at, 1H, J=7.4 Hz); 7.46 (at, 1H, J=7.4 Hz); 7.4 (bd, 1H, J=6.3 Hz); 3.76 (q, 2H, J=7.0 Hz); 2.54 (s, 3H); 0.67 (t, 3H, J=7.0 Hz). LC MS shows MH+ at 359; M+Na at 381 and 2M+Na at 739.

Example 4C

Preparation of a Compound of Formula (III) Varying R4 and R5

Similarly, by essentially following the procedures set out in Examples 4A and 4B above, but optionally replacing the aminopyrazole (5) with other aminopyrazoles having the general structure (5) set out in Example 4A, and/or optionally replacing the aldehyde (2) with other aldehydes of general formula $R_1$—C(O)H, and/or replacing the beta-keto compound (3) with other beta-keto compounds (e.g. acetoacetate or acetoacetamide) having the necessary substituents to result in the indicated products, the following compounds of Formula (III) were prepared:

TABLE 3

| ID (PT-nnn) | Name of Compound |
|---|---|
| PT-091 | ethyl 3-cyano-5-methyl-7-(naphthalen-1-yl)-4,7-dihydropyrazolo[1,5-a]pyrimidine-6-carboxylate |
| PT-244 | (S)-1-phenylethyl 5-methyl-7-(3-methylbenzo[b]thiophen-2-yl)-4,7-dihydropyrazolo[1,5-a]pyrimidine-6-carboxylate |
| PT-311 | 6-(benzyloxycarbonyl)-7-(4-(dimethylamino)naphthalen-1-yl)-5-methyl-4,7-dihydropyrazolo[1,5-a]pyrimidine-3-carboxylic acid |
| PT-312 | 6-(benzyloxycarbonyl)-7-(4-methoxynaphthalen-1-yl)-5-methyl-4,7-dihydropyrazolo[1,5-a]pyrimidine-3-carboxylic acid |
| PT-362 | benzyl 5-methyl-7-(naphthalen-1-yl)-3-phenyl-4,7-dihydropyrazolo[1,5-a]pyrimidine-6-carboxylate |
| PT-363 | benzyl 5-methyl-7-(thiazol-2-yl)-4,7-dihydropyrazolo[1,5-a]pyrimidine-6-carboxylate |
| PT-394 | benzyl 7-(2-methoxy-4-nitrophenyl)-5-methyl-4,7-dihydropyrazolo[1,5-a]pyrimidine-6-carboxylate |
| PT-463 | ethyl 5-methyl-7-(3-phenoxyphenyl)-4,7-dihydropyrazolo[1,5-a]pyrimidine-6-carboxylate |
| PT-478 | ethyl 7-(2-(2-(dimethylamino)ethoxy)phenyl)-5-methyl-4,7-dihydropyrazolo[1,5-a]pyrimidine-6-carboxylate |
| PT-488 | ethyl 7-(2-bromobenzo[b]thiophen-3-yl)-5-methyl-4,7-dihydropyrazolo[1,5-a]pyrimidine-6-carboxylate |
| PT-491 | ethyl 7-(2-cyano-4-methoxyphenyl)-5-methyl-4,7-dihydropyrazolo[1,5-a]pyrimidine-6-carboxylate |
| PT-502 | ethyl 7-(4-(dimethylamino)naphthalen-1-yl)-5-methyl-4,7-dihydropyrazolo[1,5-a]pyrimidine-6-carboxylate |
| PT-507 | methyl 2,5-dimethyl-7-(4-methylthiazol-2-yl)-4,7-dihydropyrazolo[1,5-a]pyrimidine-6-carboxylate |
| PT-508 | methyl 2,5-dimethyl-7-(naphthalen-1-yl)-4,7-dihydropyrazolo[1,5-a]pyrimidine-6-carboxylate |
| PT-511 | methyl 5-methyl-7-(4-methylthiazol-2-yl)-4,7-dihydropyrazolo[1,5-a]pyrimidine-6-carboxylate |

Given a desired product, such as for example set out in the above table, the necessary starting materials generally may be determined by inspection, based on the general procedure set out in Example 4A.

Example 4D

Preparation of a Compound of Formula (III) Varying R4 and R5

Similarly, by essentially following the procedures set out in Examples 4A and 4B above, but optionally replacing the aminopyrazole (5) with other aminopyrazoles having the general structure (5) set out in Example 4A, and/or optionally replacing the aldehyde (2) with other aldehydes of general formula $R_1$—C(O)H and/or replacing the beta-keto compound (3) with other beta-keto compounds, further compounds of Formula (III) may be prepared.

Example 5

Example 5A

General Method for Synthesis of Compounds of Formula (IV)

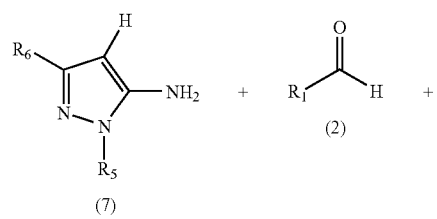

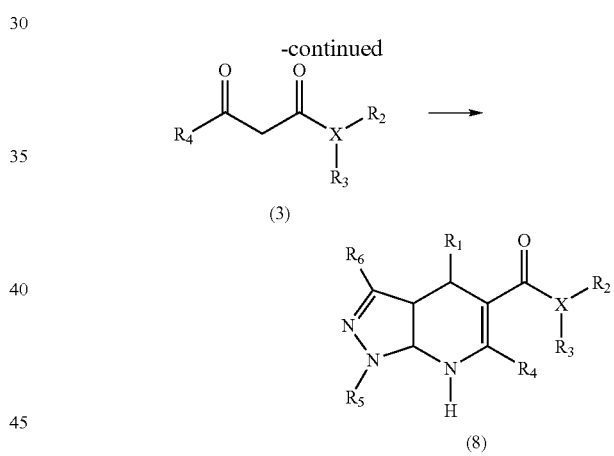

Referring to the above reaction, the aminopyrazole (7) is reacted with an aldehyde (2) and a beta-keto compound (3) to give the product (8), which is a compound of Formula (IV). Given a desired product (8) for which the substituent groups $R_1$, $X(R_2)(R_3)$, $R_4$, $R_5$ and $R_6$ are defined, the necessary starting materials (2), (3) and (7) may be determined by inspection. In certain cases, X is a nitrogen and $R_2$ and $R_3$ may be substituents (such as are described elsewhere herein) bound to the nitrogen, such that the beta-keto compound (3) is a beta-keto amide. In certain other cases, X taken together with $R_3$ is an oxygen and $R_2$ may be a substituent (such as described elsewhere herein) bound to the oxygen, such that the beta-keto compound (3) is a beta-keto ester.

To a solution of the amino-substituted pyrazole (7) (10.0 mmole) and triethylamine (1.8 mmole) in hot ethanol (20 ml) was added the aldehyde (2) (10.0 mmole) followed by the beta-keto compound (3) (e.g. acetoacetate or acetoacetamide) (10.0 mmole). The mixture was heated at reflux for 15 h. A precipitate is usually observed and upon cooling the mixture to room temperature, it is filtered and washed with ethanol then ethyl ether to provide the desired product as a white powder. Yields can vary between 5-90% depending upon substituents of the aldehyde (2) and the beta-keto compound (3).

Example 5B

Preparation of a Compound of Formula (IV) in which R4 is 4-methylthiazol-2-yl, R5 is Methoxy, and R6 is Methyl

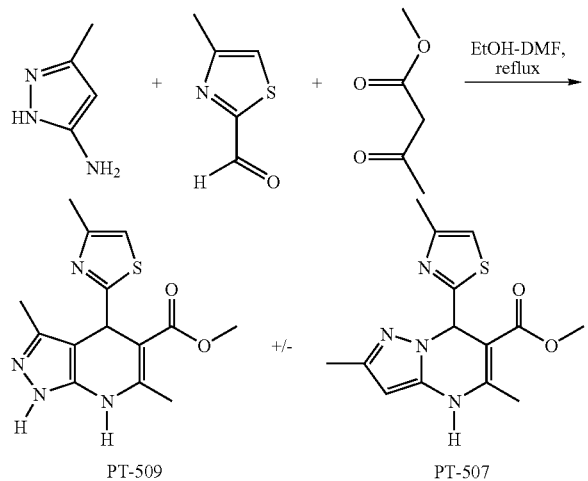

Procedure: To a mixture of 3-methyl-1H-pyrazol-5-amine (527 mg, 5.42 mmol) and absolute ethanol (EtOH) (8 ml) and DMF (2 mL) was added compound 4-methylthiazole-2-carbaldehyde (690 mg, 5.42 mmol), and then methyl acetoacetate (756 mg, 6.51 mmol). The whole mixture was heated to reflux. In 18 h, the mixture was cooled to room temperature and concentrated to give an orange slurry. LCMS showed only 2 isomers with the same m/z in MS at a ratio of 1.1:1.0 (PT-509:PT507). DMF (3 mL) was added, the reaction mixture was subjected to preparative HPLC with a gradient of MeCN/H$_2$O (5% to 98%) to afford PT-509 (710 mg, 2.33 mmol, 43%). MS m/z 305.1 (M+H), HPLC 92% pure. $^1$H NMR (400 MHz; DMSO-D$_6$) 6.91 (s, 1H); 5.39 (s, 1H); 3.57 (s, 1H); 3.50 (s, 1H); 3.47 (s, 3H); 2.39 (s, 3H); 2.28 (s, 3H); 2.20 (s, 3H).

The reaction also afforded PT-507 (544 mg, 1.79 mmol, 33%). MS m/z 305.1 (M+H), HPLC>98%. $^1$H NMR (400 MHz; DMSO-D$_6$) 7.13 (s, 1H); 6.38 (s, 1H); 5.50 (s, 1H); 3.56 (s, 3H); 2.40 (s, 3H); 2.84 (s, 3H); 2.07 (s, 3H).

Example 5C

Preparation of Compounds of Formula (IV) in which R4 is Naphthyl and R5 and R6 Together Form a Bridging Group In a variation of the synthesis described in Examples 5A and 5B, the beta-keto compound is a cyclic compound, such as a cyclic amide or cyclic ester. The final product is a compound of Formula (IV) in which R5 and R6 taken together form a bridging group, such as —O—CH$_2$— (as shown below). The synthesis of one such compound is described here.

Synthesis of p-toluyl-7,8-dihydro-1H-furo[3,4-e]pyrazolo[3,4-b]pyridin-5(4H)-one (PT-078)

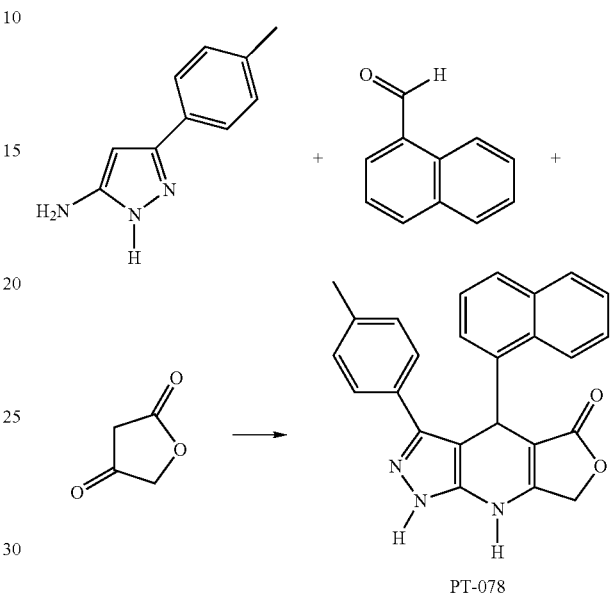

To a solution of 1H-2-amino-4-toluylpyrazole (866 mg, 5.0 mmole) in ethanol (15 ml) at 82° C. was added triethylamine (0.2 ml, 1.4 mmole) followed by 1-naphthaldehyde (0.682 ml, 5.0 mmole) and then tetronic acid (0.50 g, 5.0 mmole). The clear solution mixture was maintained at reflux for 15 h. A precipitate had formed and the mixture was cooled to room temperature. The mixture was filtered and washed with ethanol and ethyl ether to provide the desired product (0.554 g, 28%) as a light yellow powder. powder. $^1$H NMR (400 MHz; DMSO-d6) d 12.5 (bs, 1H); 10.4 (bs, 1H); 7.82 (d, 1H, J=9.3 Hz); 7.65 (d, 1H, J=9.0 Hz); 7.55-7.40 (bs, m, 2H); 7.32 (at, 1H, J=7.4 Hz); 7.20-7.15 (m, 3H); 6.95-6.80 bs, m, 2H); 6.0 (bs, 1H); 4.86 (s, 2H); 2.11 (s, 3H). LC MS shows MH+ at 394 and 2 MH+ at 787.

Example 5D

Preparation of a Compound of Formula (IV) Varying R4 and R5

Similarly, by essentially following the procedures set out in Examples 5A, 5B and 5C above, but optionally replacing the aminopyrazole (7) with other aminopyrazoles having the general structure (7) set out in Example 5A, and/or optionally replacing the aldehyde (2) with other aldehydes of general formula R$_1$—C(O)H, and/or replacing the beta-keto compound (3) with other beta-keto compounds (e.g. acetoacetate or acetoacetamide or cyclic amide or cyclic ester) having the necessary substituents to result in the indicated products, the following compounds of Formula (IV) were prepared:

TABLE 4

| ID (PT-nnn) | Name of Compound |
|---|---|
| PT-073 | ethyl 6-methyl-4-(naphthalen-1-yl)-3-p-tolyl-4,7-dihydro-1H-pyrazolo[3,4-b]pyridine-5-carboxylate |
| PT-074 | ethyl 3,6-dimethyl-4-(naphthalen-1-yl)-4,7-dihydro-1H-pyrazolo[3,4-b]pyridine-5-carboxylate |
| PT-075 | ethyl 6-methyl-4-(naphthalen-1-yl)-4,7-dihydro-1H-pyrazolo[3,4-b]pyridine-5-carboxylate |
| PT-076 | benzyl 6-methyl-4-(naphthalen-1-yl)-3-(thiophen-2-yl)-4,7-dihydro-1H-pyrazolo[3,4-b]pyridine-5-carboxylate |
| PT-077 | benzyl 6-methyl-4-(naphthalen-1-yl)-3-p-tolyl-4,7-dihydro-1H-pyrazolo[3,4-b]pyridine-5-carboxylate |
| PT-078 | p-tolyl-7,8-dihydro-1H-furo[3,4-e]pyrazolo[3,4-b]pyridin-5(4H)-one |
| PT-079 | H-furo[3,4-e]pyrazolo[3,4-b]pyridin-5(4H)-one |
| PT-080 | 3-(furan-2-yl)-4-(naphthalen-1-yl)-7,8-dihydro-1H-furo[3,4-e]pyrazolo[3,4-b]pyridin-5(4H)-one |
| PT-081 | 3-methyl-4-(naphthalen-1-yl)-7,8-dihydro-1H-furo[3,4-e]pyrazolo[3,4-b]pyridin-5(4H)-one |
| PT-082 | 4-(naphthalen-1-yl)-1-phenyl-7,8-dihydro-1H-furo[3,4-e]pyrazolo[3,4-b]pyridin-5(4H)-one |
| PT-083 | 3-methyl-4-(naphthalen-1-yl)-1-phenyl-7,8-dihydro-1H-furo[3,4-e]pyrazolo[3,4-b]pyridin-5(4H)-one |
| PT-084 | 4-(naphthalen-1-yl)-7,8-dihydro-1H-furo[3,4-e]pyrazolo[3,4-b]pyridin-5(4H)-one |
| PT-085 | methyl 4-(4-(naphthalen-1-yl)-5-oxo-4,5,7,8-tetrahydro-1H-furo[3,4-b]pyrazolo[4,3-e]pyridin-3-yl)benzoate |
| PT-263 | 2-methyl-1-phenylpropan-2-yl 4-(2-bromophenyl)-6-methyl-4,7-dihydro-1H-pyrazolo[3,4-b]pyridine-5-carboxylate |
| PT-301 | 4-(naphthalen-1-yl)-1H-furo[3,4-e]pyrazolo[3,4-b]pyridin-5(7H)-one |
| PT-302 | 4-(naphthalen-1-yl)-1-phenyl-1H-furo[3,4-e]pyrazolo[3,4-b]pyridin-5(7H)-one |
| PT-325 | benzyl 3,6-dimethyl-4-(naphthalen-2-yl)-4,7-dihydro-1H-pyrazolo[3,4-b]pyridine-5-carboxylate |
| PT-327 | benzyl 4-(2-((R)-3-(ethoxycarbonyl)piperidin-1-yl)-4-methoxyphenyl)-6-methyl-4,7-dihydro-1H-pyrazolo[3,4-b]pyridine-5-carboxylate |
| PT-330 | benzyl 4-(2-bromophenyl)-6-methyl-4,7-dihydro-1H-pyrazolo[3,4-b]pyridine-5-carboxylate |
| PT-332 | benzyl 4-(4-(dimethylamino)naphthalen-1-yl)-6-methyl-4,7-dihydro-1H-pyrazolo[3,4-b]pyridine-5-carboxylate |
| PT-333 | benzyl 4-(4-methoxynaphthalen-1-yl)-6-methyl-4,7-dihydro-1H-pyrazolo[3,4-b]pyridine-5-carboxylate |
| PT-367 | benzyl 6-methyl-4-(naphthalen-1-yl)-4,7-dihydro-1H-pyrazolo[3,4-b]pyridine-5-carboxylate |
| PT-368 | benzyl 6-methyl-4-(naphthalen-2-yl)-4,7-dihydro-1H-pyrazolo[3,4-b]pyridine-5-carboxylate |
| PT-369 | benzyl 6-methyl-4-(thiazol-2-yl)-4,7-dihydro-1H-pyrazolo[3,4-b]pyridine-5-carboxylate |
| PT-370 | benzyl 6-methyl-4-(thiophen-2-yl)-4,7-dihydro-1H-pyrazolo[3,4-b]pyridine-5-carboxylate |
| PT-372 | benzyl 6-methyl-4-phenyl-4,7-dihydro-1H-pyrazolo[3,4-b]pyridine-5-carboxylate |
| PT-440 | ethyl 1,3,6-trimethyl-4-(naphthalen-1-yl)-4,7-dihydro-1H-pyrazolo[3,4-b]pyridine-5-carboxylate |
| PT-443 | ethyl 3,6-dimethyl-4-(thiophen-2-yl)-4,7-dihydro-1H-pyrazolo[3,4-b]pyridine-5-carboxylate |
| PT-445 | ethyl 4-(2-(benzyloxy)-4-methoxyphenyl)-6-methyl-4,7-dihydro-1H-pyrazolo[3,4-b]pyridine-5-carboxylate |
| PT-446 | ethyl 4-(2,6-dimethoxyphenyl)-6-methyl-4,7-dihydro-1H-pyrazolo[3,4-b]pyridine-5-carboxylate |
| PT-447 | ethyl 4-(2-bromobenzo[b]thiophen-3-yl)-6-methyl-4,7-dihydro-1H-pyrazolo[3,4-b]pyridine-5-carboxylate |
| PT-448 | ethyl 4-(2-bromophenyl)-6-methyl-4,7-dihydro-1H-pyrazolo[3,4-b]pyridine-5-carboxylate |
| PT-454 | ethyl 4-(4-(dimethylamino)naphthalen-1-yl)-6-methyl-4,7-dihydro-1H-pyrazolo[3,4-b]pyridine-5-carboxylate |
| PT-470 | ethyl 6-methyl-4-(3-phenoxyphenyl)-4,7-dihydro-1H-pyrazolo[3,4-b]pyridine-5-carboxylate |
| PT-473 | ethyl 6-methyl-4-(thiophen-2-yl)-4,7-dihydro-1H-pyrazolo[3,4-b]pyridine-5-carboxylate |
| PT-509 | methyl 3,6-dimethyl-4-(4-methylthiazol-2-yl)-4,7-dihydro-1H-pyrazolo[3,4-b]pyridine-5-carboxylate |
| PT-510 | methyl 4-(2,4-dichlorothiazol-5-yl)-6-methyl-4,7-dihydro-1H-pyrazolo[3,4-b]pyridine-5-carboxylate |
| PT-515 | methyl 6-methyl-4-(4-methylthiazol-2-yl)-4,7-dihydro-1H-pyrazolo[3,4-b]pyridine-5-carboxylate |
| PT-523 | S)-1-phenylethyl 6-methyl-4-(3-methylbenzo[b]thiophen-2-yl)-4,7-dihydro-1H-pyrazolo[3,4-b]pyridine-5-carboxylate |

Given a desired product, such as for example set out in the above table, the necessary starting materials generally may be determined by inspection, based on the general procedure set out in Example 5A.

Example 5E

Preparation of a Compound of Formula (IV) Varying R4, R5, R6

Similarly, by essentially following the procedures set out in Examples 5A, 5B and 5C above, but optionally replacing the aminopyrazole (7) with other aminopyrazoles having the general structure (7) set out in Example 5A, and/or optionally replacing the aldehyde (2) with other aldehydes of general formula $R_1$—C(O)H and/or replacing the beta-keto compound (3) with other beta-keto compounds (e.g. acetoacetate or acetoacetamide or cyclic amide or cyclic ester), further compounds of Formula (IV) may be prepared.

Example 6

Example 6A

General Method for Synthesis of Compounds of Formula (V)

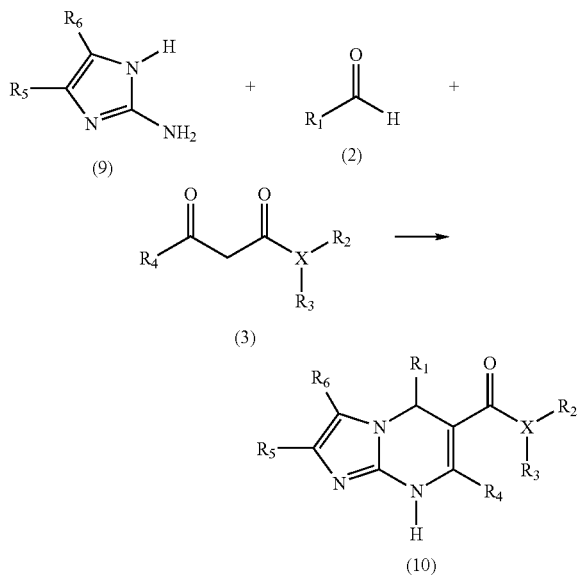

Referring to the above reaction, the 2-aminoimidazole (9) is reacted with an aldehyde (2) and a beta-keto compound (3) to give the product (10), which is a compound of Formula (V). Given a desired product (10) for which the substituent groups $R_1$, $X(R_2)(R_3)$, $R_4$, $R_5$ and $R_6$ are defined, the necessary starting materials (2), (3) and (9) may be determined by inspection. In certain cases, X is a nitrogen and $R_2$ and $R_3$ may be substituents (such as are described elsewhere herein) bound to the nitrogen, such that the beta-keto compound (3) is a beta-keto amide. In certain other cases, X taken together with $R_3$ is an oxygen and $R_2$ may be a substituent (such as described elsewhere herein) bound to the oxygen, such that the beta-keto compound (3) is a beta-keto ester.

To a solution of 2-aminoimidazole (10.0 mmole) and triethylamine (10.0 mmole) in hot ethanol (20 ml) was added the aldehyde (2) (10.0 mmole) followed by the beta-keto compound (10.0 mmole). The solution was maintained at reflux for 15 h. A white precipitate is usually observed in the flask. The mixture was cooled to room temperature, filtered and washed consecutively with ethanol, ethyl acetate then ethyl ether to provide the desired product (10) as a white powder.

Example 6B

Preparation of a Compound of Formula (V) in which R4 is Napthyl, R5 is Benzyloxy, and R6 is Methyl Synthesis of benzyl 7-methyl-5-(naphthalen-1-yl)-5,8-dihydroimidazo[1,2-a]pyrimidine-6-carboxylate (PT-088)

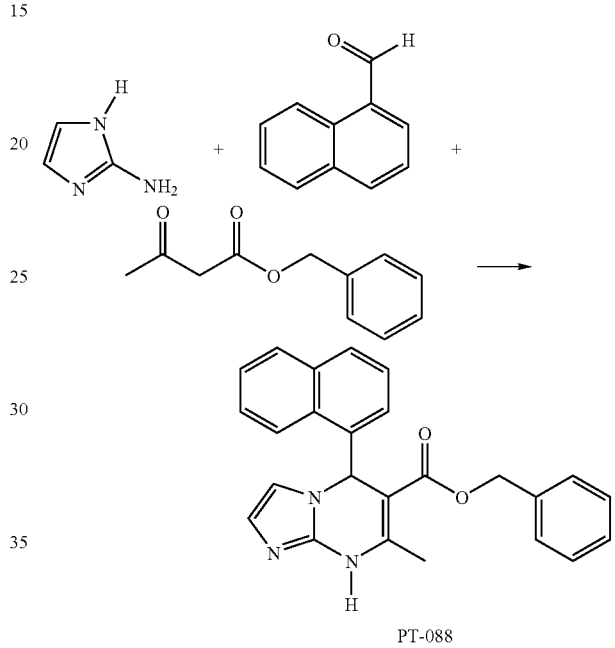

PT-088

To a solution of 2-aminoimidazole-1/2H$_2$SO$_4$ (1.32 g, 10.0 mmole) and triethylamine (1.4 ml, 10.0 mmole) in hot ethanol (20 ml) was added 1-naphthaldehyde (1.36 ml, 10.0 mmole) followed by benzylacetoacetate (1.72 ml, 10.0 mmole). The solution is maintained at reflux for 15 h. A white precipitate had formed in the flask. The mixture was cooled to room temperature, filtered and washed consecutively with ethanol, ethyl acetate then ethyl ether to provide the desired product (0.883 g, 22%) as a white powder. $^1$H NMR (400 MHz; CDCl$_3$) d 8.32 (bs, 1H); 7.88 (m, 1H); 7.76 (d, 1H, J=7.8 Hz); 7.54 (d, 1H, J=7.0 Hz); 7.48 (m, 2H); 7.37 (at, 1H, J=7.8 Hz); 7.13 (m, 2H); 7.04 (at, 1H, J=7.8 Hz); 6.7 (ad, 2H, J=7.0 Hz); 6.63 (d, 1H, J=1.5 Hz); 6.43 (d, 1H, J=1.1 Hz). LC MS shows MH+ at 396.

Example 6C

Preparation of a Compound of Formula (V) Varying R4 and R5

Similarly, by essentially following the procedures set out in Examples 6A and 6B above, but optionally replacing the 2-aminoimidazole (9) with other 2-aminoimidazoles having the general structure (9) set out in Example 6A, and/or optionally replacing the aldehyde (2) with other aldehydes of general formula $R_1$—C(O)H, and/or replacing the beta-keto compound (3) with other beta-keto compounds (e.g. acetoacetate or acetoacetamide) having the necessary substituents to result in the indicated products, the following compounds of Formula (V) were prepared:

TABLE 5

| ID (PT-nnn) | Name of Compound |
|---|---|
| PT-086 | ethyl 7-methyl-5-(naphthalen-2-yl)-5,8-dihydroimidazo[1,2-a]pyrimidine-6-carboxylate |
| PT-087 | ethyl 7-methyl-5-(naphthalen-1-yl)-5,8-dihydroimidazo[1,2-a]pyrimidine-6-carboxylate |
| PT-088 | benzyl 7-methyl-5-(naphthalen-1-yl)-5,8-dihydroimidazo[1,2-a]pyrimidine-6-carboxylate |
| PT-194 | ethyl 2,3-dicyano-7-methyl-5-(naphthalen-1-yl)-5,8-dihydroimidazo[1,2-a]pyrimidine-6-carboxylate |

Given a desired product, such as for example set out in the above table, the necessary starting materials generally may be determined by inspection, based on the general procedure set out in Example 6A.

Example 6D

Preparation of a Compound of Formula (V) Varying R4 and R5

Similarly, by essentially following the procedures set out in Examples 6A and 6B above, but optionally replacing the 2-aminoimidazole (9) with other 2-aminoimidazoles having the general structure (9) set out in Example 6A, and/or optionally replacing the aldehyde (2) with other aldehydes of general formula $R_1$—C(O)H and/or replacing the beta-keto compound (3) with other beta-keto compounds, further compounds of Formula (V) may be prepared.

Example 7

Example 7A

General Method for Synthesis of Compounds of Formula (VI)

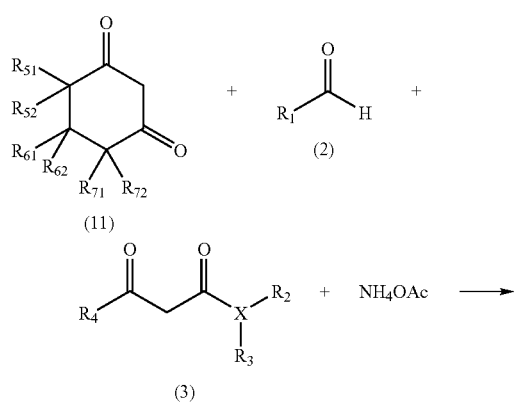

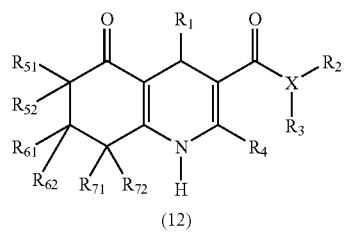

Referring to the above reaction, the 1,3-cyclohexanedione (11) is reacted with an aldehyde (2) and a beta-keto compound (3) to give the product (12), which is a compound of Formula (VI). Given a desired product (12) for which the substituent groups $R_1$, $X(R_2)(R_3)$, $R_4$, $R_{51}$, $R_{52}$, $R_{61}$, $R_{62}$, $R_{71}$, $R_{72}$, are defined, the necessary starting materials (2), (3) and (11) may be determined by inspection. In certain cases, X is a nitrogen and $R_2$ and $R_3$ may be substituents (such as are described elsewhere herein) bound to the nitrogen, such that the beta-keto compound (3) is a beta-keto amide. In certain other cases, X taken together with $R_3$ is an oxygen and $R_2$ may be a substituent (such as described elsewhere herein) bound to the oxygen, such that the beta-keto compound (3) is a beta-keto ester.

To a solution of the 1,3-cyclohexanedione (11) (10.0 mmole) in hot ethanol (20 ml) was added the aldehyde (2) (10.0 mmole) then the beta-keto compound (3) (10.0 mmole) (e.g. beta-keto ester or beta-keto amide) followed by the ammonium acetate (20.0 mmole). The mixture is heated at reflux for 15 h and then reduced in vacuo. The mixture is taken up in ethyl acetate and washed with water (2×), saturated aqueous $NaHCO_3$ then brine. The organic phase is dried over $MgSO_4$, filtered then reduced in vacuo. The material is either taken up in ethyl acetate or ethyl ether and crystallization is initiated with scratching or letting the solution sit overnight at room temperature. If the above procedure does not work, the material is purified on a silica gel flash column to provide the purified desired product.

It is noted that essentially the same reaction may be performed, but substituting a 1,3-cyclopentanedione (13) and ending with the product (14), as shown here:

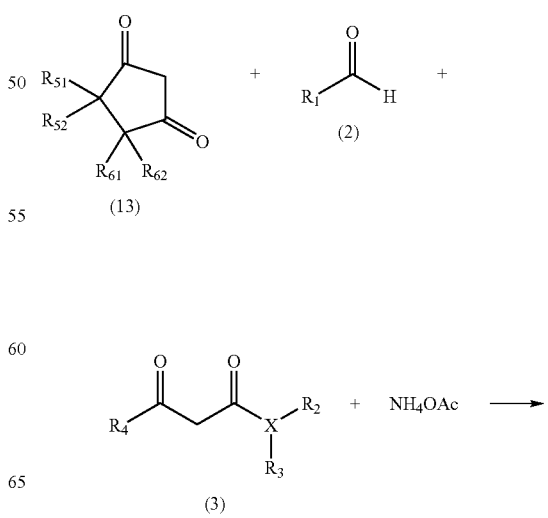

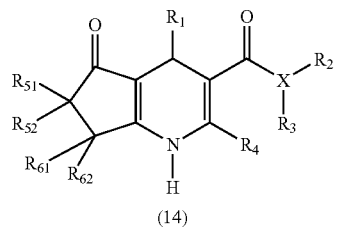

(14)

Thus, compounds of the invention having the structure given by Formula (VI) wherein R24" is a bond may be synthesized as described in this example.

Example 7B

Preparation of a Compound of Formula (VI) in which R4 is 5-phenylthiophen-2-yl, R5 is Ethoxy, and R6 is Propyl Synthesis of ethyl 7,7-dimethyl-5-oxo-4-(5-phenylthiophen-2-yl)-2-propyl-1,4,5,6,7,8-hexahydroquinoline-3-carboxylate (PT-141)

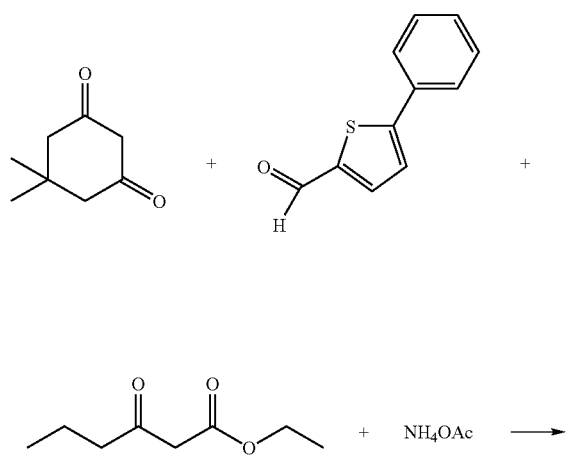

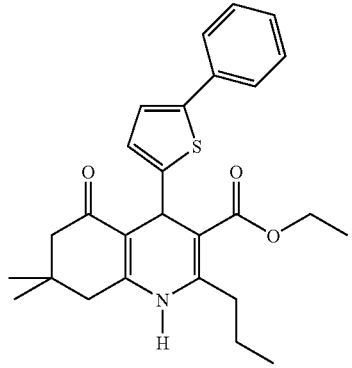

PT-141

To a solution of dimedone (0.70 g, 5.0 mmole) in hot ethanol (15 ml) was added 5-phenyl-2-thiophenecarboxaldehyde (0.940 g, 5.0 mmole), ethyl propylacetoacetate (0.80 ml, 5.0 mmole) and lastly ammonium acetate (0.770 g, 10.0 mmole). The mixture was held at reflux for 48 h. No precipitate was observed. The ethanol was removed in vacuo to provide a crude viscous material which was subjected to a 100 g $SiO_2$ flash column using 40% ethyl acetate:hexanes as eluent. The desired product (1.54 g, 68%) was obtained as a yellow amorphous solid. Rf=0.37 in 1:1 ethyl acetate hexanes. $^1$H NMR (400 MHz; $CDCl_3$) d 7.5 (bd, 2H, J=7.0 Hz); 7.32-7.25 (m, 2H); 7.19 (at, 1H, J=7.4 Hz); 7.04 (d, 1H, J=7.4 Hz); 6.8 (d, 1H, J=3.5 Hz); 6.38 (bs, 1H); 5.41 (s, 1H); 4.22-3.90 (m, 2H); 2.90-2.80 (m, 1H); 2.72-2.63 (m, 1H); 2.35 (d, 1H, J=16.8 Hz); 2.25 (d, 1H, J=16.8 Hz); 2.3-2.2 (On, 2H); 1.74-1.62 (m, 2H); 1.25 (at, 3H, J=7.0 Hz); 1.07 (s, 3H); 1.02 (s, 3H); 1.01 (at, 3H, J=7.0 Hz); 1.05-0.95 (m, 2H). LC MS shows MH+ at 450; 2M+H at 899 and 2M+Na at 921.

Example 7C

Preparation of a Compound of Formula (VI) Varying R4, R5, R6, R24"

Similarly, by essentially following the procedures set out in Examples 7A and 7B above, but optionally replacing the 1,3-cyclohexanedione (11) with another 1,3-cyclohexanedione having the general structure (11) set out in Example 7A (or replacing it with a 1,3-cyclopentanedione having the general structure (13), as explained at the end of Example 7A), and/or optionally replacing the aldehyde (2) with other aldehydes of general formula $R_1$—C(O)H, and/or replacing the beta-keto compound (3) with other beta-keto compounds (e.g. acetoacetate or acetoacetamide) having the necessary substituents to result in the indicated products, the following compounds of Formula (VI) were prepared:

TABLE 6

| ID (PT-nnn) | Name of Compound |
|---|---|
| PT-131 | ethyl 4-(biphenyl-4-yl)-2,7,7-trimethyl-5-oxo-1,4,5,6,7,8-hexahydroquinoline-3-carboxylate |
| PT-132 | 3-(3-(ethoxycarbonyl)-2,7,7-trimethyl-5-oxo-1,4,5,6,7,8-hexahydroquinolin-4-yl)benzoic acid |
| PT-134 | ethyl 4-(2-methoxynaphthalen-1-yl)-2-methyl-5-oxo-1,4,5,6,7,8-hexahydroquinoline-3-carboxylate |
| PT-135 | ethyl 2-methyl-4-(4-methylnaphthalen-1-yl)-5-oxo-1,4,5,6,7,8-hexahydroquinoline-3-carboxylate |
| PT-136 | ethyl 2-ethyl-4-(4-methoxynaphthalen-1-yl)-5-oxo-1,4,5,6,7,8-hexahydroquinoline-3-carboxylate |
| PT-137 | ethyl 4-(6-methoxynaphthalen-2-yl)-2-methyl-5-oxo-1,4,5,6,7,8-hexahydroquinoline-3-carboxylate |

TABLE 6-continued

| ID (PT-nnn) | Name of Compound |
|---|---|
| PT-138 | ethyl 4-(4,7-dimethoxynaphthalen-1-yl)-2-methyl-5-oxo-1,4,5,6,7,8-hexahydroquinoline-3-carboxylate |
| PT-139 | ethyl 4-(4-(dimethylamino)naphthalen-1-yl)-2-methyl-5-oxo-1,4,5,6,7,8-hexahydroquinoline-3-carboxylate |
| PT-140 | ethyl 2-methyl-5-oxo-1,4,5,6,7,8-hexahydro-4,5'-biquinoline-3-carboxylate |
| PT-141 | ethyl 7,7-dimethyl-5-oxo-4-(5-phenylthiophen-2-yl)-2-propyl-1,4,5,6,7,8-hexahydroquinoline-3-carboxylate |
| PT-142 | ethyl 2-methyl-5-oxo-4-(thiophen-2-yl)-1,4,5,6,7,8-hexahydroquinoline-3-carboxylate |
| PT-143 | ethyl 2-methyl-5-oxo-4-(thiophen-3-yl)-1,4,5,6,7,8-hexahydroquinoline-3-carboxylate |
| PT-144 | ethyl 2-methyl-5-oxo-7-phenyl-4-(thiophen-2-yl)-1,4,5,6,7,8-hexahydroquinoline-3-carboxylate |
| PT-145 | ethyl 2-methyl-5-oxo-7-phenyl-4-(thiophen-3-yl)-1,4,5,6,7,8-hexahydroquinoline-3-carboxylate |
| PT-146 | ethyl 4-(5-chlorothiophen-2-yl)-2,8,8-trimethyl-5-oxo-1,4,5,6,7,8-hexahydroquinoline-3-carboxylate |
| PT-147 | ethyl 4-(5-chlorothiophen-2-yl)-7-(furan-2-yl)-2-methyl-5-oxo-1,4,5,6,7,8-hexahydroquinoline-3-carboxylate |
| PT-148 | ethyl 5-oxo-2-propyl-4-(thiophen-3-yl)-1,4,5,6,7,8-hexahydroquinoline-3-carboxylate |
| PT-149 | ethyl 5-oxo-7-phenyl-2-propyl-4-(thiophen-3-yl)-1,4,5,6,7,8-hexahydroquinoline-3-carboxylate |
| PT-150 | ethyl 7-(furan-2-yl)-5-oxo-2-propyl-4-(thiophen-3-yl)-1,4,5,6,7,8-hexahydroquinoline-3-carboxylate |
| PT-151 | ethyl 7,7-dimethyl-5-oxo-2-propyl-4-(thiophen-3-yl)-1,4,5,6,7,8-hexahydroquinoline-3-carboxylate |
| PT-152 | ethyl 7-isopropyl-5-oxo-2-propyl-4-(thiophen-3-yl)-1,4,5,6,7,8-hexahydroquinoline-3-carboxylate |
| PT-153 | ethyl 4-(furan-2-yl)-2-methyl-5-oxo-1,4,5,6,7,8-hexahydroquinoline-3-carboxylate |
| PT-154 | ethyl 4-(furan-3-yl)-2-methyl-5-oxo-1,4,5,6,7,8-hexahydroquinoline-3-carboxylate |
| PT-155 | ethyl 4-(furan-3-yl)-2-methyl-5-oxo-7-phenyl-1,4,5,6,7,8-hexahydroquinoline-3-carboxylate |
| PT-156 | 2-methoxyethyl 2,7,7-trimethyl-5-oxo-4-(4-phenoxyphenyl)-1,4,5,6,7,8-hexahydroquinoline-3-carboxylate |
| PT-157 | isopropyl 2-methyl-4-(naphthalen-2-yl)-5-oxo-1,4,5,6,7,8-hexahydroquinoline-3-carboxylate |
| PT-158 | isopropyl 2-methyl-4-(naphthalen-1-yl)-5-oxo-1,4,5,6,7,8-hexahydroquinoline-3-carboxylate |
| PT-159 | isopropyl 2,7,7-trimethyl-5-oxo-4-(4-phenylthiophen-2-yl)-1,4,5,6,7,8-hexahydroquinoline-3-carboxylate |
| PT-160 | isopropyl 2,7,7-trimethyl-5-oxo-4-(3-(4-(trifluoromethyl)phenyl)-1H-pyrazol-4-yl)-1,4,5,6,7,8-hexahydroquinoline-3-carboxylate |
| PT-161 | isopropyl 2,7,7-trimethyl-4-(5-methyl-1-o-tolyl-1H-pyrazol-4-yl)-5-oxo-1,4,5,6,7,8-hexahydroquinoline-3-carboxylate |
| PT-162 | isopropyl 2,7,7-trimethyl-5-oxo-4-(3-(thiophen-2-yl)-1H-pyrazol-4-yl)-1,4,5,6,7,8-hexahydroquinoline-3-carboxylate |
| PT-163 | 2-methyl-3-(4-phenylpiperidine-1-carbonyl)-4-(thiophen-3-yl)-4,6,7,8-tetrahydroquinolin-5(1H)-one |
| PT-164 | 2-methyl-5-oxo-N-(4-phenylbutyl)-4-(thiophen-3-yl)-1,4,5,6,7,8-hexahydroquinoline-3-carboxamide |
| PT-165 | 2-methyl-4-(naphthalen-2-yl)-3-(4-phenylpiperazine-1-carbonyl)-4,6,7,8-tetrahydroquinolin-5(1H)-one |
| PT-166 | 2-methyl-3-(4-phenylpiperazine-1-carbonyl)-4-(thiophen-3-yl)-4,6,7,8-tetrahydroquinolin-5(1H)-one |
| PT-167 | 3-(4-(4-chlorophenyl)piperazine-1-carbonyl)-2-methyl-4-(thiophen-3-yl)-4,6,7,8-tetrahydroquinolin-5(1H)-one |
| PT-168 | N-(1-(2,6-dimethylphenoxy)propan-2-yl)-2,7,7-trimethyl-5-oxo-4-(thiophen-3-yl)-1,4,5,6,7,8-hexahydroquinoline-3-carboxamide |
| PT-169 | 2-methyl-4-(naphthalen-2-yl)-3-(4-phenylpiperidine-1-carbonyl)-4,6,7,8-tetrahydroquinolin-5(1H)-one |
| PT-170 | 2-methyl-4-(naphthalen-1-yl)-3-(4-phenylpiperidine-1-carbonyl)-4,6,7,8-tetrahydroquinolin-5(1H)-one |
| PT-171 | 2-methyl-4-(naphthalen-1-yl)-3-(1,2,3,4-tetrahydroisoquinoline-2-carbonyl)-4,6,7,8-tetrahydroquinolin-5(1H)-one |
| PT-172 | 3-(1-(2-methyl-4-(naphthalen-1-yl)-5-oxo-1,4,5,6,7,8-hexahydroquinoline-3-carbonyl)piperidin-4-yl)benzoic acid |
| PT-173 | 4-(1-(2-methyl-4-(naphthalen-1-yl)-5-oxo-1,4,5,6,7,8-hexahydroquinoline-3-carbonyl)piperidin-4-yl)benzoic acid |
| PT-174 | N-(3,3-diphenylpropyl)-2,7,7-trimethyl-5-oxo-4-(thiophen-3-yl)-1,4,5,6,7,8-hexahydroquinoline-3-carboxamide |
| PT-175 | N-(3,3-diphenylpropyl)-4-(3-(4-fluorophenyl)-1H-pyrazol-4-yl)-2,7,7-trimethyl-5-oxo-1,4,5,6,7,8-hexahydroquinoline-3-carboxamide |
| PT-176 | N-(furan-2-ylmethyl)-2-methyl-5-oxo-4-(thiophen-2-yl)-1,4,5,6,7,8-hexahydroquinoline-3-carboxamide |
| PT-177 | N-benzyl-2-methyl-5-oxo-4-(thiophen-2-yl)-1,4,5,6,7,8-hexahydroquinoline-3-carboxamide |
| PT-178 | N-benzyl-2-methyl-5-oxo-4-(thiophen-3-yl)-1,4,5,6,7,8-hexahydroquinoline-3-carboxamide |

TABLE 6-continued

| ID (PT-nnn) | Name of Compound |
|---|---|
| PT-179 | N-benzyl-4-(furan-3-yl)-2-methyl-5-oxo-1,4,5,6,7,8-hexahydroquinoline-3-carboxamide |
| PT-180 | N-(2,6-dimethylphenyl)-2-methyl-5-oxo-4-(thiophen-3-yl)-1,4,5,6,7,8-hexahydroquinoline-3-carboxamide |
| PT-187 | ethyl 2-methyl-5-oxo-4-(thiophen-2-yl)-4,5-dihydro-1H-indeno[1,2-b]pyridine-3-carboxylate |
| PT-188 | ethyl 2-chloro-6-methoxy-2'-methyl-5'-oxo-1',4',5',6',7',8'-hexahydro-3,4'-biquinoline-3'-carboxylate |
| PT-189 | ethyl 4-(2-chloropyridin-3-yl)-2-methyl-5-oxo-1,4,5,6,7,8-hexahydroquinoline-3-carboxylate |
| PT-190 | ethyl 2-methyl-5-oxo-1,4,5,6,7,8-hexahydro-4,4'-biquinoline-3-carboxylate |
| PT-265 | 2-methyl-4-(naphthalen-1-yl)-3-(piperidine-1-carbonyl)-4,6,7,8-tetrahydroquinolin-5(1H)-one |
| PT-266 | 2-methyl-4-(naphthalen-1-yl)-5-oxo-N'-(2-phenylacetyl)-1,4,5,6,7,8-hexahydroquinoline-3-carbohydrazide |
| PT-287 | 4-(1-(2-methyl-4-(naphthalen-1-yl)-5-oxo-1,4,5,6,7,8-hexahydroquinoline-3-carbonyl)piperidin-4-yl)benzamide |
| PT-297 | 4-(4-(2-methyl-4-(naphthalen-1-yl)-5-oxo-1,4,5,6,7,8-hexahydroquinoline-3-carbonyl)piperazin-1-yl)benzoic acid |
| PT-303 | 4-chloro-2-methoxybenzyl 4-(2,6-dichlorophenyl)-2-methyl-5-oxo-1,4,5,6,7,8-hexahydroquinoline-3-carboxylate |
| PT-320 | benzyl 2-methyl-4-(naphthalen-2-yl)-5-oxo-1,4,5,6,7,8-hexahydroquinoline-3-carboxylate |
| PT-323 | benzyl 2-methyl-5-oxo-4-phenyl-1,4,5,6,7,8-hexahydroquinoline-3-carboxylate |
| PT-328 | benzyl 4-(2-(benzyloxy)phenyl)-2-methyl-5-oxo-1,4,5,6,7,8-hexahydroquinoline-3-carboxylate |
| PT-329 | benzyl 4-(2-bromophenyl)-2-methyl-5-oxo-1,4,5,6,7,8-hexahydroquinoline-3-carboxylate |
| PT-334 | benzyl 4-(anthracen-9-yl)-2-methyl-5-oxo-1,4,5,6,7,8-hexahydroquinoline-3-carboxylate |
| PT-335 | benzyl 4-(benzo[b]thiophen-2-yl)-2-methyl-5-oxo-1,4,5,6,7,8-hexahydroquinoline-3-carboxylate |
| PT-336 | benzyl 4-(biphenyl-2-yl)-2-methyl-5-oxo-1,4,5,6,7,8-hexahydroquinoline-3-carboxylate |
| PT-452 | ethyl 4-(4-(2-methyl-4-(naphthalen-1-yl)-5-oxo-1,4,5,6,7,8-hexahydroquinoline-3-carbonyl)piperazin-1-yl)benzoate |

Given a desired product, such as for example set out in the above table, the necessary starting materials generally may be determined by inspection, based on the general procedure set out in Example 7A.

Example 7D

Preparation of a Compound of Formula (VI) Varying R4, R5, R6

Similarly, by essentially following the procedures set out in Examples 7A and 78 above, but optionally replacing the 1,3-cyclohexanedione (11) with another 1,3-cyclohexanedione having the general structure (11) set out in Example 7A (or replacing it with a 1,3-cyclopentanedione having the general structure (13), as explained at the end of Example 7A), and/or optionally replacing the aldehyde (2) with other aldehydes of general formula $R_1$—C(O)H and/or replacing the beta-keto compound (3) with other beta-keto compounds, further compounds of Formula (VI) may be prepared.

Example 8

Example 8A

General Method for Synthesis of Compounds of Formula (I)

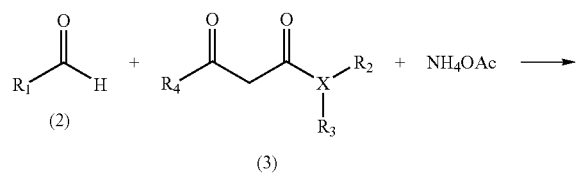

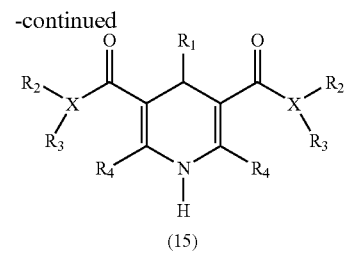

Referring to the above reaction, the aldehyde (2) is reacted with a beta-keto compound (3) to give the product (15), which is a compound of Formula (I). Given a desired product (15) for which the substituent groups $R_1$, $X(R_2)(R_3)$, and $R_4$ are defined, the necessary starting materials (2) and (3) may be determined by inspection. In certain cases, X is a nitrogen and $R_2$ and $R_3$ may be substituents (such as are described elsewhere herein) bound to the nitrogen, such that the beta-keto compound (3) is a beta-keto amide. In certain other eases, X taken together with $R_3$ is an oxygen and $R_2$ may be a substituent (such as described elsewhere herein) bound to the oxygen, such that the beta-keto compound (3) is a beta-keto ester.

To a solution of the aldehyde (2) (5.0 mmole) in hot ethanol (15 ml) was added the beta-keto ester or beta-keto amide (3) (10.0 mmole) followed by the ammonium acetate (10.0 mmole). The mixture is heated to reflux for 15 h. Sometimes a precipitate would occur and workup consisted of filtration and washing with ether-hexanes mixtures. If a precipitate did not appear, the crude reaction mixture is reduced in vacuo. The material is then dissolved in ethyl acetate and washed with water (2x), saturated aqueous $NaHCO_3$, then brine. The organic phase is decanted and reduced in vacuo and purified on a silica gel flash column to provide the pure desired product (15).

Example 8B

Preparation of a Compound of Formula (I) in which R2 is Propyl, R3 is Ethoxycarbonyl, R4 is 5-bromothiophen-2-yl, R5 is Ethoxy, and R6 is Propyl Synthesis of diethyl 4-(5-bromothiophen-2-yl)-2,6-dipropyl-1,4-dihydropyridine-3,5-dicarboxylate (PT-182)

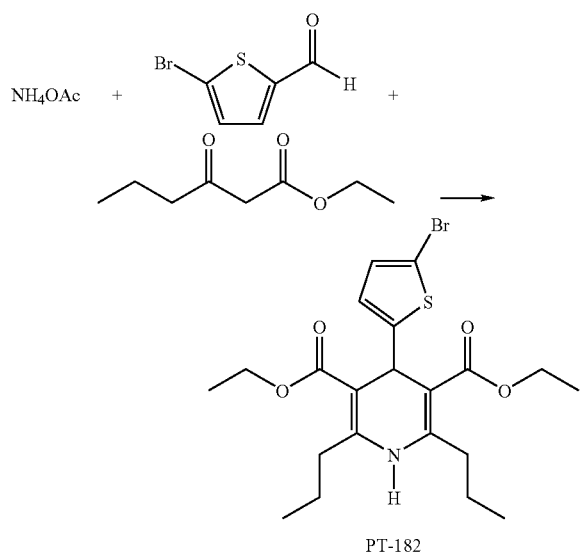

To a solution of ethyl propylacetoacetate (1.59 ml, 10.0 mmole) in hot ethanol (20 ml) was added 5-bromo-2-thiophenecarboxaldehyde (0.958 ml, 5.0 mmole) followed by the ammonium acetate (0.616 g, 8.0 mmole). The mixture was held at reflux for 24 h. No precipitate was formed. The reaction mixture was reduced in vacuo. The crude material was dissolved in ethyl acetate and washed with water (2×) and the organic phase was reduced in vacuo. This material was applied to 150 g $SiO_2$ flash column and eluted with 25% ethyl acetate:hexanes eluent to provide the desired product (2.0 g, 85%) as a light yellow oil. Rf=0.45 in 30% ethyl acetate:hexanes. $^1$H NMR (400 MHz; $CDCl_3$) d 6.77 (d, 1H, J=3.9 Hz); 6.54 (dd, 1H, J=3.9, 0.78 Hz); 5.9 (bs, 1H); 5.28 (s, 1H); 4.23-4.15 (m, 4H); 2.81-2.72 (m, 2H); 2.64-2.56 (m, 2H); 1.72-1.54 (m, 4H); 1.28 (at, 6H, J=7.0 Hz); 0.88 (at, 6H, J=7.4 Hz). LC MS shows MH+ at 470 and 472.

Example 8C

Preparation of a Compound of Formula (I) Varying R2, R3, R4, R5, R6

Similarly, by essentially following the procedures set out in Examples 8A and 8B above, but optionally replacing the aldehyde (2) with other aldehydes of general formula $R_1$—C(O)H, and/or replacing the beta-keto compound (3) with other beta-keto compounds (e.g. acetoacetate or acetoacetamide) having the necessary substituents to result in the indicated products, the following compounds of Formula (I) were prepared:

TABLE 7

| ID (PT-nnn) | Name of Compound |
| --- | --- |
| PT-107 | diethyl 2,6-dimethyl-4-(naphthalen-2-yl)-1,4-dihydropyridine-3,5-dicarboxylate |
| PT-108 | diethyl 2,6-dimethyl-4-(naphthalen-1-yl)-1,4-dihydropyridine-3,5-dicarboxylate |
| PT-109 | diethyl 4-(2,3-dihydrobenzo[b][1,4]dioxin-6-yl)-2,6-dimethyl-1,4-dihydropyridine-3,5-dicarboxylate |
| PT-110 | diethyl 2,6-dimethyl-4-(thiophen-3-yl)-1,4-dihydropyridine-3,5-dicarboxylate |
| PT-111 | diethyl 2,6-dimethyl-4-(thiophen-2-yl)-1,4-dihydropyridine-3,5-dicarboxylate |
| PT-112 | 5-(3,5-bis(ethoxycarbonyl)-2,6-dimethyl-1,4-dihydropyridin-4-yl)thiophene-2-carboxylic acid |
| PT-113 | diethyl 4-(5-ethylthiophen-2-yl)-2,6-dimethyl-1,4-dihydropyridine-3,5-dicarboxylate |
| PT-114 | diethyl 4-(benzo[b]thiophen-2-yl)-2,6-dimethyl-1,4-dihydropyridine-3,5-dicarboxylate |
| PT-115 | diethyl 4-(benzo[b]thiophen-3-yl)-2,6-dimethyl-1,4-dihydropyridine-3,5-dicarboxylate |
| PT-116 | diethyl 2,6-dimethyl-4-(3-methylbenzo[b]thiophen-2-yl)-1,4-dihydropyridine-3,5-dicarboxylate |
| PT-117 | diethyl 2,6-dimethyl-4-(3-methylbenzo[b]thiophen-2-yl)pyridine-3,5-dicarboxylate |
| PT-118 | diethyl 4-(5-(4-chlorophenyl)furan-2-yl)-2,6-dimethyl-1,4-dihydropyridine-3,5-dicarboxylate |
| PT-119 | diethyl 2,6-dimethyl-4-(5-(2-(trifluoromethyl)phenyl)furan-2-yl)-1,4-dihydropyridine-3,5-dicarboxylate |
| PT-120 | diethyl 4-(furan-3-yl)-2,6-dimethyl-1,4-dihydropyridine-3,5-dicarboxylate |
| PT-121 | diethyl 4-(5-ethylfuran-2-yl)-2,6-dimethyl-1,4-dihydropyridine-3,5-dicarboxylate |
| PT-122 | diethyl 4-(benzofuran-2-yl)-2,6-dimethyl-1,4-dihydropyridine-3,5-dicarboxylate |
| PT-123 | diisopropyl 2,6-dimethyl-4-(naphthalen-1-yl)-1,4-dihydropyridine-3,5-dicarboxylate |
| PT-124 | diisopropyl 4-(5-bromothiophen-2-yl)-2,6-dimethyl-1,4-dihydropyridine-3,5-dicarboxylate |
| PT-125 | bis(2-methoxyethyl) 4-(3-bromothiophen-2-yl)-2,6-dimethyl-1,4-dihydropyridine-3,5-dicarboxylate |
| PT-126 | diisopropyl 4-(5-(4-chlorophenyl)furan-2-yl)-2,6-dimethyl-1,4-dihydropyridine-3,5-dicarboxylate |
| PT-127 | diisopropyl 4-(1-(4-fluorophenyl)-5-methyl-1H-pyrazol-4-yl)-2,6-dimethyl-1,4-dihydropyridine-3,5-dicarboxylate |

TABLE 7-continued

| ID (PT-nnn) | Name of Compound |
|---|---|
| PT-128 | diisopropyl 4-(3-(4-fluorophenyl)-1H-pyrazol-4-yl)-2,6-dimethyl-1,4-dihydropyridine-3,5-dicarboxylate |
| PT-129 | dibenzyl 2,6-dimethyl-4-(naphthalen-2-yl)-1,4-dihydropyridine-3,5-dicarboxylate |
| PT-130 | bis(3,4-dimethoxybenzyl) 2,6-dimethyl-4-(naphthalen-2-yl)-1,4-dihydropyridine-3,5-dicarboxylate |
| PT-181 | diethyl 4-(5-bromothiophen-2-yl)-2,6-diethyl-1,4-dihydropyridine-3,5-dicarboxylate |
| PT-182 | diethyl 4-(5-bromothiophen-2-yl)-2,6-dipropyl-1,4-dihydropyridine-3,5-dicarboxylate |
| PT-183 | diethyl 4-(5-bromothiophen-2-yl)-2,6-diisopropyl-1,4-dihydropyridine-3,5-dicarboxylate |
| PT-191 | diethyl 1,2,6-trimethyl-4-(naphthalen-1-yl)-1,4-dihydropyridine-3,5-dicarboxylate |
| PT-429 | diethyl 4-(2,4-dimethoxyphenyl)-2,6-dimethyl-1,4-dihydropyridine-3,5-dicarboxylate |
| PT-430 | diethyl 4-(2-bromophenyl)-2,6-dimethyl-1,4-dihydropyridine-3,5-dicarboxylate |
| PT-431 | diethyl 4-(2-cyano-4-methoxyphenyl)-2,6-dimethyl-1,4-dihydropyridine-3,5-dicarboxylate |
| PT-432 | diethyl 4-(2-fluoro-4-methoxyphenyl)-2,6-dimethyl-1,4-dihydropyridine-3,5-dicarboxylate |
| PT-433 | diethyl 4-(2-methoxy-4-nitrophenyl)-2,6-dimethyl-1,4-dihydropyridine-3,5-dicarboxylate |
| PT-434 | diethyl 4-(2-methoxyphenyl)-2,6-dimethyl-1,4-dihydropyridine-3,5-dicarboxylate |
| PT-436 | diethyl 4-(4-(dimethylamino)-2-methoxyphenyl)-2,6-dimethyl-1,4-dihydropyridine-3,5-dicarboxylate |
| PT-437 | diethyl 4-(4-(dimethylamino)-2-nitrophenyl)-2,6-dimethyl-1,4-dihydropyridine-3,5-dicarboxylate |
| PT-438 | diethyl 4-(biphenyl-2-yl)-2,6-dimethyl-1,4-dihydropyridine-3,5-dicarboxylate |
| PT-439 | diethyl 4-(biphenyl-3-yl)-2,6-dimethyl-1,4-dihydropyridine-3,5-dicarboxylate |

Given a desired product, such as for example set out in the above table, the necessary starting materials generally may be determined by inspection, based on the general procedure set out in Example 8A.

Example 8D

Preparation of a Compound of Formula (I) Varying R2, R3, R4, R5, R6

Similarly, by essentially following the procedures set out in Example 8A and 8B above, but optionally replacing the aldehyde (2) with other aldehydes of general formula $R_1$—C(O)H, and/or replacing the beta-keto compound (3) with other beta-keto compounds (e.g. acetoacetate or acetoacetamide), further compounds of Formula (I) may be prepared.

Example 9

Example 9A

General Method for Synthesis of Compounds of Formula (I)

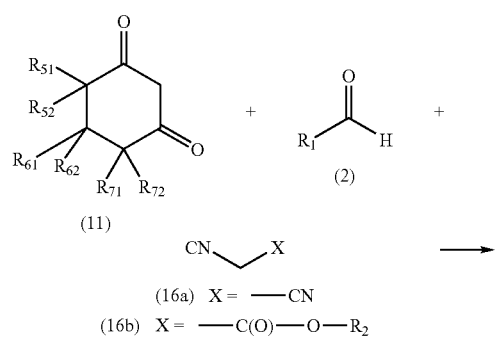

-continued

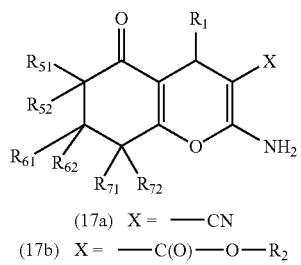

(17a) X = —CN
(17b) X = —C(O)—O—$R_2$

Referring to the above reaction, the 1,3-cyclohexanedione (11) is reacted with an aldehyde (2) and malononitrile (16a) (X=—CN) or a cyanoacetate ester (16b) (X=—C(O)—O—$R_2$) to give the product (17a) or (17b), which is a compound of Formula (I). Given a desired product (17a) or (17b) for which the substituent groups $R_1$, X, $R_{51}$, $R_{52}$, $R_{61}$, $R_{62}$, $R_{71}$, $R_{72}$, are defined, the necessary starting materials (2), (11), and (16a) or (16b) may be determined by inspection.

A solution of the aldehyde (2) (10.0 mmole) and malononitrile (16a) or cyanoacetate ester (16b) (10.0 mmole) in hot ethanol (20.0 ml) is heated at reflux for 15 minutes. Observe a copious amount of precipitate, which is the malononitrile Knoevenagel product if malononitrile (16a) was used or an alpha-cyano ester product if the cyanoacetate ester (16b) was used. To this mixture is added the 1,3-cyclohexanedione (11) and the mixture is heated at reflux for 2 h, then stirred at room temperature for 16 h. The crude reaction is reduced in vacuo and dissolved in ethyl acetate. It is washed with water then brine. The organic phase is decanted and reduced in vacuo to provide solid material. It is filtered and washed with ethyl ether to provide clean desired material.

It is noted that essentially the same reaction may be performed, but substituting a 1,3-cyclopentanedione (13) and ending with the product (18a) or (18b), as shown here:

59

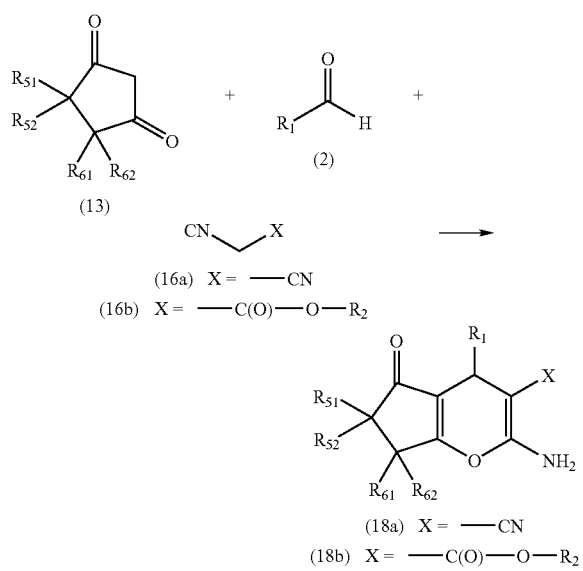

Thus, compounds of the invention having the structure given by Formula (I) wherein R5 and R6 taken together form a bridging group may be synthesized as described in this example.

Example 9B

Preparation of a Compound of Formula (I) in which R4 is Phenyl, R3 is Ethoxycarbonyl, R2 is Amino, and R5 and R6 Taken Together Form a Bridging Group Synthesis of ethyl 2-amino-5-oxo-4-phenyl-5,6,7,8-tetrahydro-4H-chromene-3-carboxylate (PT-097)

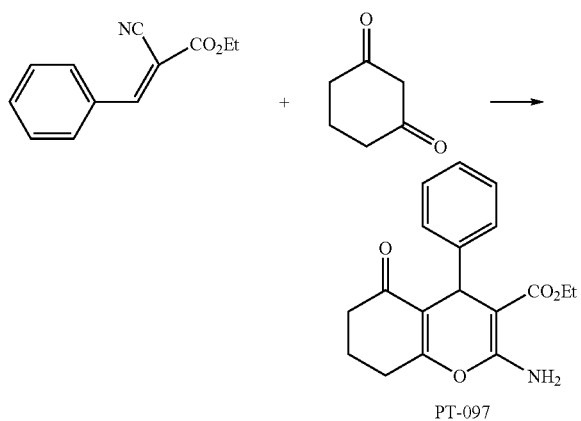

To a solution of 1,3-cyclohexane dione (0.56 g, 5.0 mmole) in hot ethanol (10 ml) was added ethyl trans-a-cyanocinnamate (1.0 g, 5.0 mmole) and the mixture heated at reflux for 18 h. The mixture was cooled to room temperature, filtered and washed with ethanol to provide the desired product (1.30 g, 83%) as a white powder. $^1$H NMR (400 MHz; CDCl$_3$) d 7.29-7.0 (m, 5H); 6.2 (bs, 2H); 4.72 (s, 1H); 4.09-3.96 (m, 2H); 2.64-2.48 (m, 2H); 2.40-2.26 (m, 2H); 2.06-1.88 (m, 2H); 1.14 (t, 3H, J=7.4 Hz). LC MS shows MH+ at 314.

60

Example 9C

Preparation of a Compound of Formula (I) in which R4 is furan-2-yl, R3 is Cyano, R2 is Amino, R5 is Ethoxy, and R6 is Methyl This example describes a synthesis that is essentially similar to Examples 9A and 9B, except the cyclic diones of Examples 9A and 9B are replaced in this Example with an open-chain (non-cyclic) beta-ketoester.

Synthesis of ethyl 6-amino-5-cyano-4-(furan-2-yl)-2-methyl-4H-pyran-3-carboxylate (PT-092)

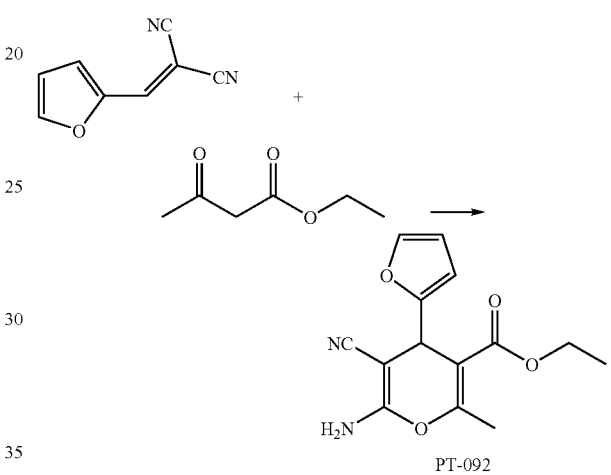

To a solution of (2-furanylmethylene)malononitrile (0.72 g, 5.0 mmole) in hot ethanol (5.0 ml) was added ethyl acetoacetate (0.647 ml, 5.0 mmole) followed by 1 drop of pyrrolidine. The mixture was refluxed for 15 h. Upon cooling the mixture to room temperature a precipitate formed. The mixture was filtered to provide the desired product (0.753 g, 55%) as pinkish powder. Rf=0.4 in 50% ethyl actetate:hexanes. $^1$H NMR (400 MHz; CDCl$_3$) d 7.295 (m, 1H); 6.27 (dd, 1H, J=3.1, 1.95 Hz); 6.10 (d, 1H, J=3.1 Hz); 4.63 (s, 1H); 4.50 (bs, 2H); 4.22-4.07 (m, 2H); 2.36 (s, 3H); 1.20 (t, 3H, J=7.0 Hz). LC MS shows MH+ at 275.

This example describes a synthesis that is essentially similar to Examples 9A and 9B above, except the cyclic diones of Examples 9A and 9B are replaced in this Example with an open-chain (non-cyclic) beta-ketoester, providing for a product in which R5 and R6 do not form a bridging group. Similarly, by essentially following the procedures set out in Examples 9A above, but replacing the cyclic dione (11) or (13) with a beta-ketoester (either ethyl acetoacetate as in this example, above, or other beta-ketoesters such as are described elsewhere herein), and/or optionally replacing the aldehyde (2) with other aldehydes of general formula R$_1$—C(O)H and/or replacing the malononitrile (16a) (X=—CN) or cyanoacetate ester (16b) (X=—C(O)—O—R$_2$) with other cyanoacetate ester (16b) compounds (e.g. ethyl cyanoacetate or benzyl cyanoacetate), further compounds of Formula (I) in which R5 and R6 do not form a bridging group may be prepared.

Example 9D

Preparation of a Compound of Formula (I) Varying R3, R4, R5, R6

Similarly, by essentially following the procedures set out in Examples 9A and 9B above, but optionally replacing the 1,3-cyclohexanedione (11) with another 1,3-cyclohexanedione having the general structure (11) set out in Example 9A (or replacing it with a 1,3-cyclopentanedione having the general structure (13), as explained at the end of Example 9A), and/or optionally replacing the aldehyde (2) with other aldehydes of general formula $R_1$—C(O)H, and/or replacing the malononitrile (16a) (X=—CN) or cyanoacetate ester (16b) (X=—C(O)—O—$R_2$) with other cyanoacetate ester (16b) compounds (e.g. ethyl cyanoacetate or benzyl cyanoacetate) having the necessary substituents to result in the indicated products, the following compounds of Formula (I) were prepared:

TABLE 8

| ID (PT-nnn) | Name of Compound |
|---|---|
| PT-093 | 2-amino-4-(4-bromophenyl)-5-oxo-4,5,6,7-tetrahydrocyclopenta[b]pyran-3-carbonitrile |
| PT-094 | 2-amino-4-(4-bromophenyl)-5-oxo-7-phenyl-5,6,7,8-tetrahydro-4H-chromene-3-carbonitrile |
| PT-096 | 2-amino-4-(4-bromophenyl)-5-oxo-5,6,7,8-tetrahydro-4H-chromene-3-carbonitrile |
| PT-097 | ethyl 2-amino-5-oxo-4-phenyl-5,6,7,8-tetrahydro-4H-chromene-3-carboxylate |
| PT-098 | 3-(2-amino-3-cyano-7,7-dimethyl-5-oxo-5,6,7,8-tetrahydro-4H-chromen-4-yl)benzoic acid |
| PT-099 | 2-amino-5-oxo-4-(thiophen-2-yl)-5,6,7,8-tetrahydro-4H-chromene-3-carbonitrile |
| PT-100 | 2-amino-5-oxo-4-(thiophen-3-yl)-5,6,7,8-tetrahydro-4H-chromene-3-carbonitrile |
| PT-101 | 2-amino-5-oxo-7-phenyl-4-(thiophen-2-yl)-5,6,7,8-tetrahydro-4H-chromene-3-carbonitrile |
| PT-102 | 2-amino-5-oxo-7-phenyl-4-(thiophen-3-yl)-5,6,7,8-tetrahydro-4H-chromene-3-carbonitrile |
| PT-103 | 2-amino-4-(furan-2-yl)-5-oxo-5,6,7,8-tetrahydro-4H-chromene-3-carbonitrile |
| PT-104 | 2-amino-4-(furan-2-yl)-5-oxo-7-phenyl-5,6,7,8-tetrahydro-4H-chromene-3-carbonitrile |
| PT-105 | 2-amino-4-(4-bromophenyl)-5-oxo-5,7-dihydro-4H-furo[3,4-b]pyran-3-carbonitrile |
| PT-106 | 2-amino-4-(furan-2-yl)-5-oxo-4,5-dihydropyrano[3,2-c]chromene-3-carbonitrile |

Given a desired product, such as for example set out in the above table, the necessary starting materials generally may be determined by inspection, based on the general procedure set out in Example 9A.

Example 9E

Preparation of a Compound of Formula (I) Varying R3, R4, R5, R6

Similarly, by essentially following the procedures set out in Examples 9A and 9B above, but optionally replacing the 1,3-cyclohexanedione (11) with another 1,3-cyclohexanedione having the general structure (11) set out in Example 9A (or replacing it with a 1,3-cyclopentanedione having the general structure (13), as explained at the end of Example 9A), and/or optionally replacing the aldehyde (2) with other aldehydes of general formula $R_1$—C(O)H and/or replacing the malononitrile (16a) (X=—CN) or cyanoacetate ester (16b) (X=—C(O)—O—$R_2$) with other cyanoacetate ester (16b) compounds (e.g. ethyl cyanoacetate or benzyl cyanoacetate), further compounds of Formula (I) may be prepared.

Example 10

Further Preparation of Compounds of Formula (I)

Example 10A

Suzuki Coupling Procedure

Compounds of Formulas (I)-(VI) that have halo substituents on aromatic rings (e.g. aryl or heteroaryl rings of R4 or R5 or elsewhere in the molecule) may be made as described above in Examples 1-9. These compounds having halo-substituted aryl groups may then be modified using a Suzuki coupling procedure. An example is given here.

Synthesis of (4'-methoxybiphenyl-4-yl)methyl 5-methyl-7-(naphthalen-1-yl)-4,7-dihydrotetrazolo[1,5-a]pyrimidine-6-carboxylate (PT-199)

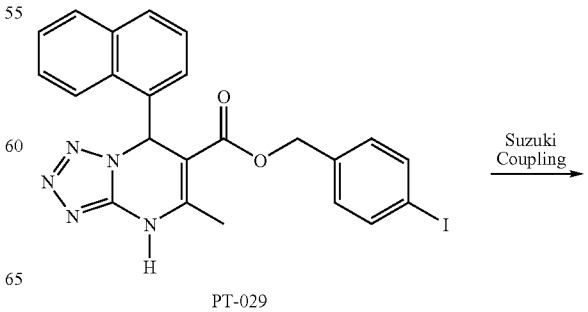

PT-029

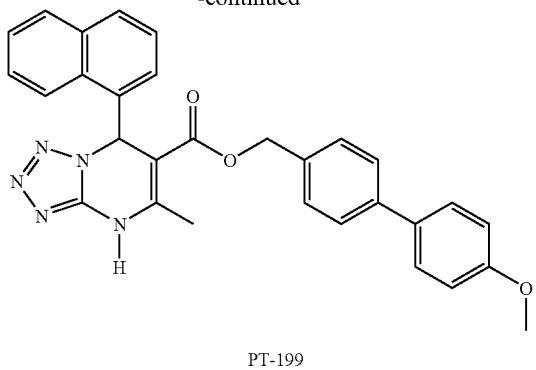

PT-199

PT-029 (200 mg; 0.38 mmole) was dissolved in dry DME (4 ml) and dry DMF (0.5 ml) while heating to 50° C. After dissolution, the solution was cooled to room temperature and para-methoxyphenylboronic acid (145 mg; 0.95 mmole) was added followed by 1.0 ml of a 2M $Na_2CO_3$ solution, then $Pd(Cl)_2(PPh_3)_2$ (70 mg; 0.1 mmole). The mixture was then heated at 82° C. for 15 h. The mixture was cooled to room temperature and ethyl acetate was added. The organic phase was washed with saturated $NaHCO_3$ solution, and the organic phase was separated and dried over $MgSO_4$. The organic phase was filtered from the magnesium sulfate and then evaporated in vacuo. The crude material was purified on a silica gel column (15 g) using 1:1 ethyl acetate:hexanes eluent ($R_f$=0.35) to provide 81 mg (42%) of PT-199 as a light grey powder. $H^1$ NMR (400 MHz) ($CDCl_3$) 10.2 (1H), 8.5-6.6 (m, 16H), 4.98 (d, J=12.5 Hz, 1H), 4.92 (d, J=12.5 Hz, 1H), 3.9 (s, 3H), 2.85 (s, 3H). LC MS shows 96% purity and MS CI 504 (M+H) and 1007 (2M+H).

Example 10B

Suzuki Coupling Procedure

Another Example of a Suzuki coupling procedure on a compound of Formula (I) is given here.

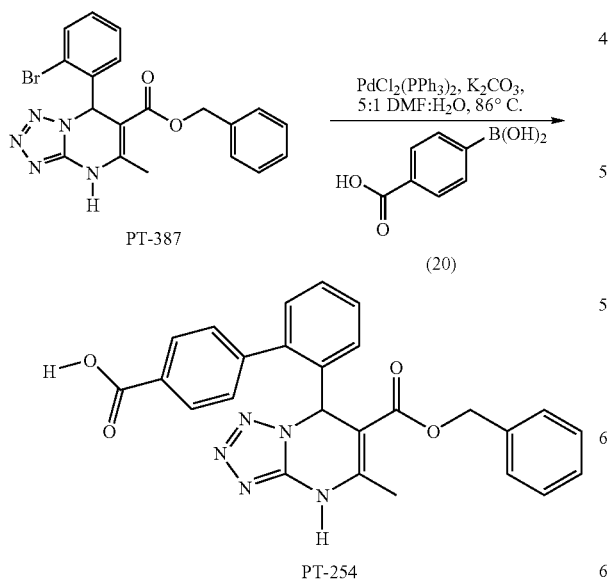

Procedure: To a solution of PT-387 (855 mg, 2.00 mmol) and (20) (500 mg, 3.00 mmol) in DMF (15 mL) was added $K_2CO_3$ (830 mg, 6.00 mmol) and $H_2O$ (3 mL). The reaction mixture was stirred for 5 min under an atmosphere of dry $N_2$. $PdCl_2(PPh_3)_2$ (70 mg, 0.10 mmol) was added, and the resulting mixture was heated at 86° C. for 5 h. The mixture was cooled, diluted with EtOAc (20 mL), filtered through a layer of celite, washed with EtOAc (80 mL) and $H_2O$ (80 mL) and transferred to a separation funnel. The organic phase was washed with 0.1 N LiOH (100 mL, 10.00 mmol), and the combined aqeuous phase was washed with diethyl ether (50 mL), then EtOAc (2×50 mL). The pH value was adjusted to 2-3, and the milkish precipitate was filtered, washed with $H_2O$ (500 mL), and dried to give a gel-like solid. LCMS showed only 70% as the desired product. To the crude product was added boiling EtOAc (30 mL) and the mixture was sonicated, filtered, washed with EtOAc (30 mL), and dried to afford a white solid PT-254 (286 mg, 31%). MS m/z 468.2 (M+H). >94% HPLC purity. $^1$H NMR (400 MHz; dmso-D6) 11.3 (s, 1H); 7.98 (d, J=8.6 Hz, 2H); 7.30-7.60 (m, 5H); 7.10-7.28 (m, 4H); 6.84 (d, J=6.3 Hz, 2H); 6.73 (s, 1H); 4.96 (q, J=13.0 Hz, 2H); 2.53 (d, J=2.0 Hz, 3H).

Example 10C

Suzuki Coupling Procedure

Another Example of a Suzuki coupling procedure on a compound of Formula (I) is given here.

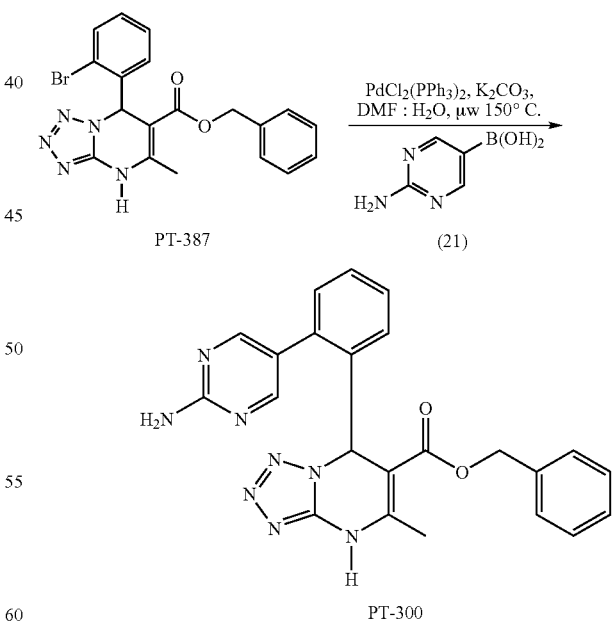

Procedure: To a solution of PT-387 (427 mg, 1.00 mmol) and (21) (208 mg, 1.50 mmol) in DMF (2.5 mL) was added $K_2CO_3$ (345 mg, 2.50 mmol) and $H_2O$ (0.5 mL). The reaction mixture was stirred for 5 min under an atmosphere of dry $N_2$. $PdCl_2(PPh_3)_2$ (35 mg, 0.05 mmol) was added, and the resulting mixture was capped, heated at 150° C. in a Personal Chemistry microwave for 40 min. The mixture was cooled, decanted to a round-bottom flask, washed with 10% DMF in ethyl acetate (EtOAc) (50 mL), filtered through a layer of celite, again washed with 10% DMF in EtOAc (50 mL), and transferred to a separation funnel. The organic phase was washed with 2N $NaHCO_3$ (10 mL, 20.0 mmol), $H_2O$ (20 mL), 30% aqueous $NH_4Cl$ (50 mL) and brine (50 mL), and then was dried to give yellow solid. Methanol in ether (0.5, 1.5 mL, respectively) was added, and the mixture was sonicated, filtered, washed with 25% MeOH in ether (8 mL), and then dried to give white solid PT-300 (299 mg, 0.68 mmol, 68%). MS m/z 441.2 (M+H). HPLC purity >95%. $^1$H NMR (400 MHz; dmso-D6) 11.3 (s, 1H); 8.22 (s, 2H); 7.30-7.50 (m, 3H); 7.15-7.25 (m, 4H); 6.85 (dd, J=6.6 and 1.5 Hz, 2H); 6.79 (s, 1H); 6.70 (s, 1H); 5.07 (s, 1H); 4.89 (s, 1H); 2.44 (s, 3H).

Example 10D

Preparation of a Compounds Using Suzuki Coupling Procedure to Modify a Halo-Aryl Group Compounds of Formulas (I)-(VI) that have halo substituents on aromatic rings (e.g. aryl or heteroaryl rings of R4 or R5 or elsewhere on the molecule) were made as described in Examples 1-9. The R4 or R5 groups were then modified by essentially following the procedures set out in Examples 10A, 10B and 10C above, but optionally replacing the aryl-boronic acid with other aryl-boronic acids and/or optionally replacing the compound having the aryl-halo group (e.g. a compound of any of Formulas (I)-(VI)) with another compound having an halo-aryl group. The following compounds of Formula (I) were prepared.

TABLE 9

| ID (PT-nnn) | Name of Compound |
|---|---|
| PT-199 | (4'-methoxybiphenyl-4-yl)methyl 5-methyl-7-(naphthalen-1-yl)-4,7-dihydrotetrazolo[1,5-a]pyrimidine-6-carboxylate |
| PT-200 | (4'-(methoxycarbonyl)biphenyl-4-yl)methyl 5-methyl-7-(naphthalen-1-yl)-4,7-dihydrotetrazolo[1,5-a]pyrimidine-6-carboxylate |
| PT-235 | (R)-benzyl 5-methyl-7-(2-(5-methylfuran-2-yl)phenyl)-4,7-dihydrotetrazolo[1,5-a]pyrimidine-6-carboxylate |
| PT-236 | (R)-benzyl 5-methyl-7-(4'-(trifluoromethyl)biphenyl-2-yl)-4,7-dihydrotetrazolo[1,5-a]pyrimidine-6-carboxylate |
| PT-237 | (R)-benzyl 7-(2-(5-chlorothiophen-2-yl)phenyl)-5-methyl-4,7-dihydrotetrazolo[1,5-a]pyrimidine-6-carboxylate |
| PT-238 | (R)-benzyl 7-(3'-carbamoylbiphenyl-2-yl)-5-methyl-4,7-dihydrotetrazolo[1,5-a]pyrimidine-6-carboxylate |
| PT-239 | (R)-benzyl 7-(3'-cyanobiphenyl-2-yl)-5-methyl-4,7-dihydrotetrazolo[1,5-a]pyrimidine-6-carboxylate |
| PT-240 | (R)-benzyl 7-(3'-fluorobiphenyl-2-yl)-5-methyl-4,7-dihydrotetrazolo[1,5-a]pyrimidine-6-carboxylate |
| PT-241 | (R)-benzyl 7-(3'-methoxybiphenyl-2-yl)-5-methyl-4,7-dihydrotetrazolo[1,5-a]pyrimidine-6-carboxylate |
| PT-242 | (R)-benzyl 7-(4'-carbamoylbiphenyl-2-yl)-5-methyl-4,7-dihydrotetrazolo[1,5-a]pyrimidine-6-carboxylate |
| PT-243 | (R)-benzyl 7-(4'-cyanobiphenyl-2-yl)-5-methyl-4,7-dihydrotetrazolo[1,5-a]pyrimidine-6-carboxylate |
| PT-248 | 2'-(3-(benzyloxycarbonyl)-2-methyl-5-oxo-1,4,5,6,7,8-hexahydroquinolin-4-yl)biphenyl-3-carboxylic acid |
| PT-249 | 2'-(3-(benzyloxycarbonyl)-2-methyl-5-oxo-1,4,5,6,7,8-hexahydroquinolin-4-yl)biphenyl-4-carboxylic acid |
| PT-250 | 2'-(3-(ethoxycarbonyl)-2-methyl-5-oxo-1,4,5,6,7,8-hexahydroquinolin-4-yl)biphenyl-4-carboxylic acid |
| PT-253 | 2'-(6-(benzyloxycarbonyl)-5-methyl-4,7-dihydrotetrazolo[1,5-a]pyrimidin-7-yl)biphenyl-3-carboxylic acid |
| PT-254 | 2'-(6-(benzyloxycarbonyl)-5-methyl-4,7-dihydrotetrazolo[1,5-a]pyrimidin-7-yl)biphenyl-4-carboxylic acid |
| PT-273 | 3-(2-(6-(methoxycarbonyl)-5-methyl-4,7-dihydrotetrazolo[1,5-a]pyrimidin-7-yl)benzo[b]thiophen-3-yl)benzoic acid |
| PT-275 | 3-(3-(6-(methoxycarbonyl)-5-methyl-4,7-dihydrotetrazolo[1,5-a]pyrimidin-7-yl)benzo[b]thiophen-2-yl)benzoic acid |
| PT-292 | 4-(2-(6-(ethoxycarbonyl)-5-methyl-4,7-dihydrotetrazolo[1,5-a]pyrimidin-7-yl)thiophen-3-yl)benzoic acid |
| PT-293 | 4-(3-(6-((cyclopropylmethoxy)carbonyl)-5-methyl-4,7-dihydrotetrazolo[1,5-a]pyrimidin-7-yl)benzo[b]thiophen-2-yl)benzoic acid |
| PT-294 | 4-(3-(6-(benzyloxycarbonyl)-5-methyl-4,7-dihydrotetrazolo[1,5-a]pyrimidin-7-yl)benzo[b]thiophen-2-yl)benzoic acid |
| PT-296 | 4-(3-(6-(methoxycarbonyl)-5-methyl-4,7-dihydrotetrazolo[1,5-a]pyrimidin-7-yl)benzo[b]thiophen-2-yl)benzoic acid |
| PT-344 | benzyl 5-methyl-7-(2'-methylbiphenyl-2-yl)-4,7-dihydrotetrazolo[1,5-a]pyrimidine-6-carboxylate |
| PT-348 | benzyl 5-methyl-7-(3'-(methylsulfonamido)biphenyl-2-yl)-4,7-dihydrotetrazolo[1,5-a]pyrimidine-6-carboxylate |
| PT-349 | benzyl 5-methyl-7-(3'-(trifluoromethyl)biphenyl-2-yl)-4,7-dihydrotetrazolo[1,5-a]pyrimidine-6-carboxylate |
| PT-350 | benzyl 5-methyl-7-(3'-methylbiphenyl-2-yl)-4,7-dihydrotetrazolo[1,5-a]pyrimidine-6-carboxylate |
| PT-351 | benzyl 5-methyl-7-(3-phenylfuran-2-yl)-4,7-dihydrotetrazolo[1,5-a]pyrimidine-6-carboxylate |
| PT-352 | benzyl 5-methyl-7-(3-phenylthiophen-2-yl)-4,7-dihydrotetrazolo[1,5-a]pyrimidine-6-carboxylate |

TABLE 9-continued

| ID (PT-nnn) | Name of Compound |
|---|---|
| PT-354 | benzyl 5-methyl-7-(4'-(methylsulfonyl)biphenyl-2-yl)-4,7-dihydrotetrazolo[1,5-a]pyrimidine-6-carboxylate |
| PT-360 | benzyl 5-methyl-7-(4'-morpholinobiphenyl-2-yl)-4,7-dihydrotetrazolo[1,5-a]pyrimidine-6-carboxylate |
| PT-361 | benzyl 5-methyl-7-(4'-nitrobiphenyl-2-yl)-4,7-dihydrotetrazolo[1,5-a]pyrimidine-6-carboxylate |
| PT-366 | benzyl 6-methyl-4-(4'-(methylsulfonamido)biphenyl-2-yl)-4,7-dihydro-1H-pyrazolo[3,4-b]pyridine-5-carboxylate |
| PT-375 | benzyl 7-(2-(2-aminopyrimidin-5-yl)phenyl)-5-methyl-4,7-dihydrotetrazolo[1,5-a]pyrimidine-6-carboxylate |
| PT-376 | benzyl 7-(2-(3,5-dimethylisoxazol-4-yl)phenyl)-5-methyl-4,7-dihydrotetrazolo[1,5-a]pyrimidine-6-carboxylate |
| PT-379 | benzyl 7-(2-(4-methoxyphenyl)benzo[b]thiophen-3-yl)-5-methyl-4,7-dihydrotetrazolo[1,5-a]pyrimidine-6-carboxylate |
| PT-388 | benzyl 7-(2'-carbamoylbiphenyl-2-yl)-5-methyl-4,7-dihydrotetrazolo[1,5-a]pyrimidine-6-carboxylate |
| PT-390 | benzyl 7-(2'-cyanobiphenyl-2-yl)-5-methyl-4,7-dihydrotetrazolo[1,5-a]pyrimidine-6-carboxylate |
| PT-396 | benzyl 7-(3-(4-fluorophenyl)furan-2-yl)-5-methyl-4,7-dihydrotetrazolo[1,5-a]pyrimidine-6-carboxylate |
| PT-397 | benzyl 7-(3-(4-fluorophenyl)thiophen-2-yl)-5-methyl-4,7-dihydrotetrazolo[1,5-a]pyrimidine-6-carboxylate |
| PT-399 | benzyl 7-(3'-aminobiphenyl-2-yl)-5-methyl-4,7-dihydrotetrazolo[1,5-a]pyrimidine-6-carboxylate |
| PT-407 | benzyl 7-(4'-(benzyloxy)biphenyl-2-yl)-5-methyl-4,7-dihydrotetrazolo[1,5-a]pyrimidine-6-carboxylate |
| PT-413 | benzyl 7-(4'-(tert-butoxycarbonyl)biphenyl-2-yl)-5-methyl-4,7-dihydrotetrazolo[1,5-a]pyrimidine-6-carboxylate |
| PT-415 | benzyl 7-(4'-acetylbiphenyl-2-yl)-5-methyl-4,7-dihydrotetrazolo[1,5-a]pyrimidine-6-carboxylate |
| PT-420 | benzyl 7-(4'-methoxybiphenyl-2-yl)-5-methyl-4,7-dihydrotetrazolo[1,5-a]pyrimidine-6-carboxylate |
| PT-427 | diethyl 2,6-dimethyl-4-(2-((2S)-5-methyltetrahydrothiophen-2-yl)phenyl)-1,4-dihydropyridine-3,5-dicarboxylate |
| PT-428 | diethyl 2,6-dimethyl-4-(4'-(methylsulfonamido)biphenyl-2-yl)-1,4-dihydropyridine-3,5-dicarboxylate |
| PT-435 | diethyl 4-(3'-cyanobiphenyl-2-yl)-2,6-dimethyl-1,4-dihydropyridine-3,5-dicarboxylate |
| PT-451 | ethyl 4-(3'-acetylbiphenyl-2-yl)-6-methyl-4,7-dihydro-1H-pyrazolo[3,4-b]pyridine-5-carboxylate |
| PT-455 | ethyl 4-(4'-carbamoylbiphenyl-2-yl)-2-methyl-5-oxo-1,4,5,6,7,8-hexahydroquinoline-3-carboxylate |
| PT-471 | ethyl 6-methyl-4-(4'-(methylsulfonamido)biphenyl-2-yl)-4,7-dihydro-1H-pyrazolo[3,4-b]pyridine-5-carboxylate |
| PT-496 | ethyl 7-(3-(3-fluorophenyl)thiophen-2-yl)-5-methyl-4,7-dihydrotetrazolo[1,5-a]pyrimidine-6-carboxylate |
| PT-499 | ethyl 7-(3'-cyanobiphenyl-2-yl)-5-methyl-4,7-dihydrotetrazolo[1,5-a]pyrimidine-6-carboxylate |
| PT-503 | ethyl 7-(4'-cyanobiphenyl-2-yl)-5-methyl-4,7-dihydrotetrazolo[1,5-a]pyrimidine-6-carboxylate |
| PT-505 | H-indol-5-yl)phenyl)-5-methyl-4,7-dihydrotetrazolo[1,5-a]pyrimidine-6-carboxylate |

Given a desired product, such as for example set out in the above table, the necessary starting materials generally may be determined by inspection, based on the general procedure set out in Example 1A.

Example 10E

Preparation of a Compounds Using Suzuki Coupling Procedure to Modify a Halo-Aryl Group Similarly, by essentially following the procedures set out in Examples 10A, 10B and 10C above, but optionally replacing the starting material, i.e. the compound of Formulas (I)-(VI) that has a halo substituent on an aromatic ring, with another compound of Formulas (I)-(VI) that has a halo substituent on an aromatic ring, and/or optionally replacing the aryl-boronic acid with another aryl-boronic acids, further compounds of Formula (I) may be prepared.

Example 11

Further Preparation of Compounds of Formula (I)

Example 11A

Preparation of a Compound of Formula (I) Varying R1

Compounds of Formula (I) in which the Q2 group is >N—H (i.e. R1 is —H) may be made as described in Examples 1-10 and elsewhere herein and then may be modified to change the identity of the R1 group. An example is given here:

Synthesis of benzyl 4,5-dimethyl-7-(naphthalen-1-yl)-4,7-dihydrotetrazolo[1,5-a]pyrimidine-6-carboxylate (PT-195)

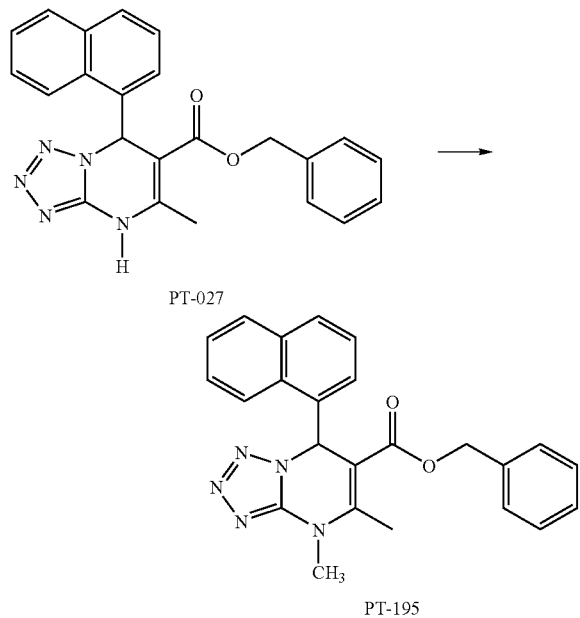

Dissolve PT-027 (397 mg; 1.0 mmole) in dry THF (5 ml) at room temperature. Methyl iodide was then added (0.62 ml; 10.0 mmole) followed by sodium hydride (60% in oil; 200 mg; 5.0 mmole). Let stir at room temperature for 12 h. Dilute reaction with ethyl acetate and transfer to a separatory funnel and washed with saturated NaHCO$_3$ then brine. The organic phase is dried over MgSO$_4$, filtered then evaporated in vacuo. The compound is then purified on a silica gel column (20 g) using 1:1 ethyl acetate:hexanes eluent to provide PT-195 (Rf=0.25) 293 mg (71%) as white powder. H$^1$ NMR 400 MHz (CDCl$_3$) 8.5 (d, J=8.2 Hz, 1H); 7.9-7.8 (m, 2H); 7.6-7.3 (m, 3H); 7.12 (t, J=7.5 Hz, 1H); 7.0 (appt, J=7.5 Hz, 2H); 6.62 (appd, J=7.4 Hz, 2H); 4.84 (s, 2H); 3.7 (s, 3H); 2.8 (s, 3H). MS CI 412 (M+H) and 845 (2M+H).

Similarly, by essentially following the procedures set out in this example above, but optionally replacing the methyl iodide with another alkyl halide compound (e.g. R—X wherein R is optionally substituted lower alkyl and X is a halide, such as chloro, bromo, or iodo) and/or optionally replacing the PT-027 compound with another compound of Formula (I) in which the Q2 group is >N—H, further compounds of Formula (I) may be prepared.

Example 11B

Preparation of a Compound of Formula (I) Varying R1

Similarly, by essentially following the procedures described above in Example 11A, other examples of Compounds of Formula (I) in which the R1 group is varied may be made. The compounds in the following table were made by essentially following the procedures described above in Example 11A, with modifications described below.

TABLE 10

| ID (PT-nnn) | Name of Compound |
|---|---|
| PT-257 | 2-(6-(benzyloxycarbonyl)-5-methyl-7-(naphthalen-1-yl)tetrazolo[1,5-a]pyrimidin-4(7H)-yl)acetic acid |
| PT-258 | 2-(6-(ethoxycarbonyl)-5-methyl-7-(naphthalen-1-yl)tetrazolo[1,5-a]pyrimidin-4(7H)-yl)acetic acid |
| PT-331 | benzyl 4-(2-ethoxy-2-oxoethyl)-5-methyl-7-(naphthalen-1-yl)-4,7-dihydrotetrazolo[1,5-a]pyrimidine-6-carboxylate |
| PT-337 | benzyl 4-(cyanomethyl)-5-methyl-7-(naphthalen-1-yl)-4,7-dihydrotetrazolo[1,5-a]pyrimidine-6-carboxylate |
| PT-449 | ethyl 4-(2-ethoxy-2-oxoethyl)-5-methyl-7-(naphthalen-1-yl)-4,7-dihydrotetrazolo[1,5-a]pyrimidine-6-carboxylate |
| PT-456 | ethyl 4-(cyanomethyl)-5-methyl-7-(naphthalen-1-yl)-4,7-dihydrotetrazolo[1,5-a]pyrimidine-6-carboxylate |
| PT-490 | ethyl 7-(2-bromophenyl)-4-(2-(2,6-dimethylphenylamino)-2-oxoethyl)-5-methyl-4,7-dihydrotetrazolo[1,5-a]pyrimidine-6-carboxylate |

The parent compound (the compound of Formula (I) in which the Q2 group is >N—H) was first prepared as described in Examples 1-10 and elsewhere herein. The parent compound (1.0 mmole) was then dissolved in dry DMF (5 ml) at room temperature. The (optionally substituted) alkyl halide compound was then added (10.0 mmole). Various examples of alkyl halide compounds employed included bromoacetonitrile (for product in which R1 is —CH$_2$—CN); t-butyl bromoacetate (for product in which R1 is —CH$_2$—C(O)O-t-Bu); ethyl bromoacetate (for product in which R1 is —CH$_2$—C(O)O-Et); 2-chloro-N-(2,6-dimethylphenyl)acetamide (for product in which R1 is —CH$_2$—C(O)—NH-(2,6-dimethylphenyl). Addition of the alkyl halide compound was followed by addition of potassium t-butoxide (5.0 mmole). The mixture was stirred at room temperature for 12 h. Dilute reaction with ethyl acetate and transfer to a separatory funnel and washed with saturated NaHCO$_3$ then brine. The organic phase is dried over MgSO$_4$, filtered then evaporated in vacuo. The compound is then purified on a silica gel column (20 g), typically using 1:1 ethyl acetate:hexanes eluent to provide the product compound of Formula (I). In a variation of the synthesis, for product compounds in which the R1 group includes a carboxylic acid group, the corresponding t-butyl ester is first prepared as described in this Example, and the t-butyl ester is then hydrolysed, for example in aqueous HCl, to provide the product compound. It should be noted that, throughout many of the Examples (e.g. Examples 1-10, and also elsewhere herein) when a compound of the invention (e.g. of Formula (I) or as otherwise described herein) has a carboxylic acid group as part of its structure, the preparation of the compound may proceed by first forming a carboxylic ester, followed by cleavage of the ester, e.g. by hydrolysis in aqueous acid or by saponification.

Given a desired product, such as for example set out in the above table, the necessary starting materials generally may be determined by inspection, based on the general procedure set out in Example 11A and 11B.

Similarly, by essentially following the procedures set out in this example above, but optionally replacing the alkyl halide compound with another (optionally substituted) alkyl halide compound and/or optionally replacing the parent compound with another compound of Formula (I) in which the Q2 group is >N—H, further compounds of Formula (I) may be prepared.

Example 12

Further Preparation of Compounds of Formula (I)

Example 12A

Preparation of a Compound of Formula (I) with a Pendant Tetrazolo Substituent Compounds of Formulas (I)-(VI) that have cyano substituents (e.g. on aryl or heteroaryl rings of R4 or R5, or as a substituent on an alkyl group, or elsewhere in the molecule) may be made as described above in Examples 1-11 and elsewhere herein. These compounds having cyano-substituents may then be modified as described in this example to convert the cyano substituent into a tetrazolo group using sodium azide. An example is given here.

Synthesis of 4-(1H-tetrazol-5-yl)benzyl 5-methyl-7-(naphthalen-1-yl)-4,7-dihydrotetrazolo[1,5-a]pyrimidine-6-carboxylate (PT-060)

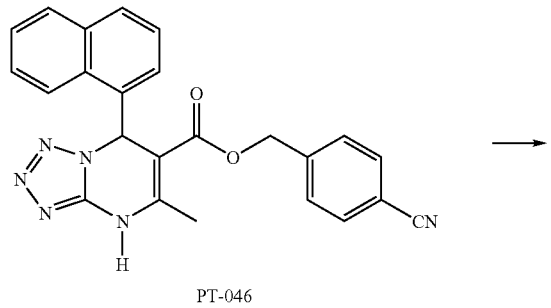

PT-046

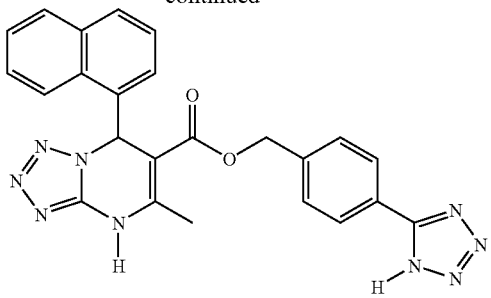

PT-060

Dissolve PT-046 (100 mg; 0.23 mmole) in dry DME (3 ml). Add sodium azide (150 mg; 2.3 mmole) followed by triethylamine hydrochloride (315 mg; 2.3 mmole). The mixture is heated at 85° C. for 15 h. The reaction is cooled to room temperature and water is then added (15 ml). A precipitate comes out of solution and is then filtered. The powder is then dried on a high vacuum for 12 h to provide PT-060 (60 mg; 57%) as a white powder. $H^1$ NMR 400 MHz (DMSO-D6) 8.6 (bs, 1H); 8.0-6.5 (m, 12H); 4.96 (d, J=13.3 Hz, 1H); 4.82 (d, J=13.3 Hz, 1H); 2.6 (s, 3H). MS CI 466 (M+H); 931 (2M+H).

Example 12B

Preparation of a Compound of Formula (I) with a Pendant Tetrazolo Substituent Compounds of Formulas (I)-(VI) that have cyano substituents (e.g. on aryl or heteroaryl rings of R4 or R5, or as a substituent on an alkyl group, or elsewhere in the molecule) may be made as described above in Examples 1-11 and elsewhere herein. These compounds having cyano-substituents may then be modified as described in this example to convert the cyano substituent into a tetrazolo group using sodium azide.

By essentially following the procedures set out in Example 12A above, but optionally replacing the PT-046 compound with another compound of Formulas (I)-(VI) that has a cyano substituent (e.g. on aryl or heteroaryl rings of R4 or R5, or as a substituent on an alkyl group, or elsewhere in the molecule) and has the necessary substituents to result in the indicated products, the following compounds of Formula (I) were prepared:

TABLE 11

| ID (PT-nnn) | Name of Comopound |
|---|---|
| PT-060 | 4-(1H-tetrazol-5-yl)benzyl 5-methyl-7-(naphthalen-1-yl)-4,7-dihydrotetrazolo[1,5-a]pyrimidine-6-carboxylate |
| PT-247 | 2-(1H-tetrazol-5-yl)ethyl 5-methyl-7-(naphthalen-1-yl)-4,7-dihydrotetrazolo[1,5-a]pyrimidine-6-carboxylate |
| PT-271 | 3-(1H-tetrazol-5-yl)benzyl 5-methyl-7-(naphthalen-1-yl)-4,7-dihydrotetrazolo[1,5-a]pyrimidine-6-carboxylate |
| PT-326 | benzyl 4-((1H-tetrazol-5-yl)methyl)-5-methyl-7-(naphthalen-1-yl)-4,7-dihydrotetrazolo[1,5-a]pyrimidine-6-carboxylate |
| PT-393 | benzyl 7-(2-methoxy-4-(1H-tetrazol-5-yl)phenyl)-5-methyl-4,7-dihydrotetrazolo[1,5-a]pyrimidine-6-carboxylate |
| PT-403 | benzyl 7-(4-(1H-tetrazol-5-yl)phenyl)-5-methyl-4,7-dihydrotetrazolo[1,5-a]pyrimidine-6-carboxylate |
| PT-444 | ethyl 4-((1H-tetrazol-5-yl)methyl)-5-methyl-7-(naphthalen-1-yl)-4,7-dihydrotetrazolo[1,5-a]pyrimidine-6-carboxylate |
| PT-481 | ethyl 7-(2-(4-(1H-tetrazol-5-yl)phenoxy)phenyl)-5-methyl-4,7-dihydrotetrazolo[1,5-a]pyrimidine-6-carboxylate |
| PT-493 | ethyl 7-(3'-(1H-tetrazol-5-yl)biphenyl-2-yl)-5-methyl-4,7-dihydrotetrazolo[1,5-a]pyrimidine-6-carboxylate |
| PT-500 | ethyl 7-(4'-(1H-tetrazol-5-yl)biphenyl-2-yl)-5-methyl-4,7-dihydrotetrazolo[1,5-a]pyrimidine-6-carboxylate |

Given a desired product, such as for example set out in the above table, the necessary starting materials generally may be determined by inspection, based on the general procedure set out in Example 12A.

Similarly, by essentially following the procedures set out in Examples 12A and 12B above, but optionally replacing the initial compound that has the cyano substituent with another compound of Formulas (I)-(VI) that has a cyano substituent (e.g. on aryl or heteroaryl rings of R4 or R5, or as a substituent on an alkyl group, or elsewhere in the molecule), further compounds of Formula (II) may be prepared.

Additional Examples

The following additional examples further exemplify the preparation of compounds of the present invention.

Example 13

Synthesis of benzyl 5-methyl-7-(3-phenoxyphenyl)-4,7-dihydrotetrazolo[1,5-a]pyrimidine-6-carboxylate (PT-024)

The 5-aminotetrazole (850 mg; 10.0 mmole) was dissolved in hot ethanol (25 ml) with triethylamine (1.8 mmole; 0.25 ml). When all solids were dissolved (about ten minutes of heating at 82° C.), 3-phenoxybenzaldehyde (1.73 ml; 10.0 mmole) was added followed by benzylacetoacetate (1.72 ml; 10.0 mmole). The clear solution was maintained at reflux for 15 h. A white precipitate had filled the flask and the mixture was cooled to room temperature at which time it was filtered and the material washed with ethanol then ethyl ether to provide the desired product (2.5 g; 57%) as a white powder.

$^1$H NMR (400 MHz; CDCl$_3$) d 7.34-7.20 (m, 7H); 7.14-7.08 (m, 3H); 7.06-6.80 (m, 2H); 6.96-6.86 (m, 3H); 6.70 (s, 1H); 5.12 (d, 1H, J=12.3 Hz); 5.05 (d, 1H, J=12.3 Hz); 2.7 (s, 3H). LC MS shows MH+ at 440 and 2 MH+ at 879.

Example 14

Synthesis of 1,2,3,4-tetrahydronaphthalen-1-yl 5-methyl-7-(naphthalen-1-yl)-4,7-dihydrotetrazolo[1,5-a]pyrimidine-6-carboxylate (PT-001)

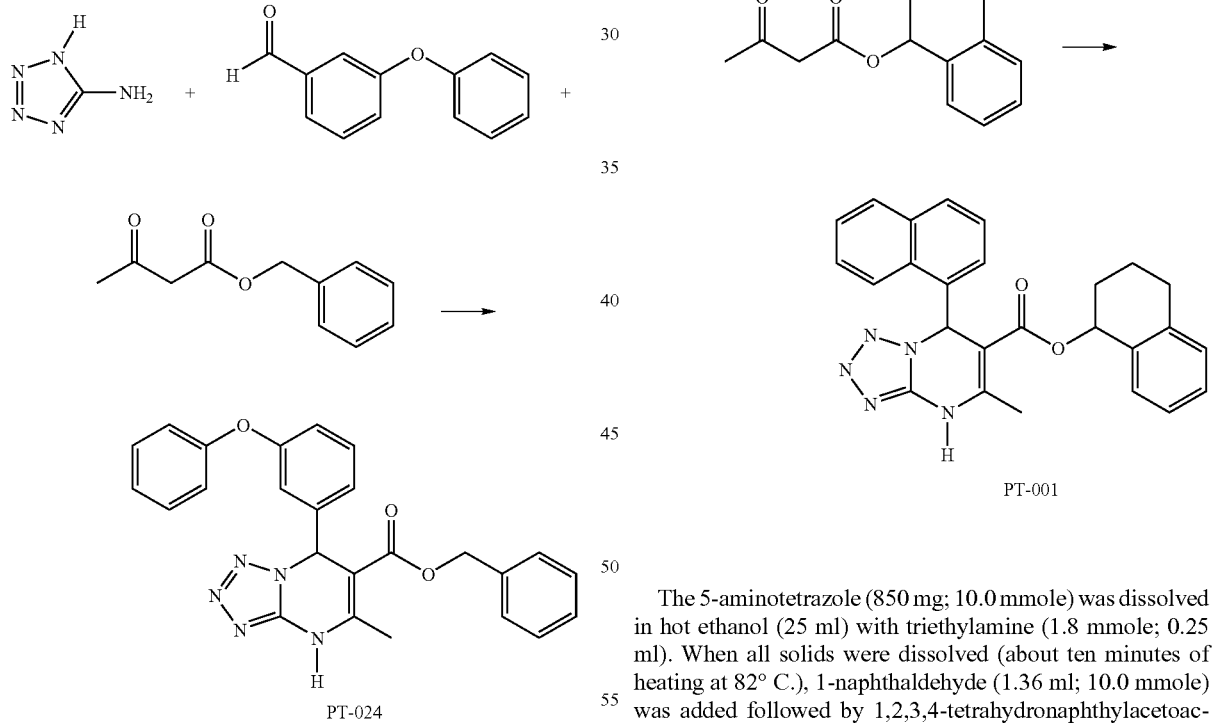

The 5-aminotetrazole (850 mg; 10.0 mmole) was dissolved in hot ethanol (25 ml) with triethylamine (1.8 mmole; 0.25 ml). When all solids were dissolved (about ten minutes of heating at 82° C.), 1-naphthaldehyde (1.36 ml; 10.0 mmole) was added followed by 1,2,3,4-tetrahydronaphthylacetoacetate (2.32 g; 10.0 mmole). The clear solution was maintained at reflux for 15 h at which time a white precipitate was noted. The mixture was cooled to room temperature and filtered; the material was then washed with ethanol then ethyl ether to provide the desired product (1.9 g; 43%) as a white powder.
$^1$H NMR (400 MHz; CDCl$_3$; a 1:1 mixture of diastereomers) d 11.01 (s, 1H); 10.96 (s, 1H); 8.4 (d, 1H, J=7.4 Hz); 8.22 (d, 1H, J=7.8 Hz); 7.90-7.68 (m, 4H); 7.52-7.10 (m, 7H); 6.98-6.7 (m, 3H); 6.42-6.34 (m, 1H); 6.08 (d, 1H, J=7.0 Hz); 5.77 (bs, 2H); 2.77 (s, 3H); 2.76 (s, 3H); 2.50-0.5 (m, 14H). LC MS shows MH+ at 438 and 2 MH+ at 875

Example 15

Synthesis of ethyl 5-methyl-7-(3-methylbenzo[b]thiophen-2-yl)-4,7-dihydrotetrazolo[1,5-a]pyrimidine-6-carboxylate (PT-018)

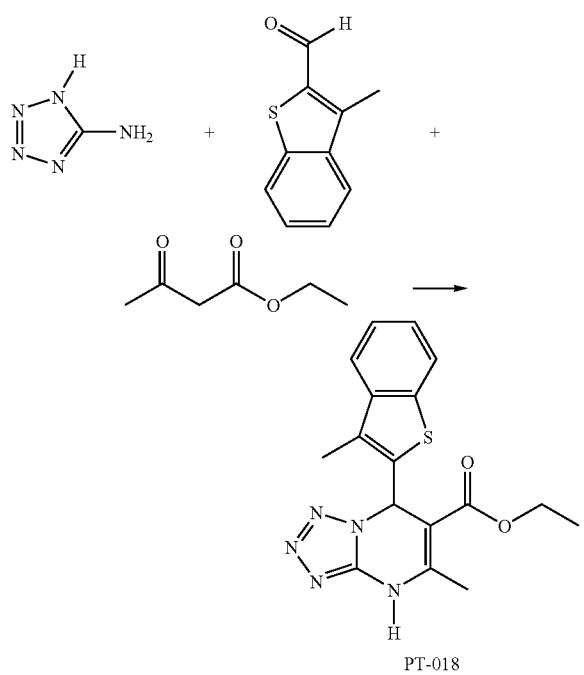

PT-018

The 5-aminotetrazole (850 mg; 10.0 mmole) was dissolved in hot ethanol (25 ml) with triethylamine (1.8 mmole; 0.25 ml). When all solids were dissolved (about ten minutes of heating at 82° C.), 3-methyl-2-benzothiophenecarboxaldehyde (1.76 g; 10.0 mmole) was added followed by ethylacetoacetate (1.28 ml; 10.0 mmole). The clear solution was maintained at reflux for 15 h. At which time a white precipitate had filled the flask and the mixture was cooled to room temperature where it was filtered and the material washed with ethanol then ethyl ether to provide the desired product (1.42 g; 41%) as a white powder. $^1$H NMR (400 MHz; CDCl$_3$) d 11.2 (bs, 1H); 7.73 (d, 1H, J=7.8 Hz); 7.69 (d, 1H, J=7.8 Hz); 7.39 (ddd, 1H, J=7.0, 7.0, 0.78 Hz); 7.32 (ddd, 1H, J=8.2, 7.0, 1.5 Hz); 4.17-4.05 (m, 2H); 2.71 (s, 3H); 2.69 (s, 3H); 1.14 (at, J=7.0 Hz). LC MS shows MH+ at 356 and 2 MH+ at 711.

Example 16

Synthesis of ethyl 5-methyl-7-(naphthalen-1-yl)-4,7-dihydrotetrazolo[1,5-a]pyrimidine-6-carboxylate (PT-192)

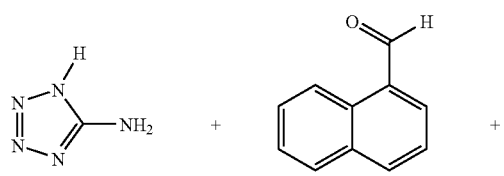

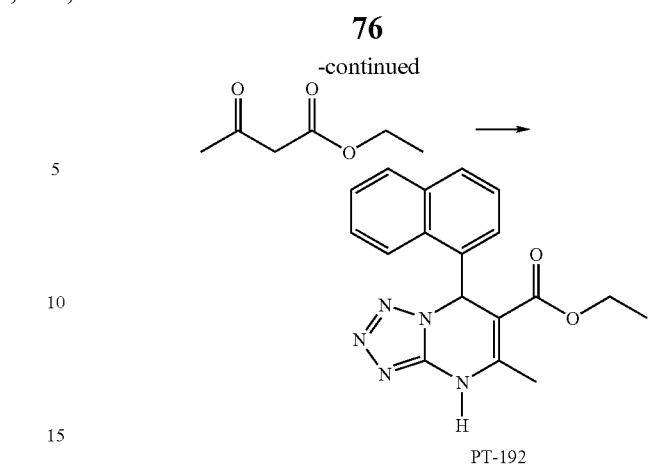

PT-192

To a solution of 5-aminotetrazole (0.85 g, 10.0 mmole) and triethylamine (0.25 ml, 1.8 mmole) in hot ethanol (25 ml) was added 1-naphthaldehyde (1.36 ml, 10.0 mmole) followed by ethyl acetoacetate (1.28 ml, 10.0 mmole). The clear solution was heated at reflux for 15 h at which time a white powdery precipitate was observed. The mixture was cooled to room temperature, filtered and washed with ethanol and ethyl ether to provide the desired product (1.88 g, 56%) as a white powder. $^1$H NMR (400 MHz; CDCl$_3$) d 11.0 (s, 1H); 8.6 (d, 1H, J=8.6 Hz); 7.9 (d, 1H, J=8.2 Hz); 7.82 (d, 1H, J=7.8 Hz); 7.68 (at, 1H, J=7.4 Hz); 7.6-7.54 (m, 2H); 7.45 (dd, 1H, J=7.4, 1.1 Hz); 7.40 (at, 1H, J=7.8 Hz); 3.9 (q, 2H, J=7.0 Hz); 2.75 (s, 3H); 0.8 (t, 3H, J=7.0 Hz). LC MS shows MH+ at 336; M+Na at 358; 2M+H at 671 and 2M+Na at 693.

Example 17

Synthesis of 3-(furan-2-yl)-4-(naphthalen-1-yl)-7,8-dihydro-1H-furo[3,4-e]pyrazolo[3,4-b]pyridin-5(4H)-one (PT-080)

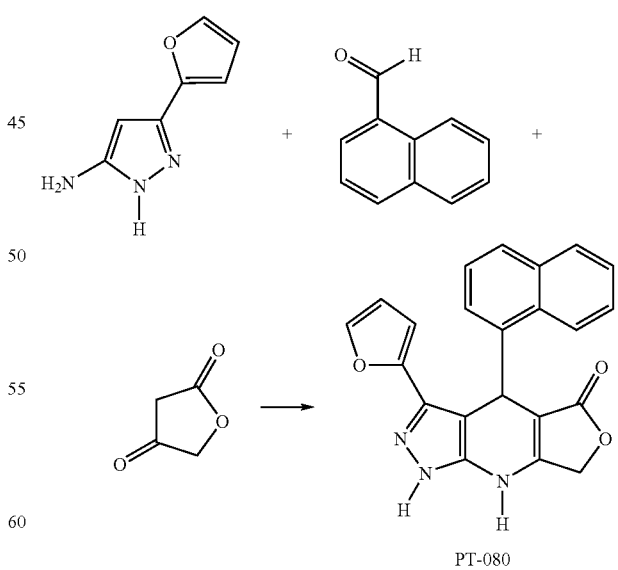

PT-080

To a solution of 1H-2-amino-4-(2-yl-furan)pyrazole (746 mg, 5.0 mmole) in ethanol (15 ml) at 82° C. was added triethylamine (0.2 ml, 1.4 mmole) followed by 1-naphthaldehyde (0.682 ml, 5.0 mmole) and then tetronic acid (0.50 g, 5.0 mmole). The clear solution mixture was maintained at reflux for 15 h. A precipitate had formed and the mixture was cooled to room temperature. The mixture was filtered and washed with ethanol and ethyl ether to provide the desired product (1.38 g, 75%) as a white powder. $^1$H NMR (400 MHz; DMSO-d6) d 12.7 (bs, 1H); 10.47 (bs, 1H); 7.80 (d, 1H, J=9.3 Hz); 7.72 (d, 1H, J=8.6 Hz); 7.60-7.40 (bs, m, 2H); 7.40-7.20 (m, 5H); 7.38 (at, 1H, J=7.4 Hz); 6.30 (bs, 1H); 6.1 (bs, 1H); 5.9 (bs, 1H); 4.87 (s, 2H). LC MS shows MH+ at 370 and 2MH+ at 739.

Example 18

Synthesis of ethyl 2-chloro-6-methoxy-2'-methyl-5'-oxo-1',4',5',6',7',8'-hexahydro-3,4'-biquinoline-3'-carboxylate (PT-188)

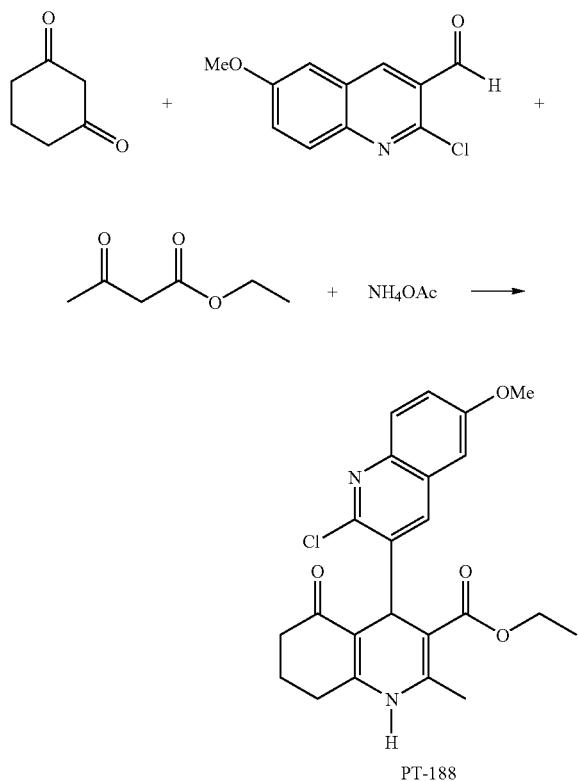

To a solution of 1,3-cyclohexanedione (0.56 g, 5.0 mmole) in hot ethanol (10 ml) was added 2-chloro-6-methoxy-3-quinolinecarboxaldehyde (1.1 g, 5.0 mmole) followed by ethyl acetoacetate (0.64 ml, 5.0 mmole) and finally ammonium acetate (0.77 g, 10.0 mmole). The mixture was refluxed for 12 h at which time a precipitate was observed. The reaction was cooled to room temperature, filtered and washed with ethanol then ethyl ether to provide the desired product (1.36 g, 64%) as a golden powder. $^1$H NMR (400 MHz; CDCl$_3$) d 8.14 (s, 1H); 7.81 (d, 1H, J=8.9 Hz); 7.28 (dd, 1H, J=8.9, 2.7 Hz); 7.06 (d, 1H, J=2.7 Hz); 6.58 (bs, 1H); 5.48 (s, 1H); 4.10-3.95 (m, 2H); 3.89 (s, 3H); 2.42 (at, 2H, J=6.5 Hz); 2.35 (s, 3H); 2.28 (at, 2H, J=6.5 Hz); 2.0-1.80 (m, 2H); 1.13 (t, 3H, J=7.0 Hz). LC MS shows MH+ at 427 and 2M+Na at 875.

Example 19

Synthesis of isopropyl 2,7,7-trimethyl-5-oxo-4-(3-(4-(trifluoromethyl)phenyl)-1H-pyrazol-4-yl)-1,4,5,6,7,8-hexahydroquinoline-3-carboxylate (PT-160)

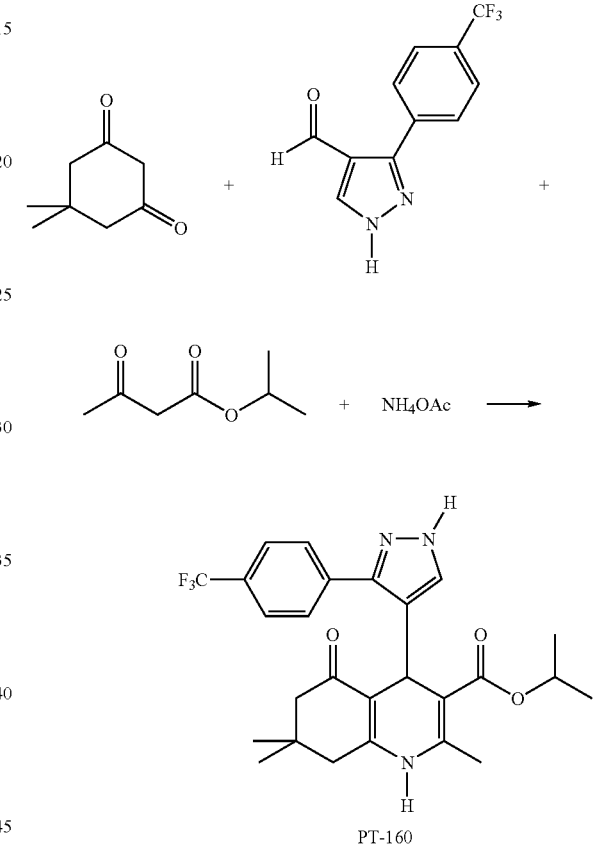

To a solution of dimedone (0.984 g, 4.1 mmole) in hot ethanol (12 ml) was added 3-(4-trifluoromethylphenyl)-4-pyrazolecarboxaldehyde (1.0 g, 4.1 mmole), isopropyl acetoacetate (0.6 ml, 4.1 mmole) and lastly ammonium acetate (0.616 g, 8.0 mmole). The mixture was maintained at reflux for 18 h. No precipitate formed from the reaction. The reaction mixture was stripped of the ethanol in vacuo. The crude material was dissolved in ethyl acetate and washed with water (2×) and the organic phase was separated and stripped in vacuo. The material was then dissolved in ethyl ether and after a few minutes a white precipitate started to form. The white suspension was then filtered over night as it was a slow viscous filtration. The white material was washed with more ether to provide the desired product (1.55 g, 78%) as a white powder. Rf=0.45 in ethyl acetate. $^1$H NMR (400 MHz; DMSO d6) d 9.14 (bs, 1H); 8.34 (bd, 2H, J=7.4 Hz); 7.8 (bs, 2H); 7.35 (bs, 1H); 5.05 (bs, 1H); 4.65-4.55 (m, 1H); 3.35 (bs, 1H); 2.52 (bs, 1H); 2.46 (d, 1H, J=16.8 Hz); 2.32 (d, 1H, J=16.8 Hz); 2.23 (s, 3H); 2.20 (d, 1H, J=16.0 Hz); 2.04 (d, 1H, J=16.0 Hz); 1.05 (s, 3H); 0.93 (s, 3H); 0.7 (d, 3H, J=6.2 Hz); 0.55 (s, 3H, J=6.2 Hz). LC MS shows MH+ at 488; 2M+H at 975.

Example 20

Synthesis of diisopropyl 4-(3-(4-fluorophenyl)-1H-pyrazol-4-yl)-2,6-dimethyl-1,4-dihydropyridine-3,5-dicarboxylate (PT-128)

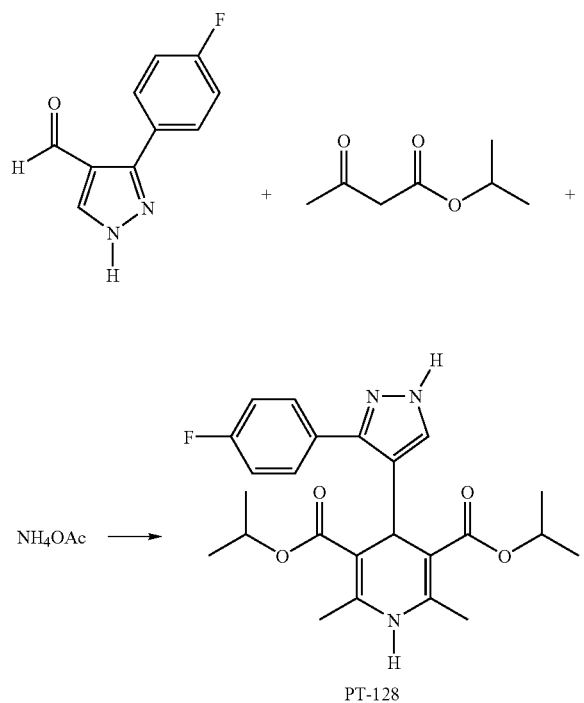

Solution of isopropyl acetoacetate (1.51 ml, 10.4 mmole) in hot ethanol (20 ml) was added 3-(4-fluorophenyl)-4-1H-pyrazolecarboxaldehyde (1.0 g, 5.2 mmole) followed by the ammonium acetate (0.77 g. 10.0 mmole). The mixture was refluxed for 15 h. No precipitate formed. The reaction mixture was reduced in vacuo and dissolved in ethyl acetate. The organic phase was washed with water (2×), decanted and concentrated in vacuo. This material was purified on 150 g SiO₂ flash column using 50% ethyl acetate:hexanes as eluent. Rf=0.29 in 1:1 ethyl acetate:hexanes. ¹H NMR (400 MHz; CDCl₃) d 7.72-7.64 (m, 2H); 7.44 (s, 1H); 7.14-7.08 (m, 2H); 5.43 (s, 1H); 5.16 (s, 1H); 4.98-4.86 (m, 2H); 2.18 (s, 6H); 1.12 (d, 6H, J=6.3 Hz); 1.0 (d, 6H, J=6.3 Hz). LC MS shows MH+ at 442; M+Na at 464 and 2M+H at 883.

Example 21

Synthesis of (4'-(methoxycarbonyl)biphenyl-4-yl) methyl 5-methyl-7-(naphthalen-1-yl)-4,7-dihydrotetrazolo[1,5-a]pyrimidine-6-carboxylate (PT-200)

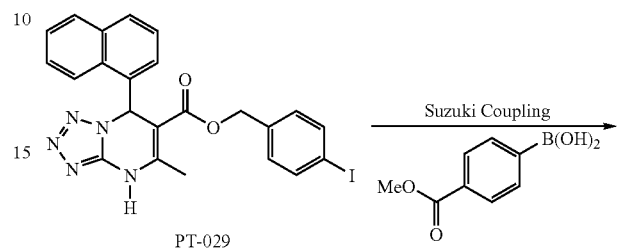

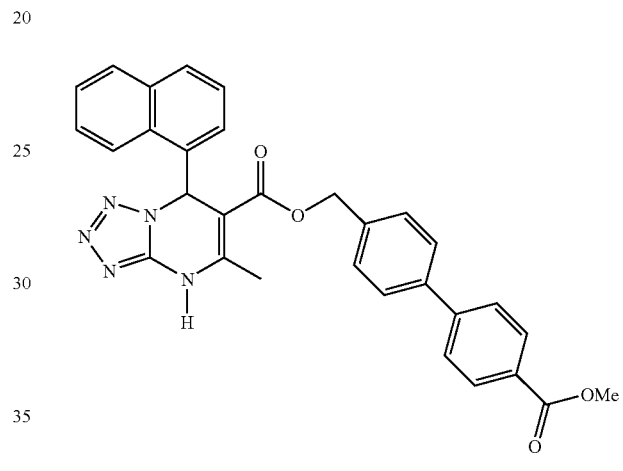

The procedure in Example 10A was followed (same scale) except using para-methoxycarbonylphenylboronic acid as the coupling partner to provide the PT-200 product in 21% yield.

Example 22

Synthesis of 2-(5-methyl-7-(naphthalen-1-yl)-4,7-dihydrotetrazolo[1,5-a]pyrimidin-6-yl)-5-phenyl-1,3,4-oxadiazole (PT-200)

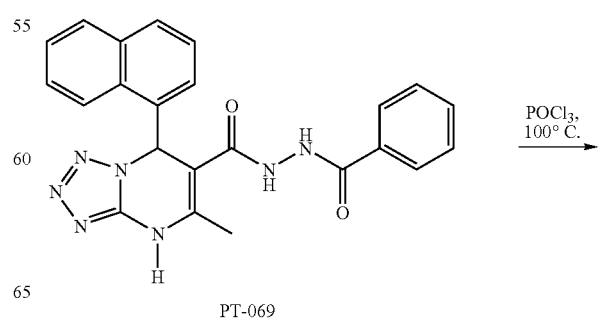

81

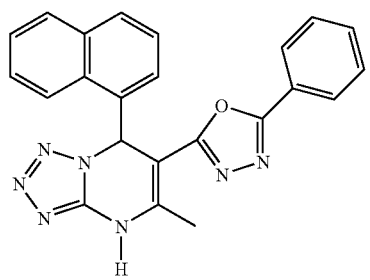

PT-203

Procedure: Compound A (735 mg, 1.7276 mmol) was dissolved in $POCl_3$ (6.0 ml, 65.27 mmol) and heated at 100° C. overnight. In 15 h LCMS showed the disappearance of A and formation of B as the major component (81%, tr 5.2 m). The mixture was cooled to room temperature, and the majority of the liquid was removed in vacuo. Ethyl acetate (30 ml) added, and the mixture was then poured into 2M $Na_2CO_3$ (30 ml) at 0° C. and stirred for 30 min. A grey suspension formed between the aqueous and organic phases. An insoluble solid was recovered by filtration and was washed with $H_2O$ (100 ml), cold EtOAc (10 ml), and then dried in vacuo to afford a grey solid B (350 mg, 50%). LCMS mz 408.2 (M+H). $^1$HNMR (DMSO-$D_6$) matched the desired structure. Analytical HPLC>97% purity.

The filtrate was extracted with EtOAc (2×50 ml), and the combined organic phase was washed with 30% $NH_4Cl$ (2×40 ml), brined (60 ml), dried over $Na_2SO_4$, and concentrated to give brown gel-like solid (ca. 320 mg, including 90% of B).

Similarly, by essentially following the procedures set out in this Example above, but replacing the starting material with another compound of Formulas (I)-(VI) that has a —C(O)—NH—NH—C(O)— moiety, further compounds of present invention may be prepared. Examples are listed in the following Table:

TABLE 12

| ID (PT-nnn) | Name of Compound |
|---|---|
| PT-203 | 2-(5-methyl-7-(naphthalen-1-yl)-4,7-dihydrotetrazolo[1,5-a]pyrimidin-6-yl)-5-phenyl-1,3,4-oxadiazole |
| PT-252 | 2-(5-methyl-7-(naphthalen-1-yl)-4,7-dihydrotetrazolo[1,5-a]pyrimidin-6-yl)-5-phenethyl-1,3,4-oxadiazole |
| PT-261 | 2-benzyl-5-(5-methyl-7-(naphthalen-1-yl)-4,7-dihydrotetrazolo[1,5-a]pyrimidin-6-yl)-1,3,4-oxadiazole |
| PT-267 | 2-methyl-5-(5-methyl-7-(naphthalen-1-yl)-4,7-dihydrotetrazolo[1,5-a]pyrimidin-6-yl)-1,3,4-oxadiazole |
| PT-276 | 3-(5-benzyl-1,3,4-oxadiazol-2-yl)-2-methyl-4-(naphthalen-1-yl)-4,6,7,8-tetrahydroquinolin-5(1H)-one |

82

Example 23

Synthesis of diethyl 2,6-dimethyl-4-(naphthalen-1-yl)pyridine-3,5-dicarboxylate (PT-193)

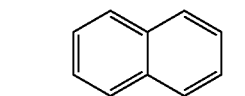

PT-108

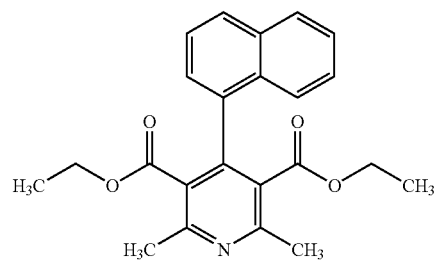

PT-193

To a solution of PT-108 (0.379 g, 1.0 mmole) in toluene (5.0 ml) at 80° C. was added DDQ (2,3-dichloro-5,6-dicyanoquinone; 0.340 g, 1.5 mmole) all at once. The mixture is heated for 1 h and then the toluene is removed in vacuo. The crude reaction was then applied to 25 g SiO2 flash column using 30% ethyl acetate:hexanes eluent, Rf=0.29. This provided the desired product (0.139 g, 37%) as a light pinkish oil. $^1$H NMR (400 MHz; $CDCl_3$) d 7.9-7.8 (m, 2H); 7.5-7.38 (m, 4H); 7.3-7.25 (m, 1H); 3.76-3.64 (m, 4H); 2.66 (s, 6H); 0.45 (t, 6H, J=7.4 Hz). LC MS shows MH+ at 378.

Similarly, by essentially following the procedures set out in this Example above, but replacing the starting material with another compound of Formulas (I)-(VI) that has a dihydropyridine moiety, further compounds of present invention may be prepared. Examples are listed in the following Table:

TABLE 13

| ID (PT-nnn) | Name of Compound |
|---|---|
| PT-193 | diethyl 2,6-dimethyl-4-(naphthalen-1-yl)pyridine-3,5-dicarboxylate |
| PT-324 | benzyl 2-methyl-5-oxo-4-phenyl-5,6,7,8-tetrahydroquinoline-3-carboxylate |
| PT-371 | benzyl 6-methyl-4-phenyl-1H-pyrazolo[3,4-b]pyridine-5-carboxylate |
| PT-450 | ethyl 4-(3'-acetylbiphenyl-2-yl)-6-methyl-1H-pyrazolo[3,4-b]pyridine-5-carboxylate |
| PT-472 | ethyl 6-methyl-4-(naphthalene-1-yl)-1H-pyrazolo[3,4-b]pyridine-5-carboxylate |
| PT-474 | ethyl 6-methyl-4-phenyl-1H-pyrazolo[3,4-b]pyridine-5-carboxylate |

Example 24

Synthesis of 12-(naphthalen-1-yl)-5,6,7,12-tetrahydrobenzo[f]tetrazolo[5,1-b]quinazoline (PT-198)

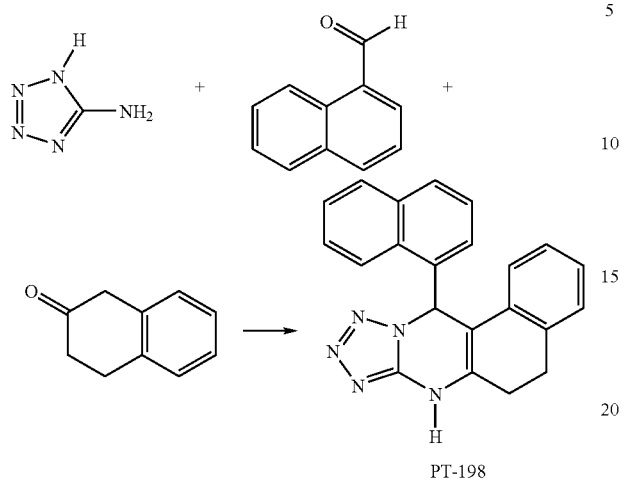

PT-198

To a solution of 5-aminotetrazole (0.850 g, 10.0 mmole) and triethylamine (0.250 ml, 1.8 mmole) in hot ethanol (25 ml) was added 1-naphthaldehyde (1.36 ml, 10.0 mmole) followed by 2-tetralone (1.32 ml, 10.0 mmole). The mixture is refluxed for 72 h after which time a small amount of powdery precipitate is observed. Upon cooling the reaction to room temperature, it was filtered and washed with ethyl ether to provide the desired product (0.189 g, 5.1%) as a tan powder. $^1$H NMR (400 MHz; DMSO-d6) d 10.9 (bs, 1H); 9.0 (bs, 1H); 8.05-7.85 (m, 2H); 7.77 (at, 1H, J=7.0 Hz); 7.65 (at, 2H, J=7.0 Hz); 7.42 (at, 1H, J=7.4 Hz); 7.14 (d, 1H, J=7.4 Hz); 7.0-6.75 (m, 3H); 3.0-2.6 (m, 4H). LC MS shows MH+ at 352; 2M+H at 703 and 2M+Na at 725.

Further Examples

TABLE 14 list of further compounds of the invention

| ID (PT-nnn) | Name of Compound |
|---|---|
| PT-015 | ethyl 4,5-dimethyl-7-(naphthalen-1-yl)-4,7-dihydrotetrazolo[1,5-a]pyrimidine-6-carboxylate |
| PT-066 | (5-methyl-7-(naphthalen-1-yl)-4,7-dihydrotetrazolo[1,5-a]pyrimidin-6-yl)(4-phenylpiperidin-1-yl)methanone |
| PT-070 | 5-methyl-7-(naphthalen-1-yl)-N-((R)-1-phenylethyl)-4,7-dihydrotetrazolo[1,5-a]pyrimidine-6-carboxamide |
| PT-092 | ethyl 6-amino-5-cyano-4-(furan-2-yl)-2-methyl-4H-pyran-3-carboxylate |
| PT-095 | 2-amino-4-(4-bromophenyl)-5-oxo-1,4,5,6,7,8-hexahydroquinoline-3-carbonitrile |
| PT-133 | 4-(3-(ethoxycarbonyl)-7,7-dimethyl-5-oxo-2-propyl-1,4,5,6,7,8-hexahydroquinolin-4-yl)benzoic acid |
| PT-185 | 3-ethyl 5-methyl 2-((2-aminoethoxy)methyl)-4-(2-chlorophenyl)-6-methyl-1,4-dihydropyridine-3,5-dicarboxylate |
| PT-186 | 7-amino-5-(4-bromophenyl)-1,3-dimethyl-2,4-dioxo-2,3,4,5-tetrahydro-1H-pyrano[2,3-d]pyrimidine-6-carbonitrile |
| PT-195 | benzyl 4,5-dimethyl-7-(naphthalen-1-yl)-4,7-dihydrotetrazolo[1,5-a]pyrimidine-6-carboxylate |
| PT-198 | 12-(naphthalen-1-yl)-5,6,7,12-tetrahydrobenzo[f]tetrazolo[5,1-b]quinazoline |
| PT-272 | 3-(2-(6-(ethoxycarbonyl)-5-methyl-4,7-dihydrotetrazolo[1,5-a]pyrimidin-7-yl)phenoxy)benzoic acid |
| PT-274 | 3-(3-(6-(ethoxycarbonyl)-5-methyl-4,7-dihydrotetrazolo[1,5-a]pyrimidin-7-yl)phenoxy)benzoic acid |
| PT-291 | 4-(2-(6-(ethoxycarbonyl)-5-methyl-4,7-dihydrotetrazolo[1,5-a]pyrimidin-7-yl)phenoxy)benzoic acid |
| PT-295 | 4-(3-(6-(ethoxycarbonyl)-5-methyl-4,7-dihydrotetrazolo[1,5-a]pyrimidin-7-yl)phenoxy)benzoic acid |
| PT-321 | benzyl 2-methyl-4-phenyl-1,4-dihydroquinoline-3-carboxylate |
| PT-338 | benzyl 5-(2-(dimethylamino)ethyl)-7-(naphthalen-1-yl)-4,7-dihydrotetrazolo[1,5-a]pyrimidine-6-carboxylate |
| PT-378 | benzyl 7-(2-(4-(ethylsulfonyl)piperazin-1-yl)-6-methoxyphenyl)-5-methyl-4,7-dihydrotetrazolo[1,5-a]pyrimidine-6-carboxylate |
| PT-404 | benzyl 7-(4'-(1-hydroxyethyl)biphenyl-2-yl)-5-methyl-4,7-dihydrotetrazolo[1,5-a]pyrimidine-6-carboxylate |
| PT-465 | ethyl 6-acetyl-7-(naphthalen-1-yl)-4,7-dihydrotetrazolo[1,5-a]pyrimidine-5-carboxylate |
| PT-479 | ethyl 7-(2-(3-(ethoxycarbonyl)phenoxy)phenyl)-5-methyl-4,7-dihydrotetrazolo[1,5-a]pyrimidine-6-carboxylate |
| PT-483 | ethyl 7-(2-(4-(ethoxycarbonyl)phenoxy)phenyl)-5-methyl-4,7-dihydrotetrazolo[1,5-a]pyrimidine-6-carboxylate |
| PT-494 | ethyl 7-(3-(3-(ethoxycarbonyl)phenoxy)phenyl)-5-methyl-4,7-dihydrotetrazolo[1,5-a]pyrimidine-6-carboxylate |
| PT-204 | ethyl 6-methyl-2-oxo-4-(thiophen-2-yl)-1,2,3,4-tetrahydropyrimidine-5-carboxylate |
| PT-205 | 5-(5-(ethoxycarbonyl)-6-methyl-2-oxo-1,2,3,4-tetrahydropyrimidin-4-yl)thiophene-2-carboxylic acid |
| PT-206 | ethyl 4-(5-bromothiophen-2-yl)-6-methyl-2-oxo-1,2,3,4-tetrahydropyrimidine-5-carboxylate |

TABLE 14-continued list of further compounds of the invention

| ID (PT-nnn) | Name of Compound |
|---|---|
| PT-207 | ethyl 4-(5-ethylthiophen-2-yl)-6-methyl-2-oxo-1,2,3,4-tetrahydropyrimidine-5-carboxylate |
| PT-208 | ethyl 6-methyl-2-oxo-4-(thiophen-3-yl)-1,2,3,4-tetrahydropyrimidine-5-carboxylate |
| PT-209 | ethyl 2-oxo-6-propyl-4-(5-(2-(trifluoromethyl)phenyl)furan-2-yl)-1,2,3,4-tetrahydropyrimidine-5-carboxylate |
| PT-210 | ethyl 4-(furan-3-yl)-2-oxo-6-propyl-1,2,3,4-tetrahydropyrimidine-5-carboxylate |
| PT-211 | ethyl 4-(5-ethylfuran-2-yl)-2-oxo-6-propyl-1,2,3,4-tetrahydropyrimidine-5-carboxylate |
| PT-212 | ethyl 4-(5-bromothiophen-2-yl)-2-oxo-6-propyl-1,2,3,4-tetrahydropyrimidine-5-carboxylate |
| PT-213 | 5-(5-(ethoxycarbonyl)-2-oxo-6-propyl-1,2,3,4-tetrahydropyrimidin-4-yl)thiophene-2-carboxylic acid |
| PT-214 | ethyl 2-oxo-4-(5-phenylthiophen-2-yl)-6-propyl-1,2,3,4-tetrahydropyrimidine-5-carboxylate |
| PT-215 | ethyl 4-(5-ethylthiophen-2-yl)-2-oxo-6-propyl-1,2,3,4-tetrahydropyrimidine-5-carboxylate |
| PT-216 | 2-methoxyethyl 6-methyl-2-oxo-4-(4-phenoxyphenyl)-1,2,3,4-tetrahydropyrimidine-5-carboxylate |
| PT-217 | ethyl 4-(benzo[b]thiophen-3-yl)-6-ethyl-2-oxo-1,2,3,4-tetrahydropyrimidine-5-carboxylate |
| PT-218 | ethyl 6-ethyl-4-(3-methylbenzo[b]thiophen-2-yl)-2-oxo-1,2,3,4-tetrahydropyrimidine-5-carboxylate |
| PT-219 | ethyl 4-(benzofuran-2-yl)-6-ethyl-2-oxo-1,2,3,4-tetrahydropyrimidine-5-carboxylate |
| PT-220 | 3-methyl-4-(naphthalen-1-yl)-4,5-dihydro-1H-pyrazolo[3,4-b]pyridin-6(7H)-one |
| PT-221 | 4-(naphthalen-1-yl)-1-phenyl-4,5-dihydro-1H-pyrazolo[3,4-b]pyridin-6(7H)-one |
| PT-222 | 3,3'-(naphthalen-1-ylmethylene)bis(4-hydroxyfuran-2(5H)-one) |

The example compounds were synthesized using methods disclosed herein or methods which will be readily apparent given the disclosure herein and methods well known in the art. A list of such example compounds is given in Tables accompanying the Examples. In typical embodiments, the present invention includes a compound listed in the Tables accompanying the Examples (e.g. Tables 1-14. For ease of reference herein, each compound in the Tables has an assigned identifier ("PT-nnn"), and the compounds may be referred to herein by the identifier.

Testing

Activity testing is conducted in the Examples below using methods described herein and those well known in the art.

Sodium Current Screening Assays:

The late sodium current (Late INa) and peak sodium current (Peak INa) assays are performed on an automated electrophysiology platform, PatchXpress 7000A (MDS Analytical Technologies, Sunnyvale, Calif.), which uses the whole cell patch clamp technique to measure currents through the cell membrane of up to 16 cells at a time. The assay uses an HEK293 (human embryonic kidney) cell line heterologously expressing the wild-type human cardiac sodium channel, hNa$_v$1.5, purchased from Millipore (Billerica, Mass.). No beta subunits were coexpressed with the Na channel alpha subunit. Cells are maintained with standard tissue culture procedures and stable channel expression is maintained with 400 µg/ml Geneticin in the culture medium. Cells isolated for use on PatchXpress are incubated for 5 minutes in Versene 1× and then for 2 minutes in 0.0125% Trypsin-EDTA (both at 37° C.) to ensure that 80-90% of the cells are single and not part of a cell cluster. Experiments are carried out at 24-27° C.

For both the Late INa and Peak INa assays, series resistance compensation is set to 50% and whole-cell compensation is performed automatically. Currents are low-pass filtered at 10 kHz and digitized at 31.25 kHz. Currents through open sodium channels are automatically recorded and stored in the DataXpress2 database (MDS Analytical Technologies, Sunnyvale, Calif.). Analysis is performed using DataXpress2 analysis software and data are compiled in Excel.

Compound stocks are routinely made in glass vials to 10 mM in dimethyl sulfoxide (DMSO). In some cases, when compounds are not soluble in DMSO, they are made in 100% ethanol. Stocks are sonicated as necessary. The extracellular solution for screening Late INa is composed of: 140 mM NaCl, 4 mM KCl, 1.8 mM CaCl$_2$, 0.75 mM MgCl$_2$, and 5 mM HEPES with pH adjusted to 7.4 using NaOH. The extracellular solution for screening Peak INa is composed of: 20 mM NaCl, 120 mM N-methyl-D glucamine, 4 mM KCl, 1.8 mM CaCl$_2$, 0.75 mM MgCl$_2$, and 5 mM HEPES with pH adjusted to 7A using HCl. The intracellular solution used to perfuse the inside of the cells for both the Late INa and Peak INa assays contains: 120 mM CsF, 20 mM CsCl, 5 mM EGTA, 5 mM HEPES and pH adjusted to 7.4 with CsOH. Compounds are diluted in extracellular solution to 10 µM in glass vials and then transferred to glass well plates before robotic addition to the cells. The 0Na extracellular solution used at the end of each experiment for the Late INa and Peak INa assays to measure baseline current contains: 140 mM N-methyl-D-glucamine; 4 mM KCl; 1.8 mM CaCl$_2$; 0.75 mM MgCl$_2$; 5 mM HEPES and pH was adjusted to 7.4 with HCl.

Late INa Screening Assay:

For the Late INa assay, sodium channels are activated every 10 seconds (0.1 Hz) by depolarizing the cell membrane to −20 mV for 250 milliseconds (ms) from a holding potential of −120 mV. In response to a −20 mV voltage step, typical Na$_v$1.5 sodium currents activate rapidly to a peak negative current and then inactivate nearly completely within 3-4 ms (see FIG. 1).

Figure 2:
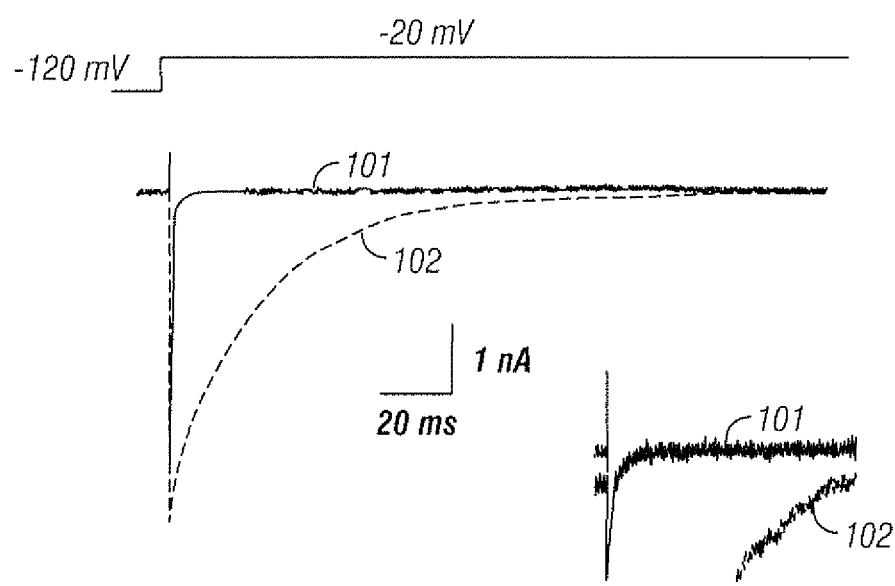
FIG. 2 is a plot of sodium current measured with and without Tefluthrin.

All compounds are tested to determine their activity in blocking the late sodium current. Late INa current is generated by adding 10 µM Tefluthrin (pyrethroid) to the extracellular solution while recording Na currents. In FIG. 2 the black traces (designated by the arrow, 101) are Na current measured before addition of Tefluthrin and the gray traces (designated by the arrow, 102) are measured after Tefluthrin addition. For some experiments, 50 nM ATX II (sea anemone toxin), another late INa activator, was used to generate the late component. Both activators generate late components that are large enough that block of the late component by compounds can be measured easily. For the purposes of the screening, late INa is defined as the mean current between 225 ms and 250 ms after stepping to −20 mV to activate Na channels. After establishing the whole cell recording configuration, late INa activators are added to each well 4 times over a 16-17 minute period so that the late component of the Na current reaches a stable value. Compounds are then added (typically at 10 µM), in the presence of late INa activator, with 3 additions over the course of 7 or 8 minutes. Measurements are made typically at the end of exposure to the third compound addition. Baseline current in the absence of $Na^+$ ions is measured at the end of each experiment (after two additions of 0Na solution—see above) and is used to calculate the percent block by compound.

Peak INa Screening Assay:

Compounds were also evaluated for their effect in several other assays, including their effect on Peak INa. In some cases, the effect on Peak INa was measured using data from the Late INa assay. However, peak currents were often too large to make this possible, requiring a separate assay to evaluate the effect on peak INa. Since the peak INa can be very large, introducing artifacts in the recording, the concentration of $Na^+$ in the bath is reduced to 20 mM and a nonpermeant cation is added to compensate for the $Na^+$ that was omitted from the standard extracellular solution (see above). The peak INa assay uses a holding potential of −100 mV and a 20 ms test pulse to 0 mV to activate the channel. As in the Late INa assay, stepping the voltage to 0 mV causes a rapid increase in negative Na current through hNav1.5 that inactivates within a few ms. No late INa activator is added for the peak assay.

Figure 6:
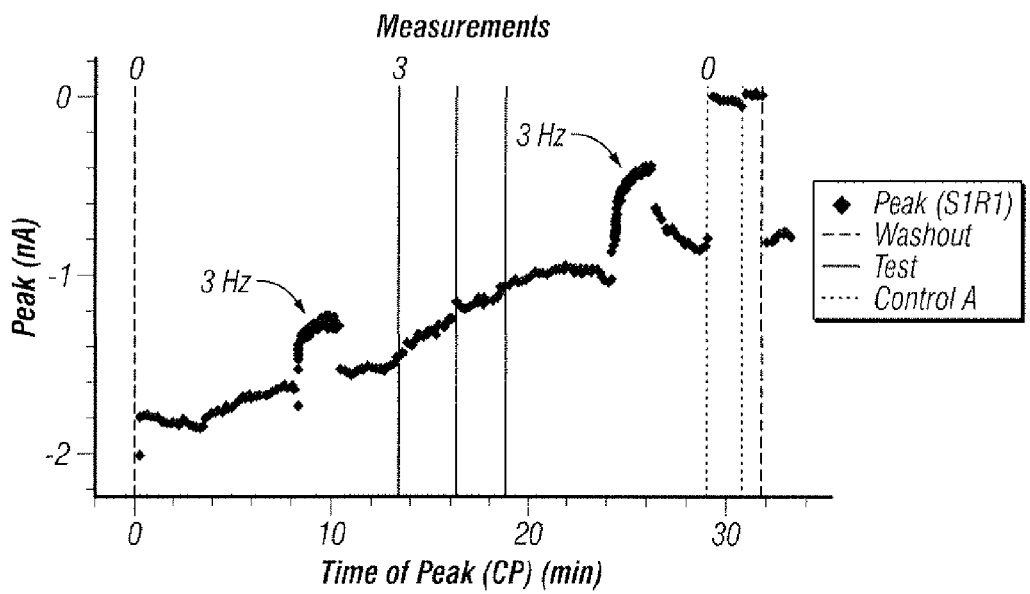
FIG. 6 shows peak INa plotted as a function of experiment time. Stimulation at 3 Hz is indicated. Calculation of UDB corrects for the decrease in peak in the absence of test compound.

For the separate peak INa assay, both tonic (TB) block and use-dependent (UDB) block of peak inward sodium current by 10 µM compound are determined. TB is block of the channel in the resting state, before the channel opens. TB is simulated in this assay by stimulating the channel to open at a low frequency (0.1 Hz). This is done in order to measure the control current amplitude and monitor current rundown, enabling correction for rundown in the calculation of percent block for TB. UDB is measured by stimulating the channel to open at a higher frequency (3 Hz) and is used to determine accumulated block in activated states by compound. Activating the channel at this higher frequency typically also decreases the peak current some even in the absence of compound. Therefore, the assay is designed to measure the use-dependent decrease in peak both in the absence and in the presence of compound, and the calculation of UDB corrects the decrease in current measured in the presence of compound for the decrease in current in the absence of compound (FIG. 6).

After establishing the whole cell recording configuration, currents are allowed to stabilize for 6-10 minutes while channels are activated briefly at 0.1 Hz. This is followed by a 2 minute stimulation at 3 Hz and then a 2 minute stimulation at 0.1 Hz before addition of compound. Compound is added 3 times over a period of 2 to 3 minutes and channels are exposed to compound for 8 to 9 minutes before another round of high frequency stimulation at 3 Hz for 2 minutes. As with the late INa assay, 0Na extracellular solution is added two times at the end to establish the baseline current and demonstrate the quality of solution exchange and the recording.

hERG Screening Assay:

Compounds were screened to test their activity in blocking the hERG potassium channel. The hERG channel is heterologously expressed in a CHO (Chinese Hamster Ovary) cell line. Cells are maintained with standard tissue culture procedures and stable channel expression is maintained with 500 µg/ml G418 in the culture medium. Cells are harvested for testing on the PatchXpress automated patch clamp with Accumax (Innovative Cell Technologies, San Diego, Calif.) to isolate single cells.

Figure 3:
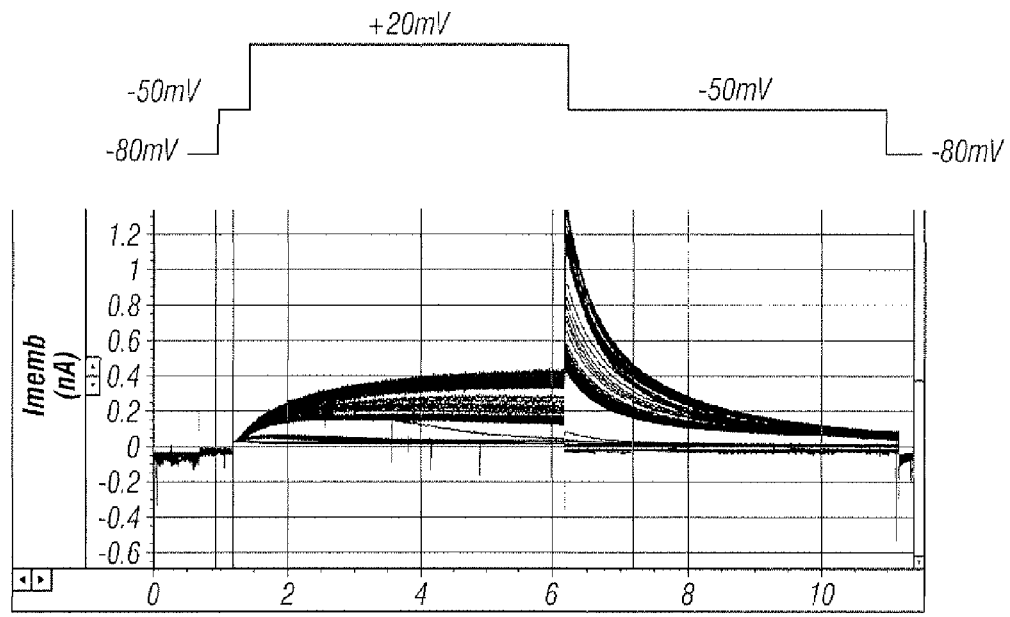
FIG. 3 illustrates hERG channel activation upon application of the indicated potential.

The following solutions are used for electrophysiological recordings. The external solution contains: 2 mM $CaCl_2$; 2 mM $MgCl_2$; 4 mM KCl; 150 mM NaCl; 10 mM Glucose; 10 mM HEPES (pH 7.4 with 1M NaOH, osmolarity). The internal solution contains: 140 mM KCl, 10 mM $MgCl_2$, 6 mM EGTA, 5 mM HEPES, 5 mM ATP (pH adjusted to 7.25 with KOH).

hERG channels are activated when the voltage is stepped to +20 mV from the −80 mV holding potential (see FIG. 3). During a 5 second step at +20 mV, the channels activate and then largely inactivate, so the currents are relatively small. Upon returning to −50 mV from +20 mV, hERG currents transiently become much larger as inactivation is rapidly removed and then the channel closes. The first step to −50 mV for 300 ms is used as a baseline for measuring the peak amplitude during the step to −50 mV after channel activation. The peak current at −50 mV is measured both under control conditions and after addition of compound.

All compounds are prepared as 10 mM DMSO stocks in glass vials. Stock solutions are mixed by vigorous vortexing and sonication for about 2 minutes at room temperature. For testing, compounds are diluted in glass vials using an intermediate dilution step in pure DMSO and then further diluted to working concentrations in external solution. Dilutions are prepared no longer than 20 minutes before use.

After achieving the whole-cell configuration, cells are monitored for 90 seconds to assess stability and washed with external solution for 66 seconds. The voltage protocol described above is then applied to the cells every 12 seconds and throughout the whole procedure. Only cells with stable recording parameters and meeting specified health criteria are allowed to enter the compound addition procedure.

External solution containing 0.1% DMSO (vehicle) is applied to the cells first to establish the control peak current amplitude. After allowing the current to stabilize for 3 to 5 minutes, 1 µM and then 10 µM test compounds are applied. Each compound concentration is added 4 times and cells are kept in test solution until the effect of the compound reaches steady state or for a maximum of 12 minutes. After addition of test compound, a positive control (1 µM Cisapride) is added and must block >95% of the current for the experiment to be considered valid. Washout in the external solution compartment is performed until the recovery of the current reaches steady state. Data are analyzed using DataXpress, Clampfit (Molecular Devices, Inc., Sunnyvale) and Origin 7 (Originlab Corp.)

L-type Calcium Channel Activity Well-Plate Assay:

Cell Culture: IMR-32 (human neuroblastoma) cells were obtained from The American Type Culture Collection. The cells were maintained in MEM supplemented with 10% fetal bovine serum, 2 mM of L-glutamine, 100 IU/ml of penicillin, 50 µg/ml of streptomycin, 1% of sodium pyruvate, 1% of sodium bicarbonate and 1% of non-essential amino acid. The cells were cultured at 37° C. in a humidified 5% $CO_2$/95% air incubator. Culture medium was changed every two days and cells were recultivated when they reached 70-80% confluent.

Figure 4:
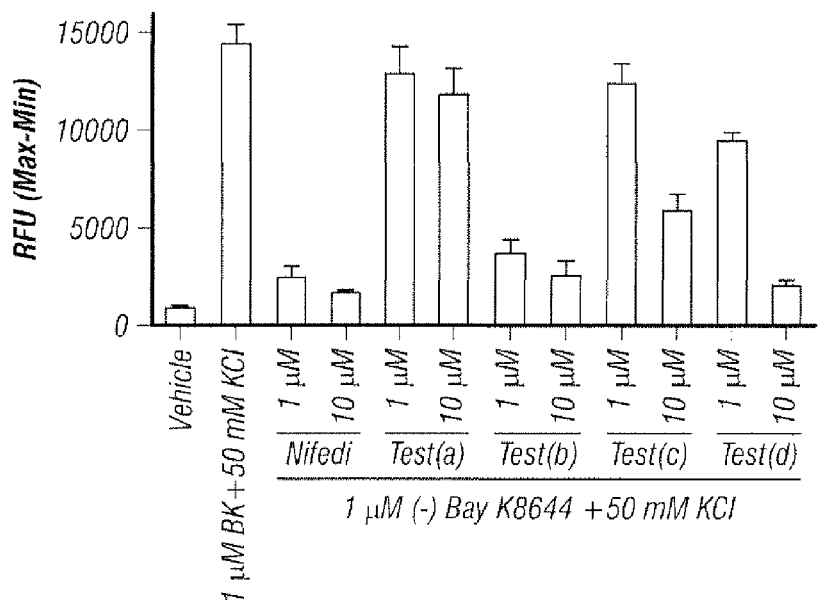
FIG. 4 shows inhibition of L-type calcium channel activity.

Assay: IMR-32 cells were seeded on a Microtest 96-well Assay Plate (BD FALCON™) at a density of 200,000 cells/well in 200 μl culture medium for overnight. The culture medium was removed, and replaced by 120 μl Ca-4 dye (MDS Analytical Technologies, Sunnyvale, Calif.) in HBSS (1× Hank's Balanced Salt solution plus 20 mM HEPES, pH 7.4) containing 2 mM probenecid. Cells were then incubated for 1 hour at 37° in incubator. Testing compounds were diluted from 5 μM-50 μM in HBSS, and 40 μl were added in cells before assay. L-type calcium channel activities (Max−Min) were measured after addition of 40 μl of 1 μM (−)Bay K 8644 plus 50 mM KCl (final concentration) using FlexStation (Molecular Devices) immediately after addition of testing compounds. The inhibition of L-type calcium channel activity by compounds was then calculated. FIG. 4 shows results of the assay for four compounds tested and the controls. The four compounds were Test(a)—PT-163; Test(b)—PT-108; Test(c)—PT-181; and Test(d)—PT-113.

Compounds were tested using the described assay methods. Data are shown in Table 15. Data are shown for results obtained by testing the listed compounds at a concentration of 10 μM in the late INa and Peak INa assays, and at 1 μM and 10 μM for the hERG and L-type calcium channel assays.

TABLE 15

Assay results

| ID (PT-nnn) | Late INa % blk | Tonic Peak INa % blk | UDB Peak INa % blk | hERG Patch Clamp hERG % blk | hERG Patch Clamp hERG % blk | CaL Plate Assay 1 μM % blk | CaL Plate Assay 10 μM % blk |
|---|---|---|---|---|---|---|---|
| PT-001 | 28.8 | | | | | | |
| PT-002 | 53.1 | 2.4 | | 11.5 | 28.0 | | |
| PT-003 | 14.5 | | | | | | |
| PT-004 | 25.5 | | | | | | |
| PT-005 | 25.4 | | | | | | |
| PT-006 | 5.4 | | | | | | |
| PT-007 | 44.0 | | | | | | |
| PT-008 | 57.2 | 2.1 | | 10.0 | 33.5 | 0 | 9 |
| PT-009 | 8.2 | | | | | | |
| PT-010 | 36.1 | | | 12.5 | 30.0 | | |
| PT-011 | 37.7 | | | | | | |
| PT-012 | 40.1 | | | | | | |
| PT-013 | 45.4 | | | | | | |
| PT-014 | 50.9 | 9.0 | | | | 0 | 40 |
| PT-015 | 27.2 | | | | | | |
| PT-016 | 30.7 | | | | | | |
| PT-017 | 45.9 | | | 10.0 | 23.5 | | |
| PT-018 | 36.5 | | | 14.5 | 36.5 | | |
| PT-019 | 35.7 | | | 10.0 | 26.0 | | |
| PT-020 | 47.7 | | | | | | |
| PT-021 | 48.2 | | | 13.0 | 43.5 | | |
| PT-022 | 26.0 | | | | | | |
| PT-023 | 32.8 | | | | | | |
| PT-024 | 72.6 | | | | | | |
| PT-025 | 78.8 | | | 11.0 | 53.0 | | |
| PT-026 | 10.3 | | | | | | |
| PT-027 | 74.9 | 29.7 | 6.8 | 14.0 | 64.5 | 0 | 0 |
| PT-028 | 23.1 | | | | | | |
| PT-029 | 52.1 | | | | | | |
| PT-030 | 66.5 | | | 10.5 | 34.5 | | |
| PT-031 | 28.6 | | | | | | |
| PT-032 | 63.6 | 11.5 | | 19.0 | 50.5 | | |
| PT-033 | 23.3 | | | | | | |
| PT-034 | 52.4 | | | 14.5 | 56.0 | | |
| PT-035 | 44.0 | | | | | | |
| PT-036 | 41.0 | | | | | | |
| PT-037 | 34.4 | | | | | | |
| PT-038 | 11.9 | | | | | | |
| PT-039 | 82.1 | | | 10.0 | 27.5 | 2 | 0 |
| PT-040 | 70.8 | 9.9 | | 14.5 | 24.5 | 0 | 18 |
| PT-041 | 41.4 | | | | | | |
| PT-042 | 76.5 | | | 11.0 | 52.5 | 0 | 16 |
| PT-043 | 53.8 | | | | | 23 | 60 |
| PT-044 | 70.7 | | | 16.5 | 40.0 | 7 | 35 |
| PT-045 | 92.0 | 23.8 | | 10.0 | 70.0 | 0 | 98 |
| PT-046 | 67.0 | | | | | | |
| PT-047 | 67.4 | 36.3 | | | | 24 | 42 |
| PT-048 | 90.8 | 58.6 | | | | 0 | 74 |
| PT-049 | 35.4 | | | | | | |
| PT-050 | 94.0 | | | 10.0 | 53.5 | | |
| PT-052 | 9.1 | | | | | | |
| PT-053 | 53.6 | | | | | | |
| PT-054 | 72.4 | | | | | | |
| PT-055 | 56.3 | 7.6 | | | | | |
| PT-056 | 7.8 | | | | | | |
| PT-057 | 71.0 | | | | | | |
| PT-058 | 71.4 | | | | | | |
| PT-059 | 57.7 | | | 10.0 | 66.5 | | |
| PT-060 | 5.6 | | | | | | |
| PT-061 | 37.3 | | | 24.0 | 46.5 | | |
| PT-062 | 60.2 | 7.9 | | 14.0 | 51.0 | | |
| PT-063 | 47.5 | | | | | | |
| PT-064 | 79.5 | 7.2 | | 20.5 | 37.5 | | |
| PT-065 | 59.0 | | | | | | |
| PT-066 | 22.2 | | | | | | |
| PT-067 | 24.4 | | | | | | |
| PT-068 | 14.3 | | | 14.0 | 22.5 | | |
| PT-069 | 11.5 | | | | | | |
| PT-070 | 9.9 | | | | | | |
| PT-071 | 16.3 | | | | | | |
| PT-072 | −0.9 | | | | | | |
| PT-073 | −3.2 | | | | | | |
| PT-074 | 27.7 | | | 14.0 | 43.0 | | |
| PT-075 | 26.5 | | | | | | |
| PT-076 | −4.3 | | | | | | |
| PT-077 | −2.6 | | | | | | |
| PT-078 | 46.3 | | | | | | |
| PT-079 | 49.0 | | | 57.5 | 96.5 | | |
| PT-080 | 31.9 | | | | | | |
| PT-081 | 16.6 | | | | | | |
| PT-082 | 43.1 | | | | | | |
| PT-083 | 30.0 | | | | | | |
| PT-084 | 16.9 | | | | | | |
| PT-085 | 9.1 | | | 34.0 | 44.5 | | |
| PT-086 | 38.8 | | | 13.5 | 57.5 | | |
| PT-087 | 16.5 | | | | | | |
| PT-089 | 14.5 | | | | | | |
| PT-091 | 48.4 | | | | | | |
| PT-092 | −0.2 | | | | | | |
| PT-093 | −2.6 | | | | | | |
| PT-095 | 4.9 | | | 10.0 | 24.5 | 0 | 15 |
| PT-096 | 5.5 | −0.4 | | 15.0 | 48.0 | 8 | 39 |
| PT-098 | −27.9 | | | | | | |
| PT-100 | −12.1 | 4.0 | | 10.0 | 16.5 | 0 | 0 |
| PT-101 | 49.3 | 2.9 | | 19.0 | 67.5 | 6 | 47 |
| PT-102 | 44.9 | 2.7 | | | | 6 | 51 |
| PT-104 | 14.3 | | | 18.0 | 46.0 | 0 | 27 |
| PT-107 | 91.9 | 25.9 | | 11.5 | 48.0 | 10 | 44 |
| PT-108 | 93.9 | 2.4 | | 10.0 | 44.6 | 77 | 76 |
| PT-109 | | 18.1 | | 16.0 | 34.2 | 4 | 53 |
| PT-110 | 41.8 | 0.0 | | | | 86 | 88 |
| PT-111 | 69.2 | | | 11.5 | 48.5 | 75 | 79 |
| PT-112 | −24.9 | | | | | | |
| PT-113 | 88.6 | 30.4 | | 11.0 | 57.3 | 18 | 93 |
| PT-114 | 85.0 | 13.1 | | 20.9 | 51.5 | 8 | 15 |
| PT-115 | 86.0 | 17.2 | | | 50.3 | 52 | 65 |
| PT-116 | | | | 22.9 | 66.0 | 6 | 32 |
| PT-117 | 38.9 | | | | | | |
| PT-118 | −3.8 | | | | | | |
| PT-119 | 3.8 | | | | | | |
| PT-120 | 25.7 | | | | | | |
| PT-121 | 54.8 | | | | | 35 | 72 |
| PT-122 | 80.3 | | | 15.5 | 55.0 | 10 | 63 |
| PT-123 | 86.9 | 7.0 | | 10.0 | 30.5 | 59 | 92 |

TABLE 15-continued

Assay results

| ID (PT-nnn) | Late INa % blk | Tonic Peak INa % blk | UDB Peak INa % blk | hERG Patch Clamp | | CaL Plate Assay | |
|---|---|---|---|---|---|---|---|
| | | | | hERG % blk | hERG % blk | 1 µM % blk | 10 µM % blk |
| PT-124 | 86.2 | 58.7 | | 11.5 | 66.0 | 10 | 52 |
| PT-125 | 10.3 | | | | | | |
| PT-126 | −39.0 | | | | | | |
| PT-127 | 1.1 | | | | | | |
| PT-128 | 34.1 | | | | | | |
| PT-129 | 17.6 | | | | | | |
| PT-130 | 15.7 | | | | | | |
| PT-132 | −5.3 | | | | | | |
| PT-133 | −27.5 | | | 10.0 | 12.0 | | |
| PT-134 | 15.5 | | | | | | |
| PT-135 | 59.9 | 9.6 | | | | 24 | 62 |
| PT-136 | 45.2 | | | | | | |
| PT-137 | 25.3 | | | | | | |
| PT-138 | 34.1 | | | | | | |
| PT-139 | 21.8 | | | | | | |
| PT-140 | 6.3 | | | 13.5 | 34.5 | | |
| PT-146 | 31.2 | | | | | | |
| PT-148 | 7.6 | | | | | | |
| PT-149 | 71.5 | | | 24.3 | 67.0 | 4 | 72 |
| PT-150 | 52.9 | | | 28.2 | 49.3 | 4 | 71 |
| PT-151 | 35.0 | | | | | | |
| PT-152 | 41.2 | | | | | | |
| PT-153 | −5.0 | 1.7 | | 10.5 | 13.5 | 3 | 44 |
| PT-156 | 36.6 | | | | | | |
| PT-157 | 62.3 | 15.3 | | 16.0 | 37.1 | 3 | 43 |
| PT-158 | 38.7 | | | | | | |
| PT-159 | 46.3 | | | | | | |
| PT-161 | 6.8 | | | | | | |
| PT-162 | −0.2 | 1.1 | | | | | |
| PT-163 | 974.0 | | | 15.0 | 53.5 | 5 | 17 |
| PT-164 | 32.0 | 10.2 | | | | 20 | 77 |
| PT-165 | 289.0 | | | 30.5 | 64.5 | 0 | 2 |
| PT-166 | 257.0 | | | | | | |
| PT-167 | −10.0 | | | | | | |
| PT-169 | 11.8 | | | | | | |
| PT-170 | 9.8 | | | | | | |
| PT-171 | 20.2 | | | | | | |
| PT-172 | 16.3 | | | | | | |
| PT-173 | 52.6 | 0.0 | | 12.0 | 37.0 | 0 | 26 |
| PT-178 | 0.3 | | | 11.5 | 30.0 | 10 | 2 |
| PT-181 | 91.7 | 76.5 | | 10.5 | 73.0 | 8 | 61 |
| PT-182 | 33.0 | | | | | | |
| PT-183 | 54.0 | | | 10.0 | 10.0 | 0 | 16 |
| PT-187 | −2.6 | | | | | | |
| PT-188 | −0.8 | | | | | | |
| PT-189 | 0.5 | | | | | | |
| PT-190 | 4.2 | | | 10.5 | 32.0 | | |
| PT-191 | 63.2 | 0.0 | | 26.5 | 68.0 | 12 | 37 |
| PT-192 | 52.3 | 0.0 | | 23.0 | 29.0 | 9 | 12 |
| PT-193 | 55.9 | 4.9 | | 16.0 | 72.5 | 0 | 45 |
| PT-194 | 76.1 | 19.1 | | 25.0 | 91.0 | 21 | 61 |
| PT-195 | 52.7 | 1.7 | | 12.5 | 49.0 | 0 | 88 |
| PT-196 | 32.5 | | | | | | |
| PT-197 | 21.5 | | | | | | |
| PT-198 | 50.9 | | | | | | |
| PT-199 | 20.3 | | | | | | |
| PT-200 | 7.4 | | | | | | |
| PT-201 | 7.8 | | | | | | |
| PT-202 | 9.7 | | | | | | |
| PT-203 | 10.9 | | | | | | |
| PT-222 | 15.8 | | | | | | |
| PT-223 | 45.9 | | | | | | |
| PT-235 | 71.4 | 28.1 | | 10.0 | 41.5 | | |
| PT-236 | 68.0 | | | | | | |
| PT-237 | 61.5 | | | 11.5 | 22.5 | | |
| PT-238 | 49.9 | | | | | | |
| PT-239 | 94.8 | | | | | | |
| PT-240 | 85.0 | | | | | | |
| PT-241 | 77.1 | | | | | | |
| PT-242 | 11.0 | | | | | | |
| PT-243 | 91.5 | | | | | | |
| PT-244 | 68.7 | 66.2 | 44.0 | | | | |
| PT-248 | 27.2 | | | | | | |
| PT-249 | 20.0 | | | 11.5 | 15.5 | | |
| PT-250 | 7.6 | | | | | | |
| PT-251 | 11.5 | | | | | | |
| PT-252 | 70.0 | | | 10.5 | 78.0 | | |
| PT-253 | 9.1 | | | | | | |
| PT-254 | 10.7 | | | 15.0 | 20.0 | | |
| PT-255 | 20.6 | | | | | | |
| PT-256 | 25.7 | | | | | | |
| PT-257 | 7.4 | | | | | | |
| PT-258 | 1.6 | | | | | | |
| PT-260 | 74.8 | | | | | | |
| PT-261 | 59.4 | | | | | | |
| PT-262 | 70.0 | 15.1 | 6.9 | | | | |
| PT-263 | 38.8 | | | | | | |
| PT-264 | 53.5 | | | | | | |
| PT-265 | 18.6 | | | | | | |
| PT-266 | 8.8 | | | | | | |
| PT-267 | 17.0 | | | | | | |
| PT-268 | 9.5 | | | | | | |
| PT-269 | 12.3 | | | | | | |
| PT-271 | 5.8 | | | | | | |
| PT-272 | −4.9 | | | | | | |
| PT-273 | 14.1 | | | | | | |
| PT-274 | 16.8 | | | | | | |
| PT-275 | 9.4 | | | | | | |
| PT-276 | 49.7 | 31.3 | 13.0 | | | | |
| PT-277 | 18.0 | | | | | | |
| PT-278 | 63.9 | | | | | | |
| PT-279 | 61.2 | | | 12.5 | 45.0 | | |
| PT-280 | 45.9 | | | 11.5 | 48.0 | | |
| PT-282 | 30.2 | | | | | | |
| PT-283 | 11.4 | | | | | | |
| PT-284 | 49.5 | | | | | | |
| PT-285 | −2.2 | | | | | | |
| PT-286 | 8.8 | | | | | | |
| PT-289 | 3.3 | | | | | | |
| PT-290 | 14.4 | | | | | | |
| PT-291 | 15.2 | | | | | | |
| PT-292 | 18.7 | | | | | | |
| PT-293 | 7.7 | | | | | | |
| PT-294 | 67.2 | 24.4 | | 12.5 | 15.5 | | |
| PT-295 | 7.0 | | | | | | |
| PT-296 | 13.3 | | | | | | |
| PT-297 | 4.9 | | | | | | |
| PT-299 | 6.7 | | | | | | |
| PT-300 | 14.4 | | | | | | |
| PT-301 | 21.6 | | | | | | |
| PT-302 | 50.4 | | | | | | |
| PT-303 | 59.9 | | | 12.0 | 30.5 | | |
| PT-304 | 63.0 | | | | | | |
| PT-306 | 70.4 | 20.1 | 9.0 | 10.0 | 48.5 | | |
| PT-307 | 84.9 | 14.0 | 16.6 | 10.0 | 62.5 | | |
| PT-308 | 53.4 | | | | | | |
| PT-309 | 8.2 | | | | | | |
| PT-310 | 23.6 | | | | | | |
| PT-311 | −7.5 | | | | | | |
| PT-312 | 5.2 | | | | | | |
| PT-314 | 0.3 | | | | | | |
| PT-317 | 10.0 | | | | | | |
| PT-319 | 55.7 | 4.5 | | 10.0 | 41.0 | | |
| PT-320 | 51.0 | 16.7 | 26.5 | | | | |
| PT-321 | 48.3 | | | | | | |
| PT-322 | 78.3 | | | | | | |
| PT-323 | 48.9 | | | | | | |
| PT-325 | 53.8 | 19.9 | 24.3 | 10.0 | 36.0 | | |
| PT-326 | 39.9 | | | | | | |
| PT-327 | 35.3 | 18.5 | 9.4 | | | | |
| PT-328 | 58.1 | | | | | | |
| PT-329 | 54.9 | | | | | | |
| PT-330 | 21.2 | | | | | | |
| PT-331 | 29.6 | | | | | | |

TABLE 15-continued

Assay results

| ID (PT-nnn) | Late INa % blk | Tonic Peak INa % blk | UDB Peak INa % blk | hERG Patch Clamp hERG % blk | hERG Patch Clamp hERG % blk | CaL Plate Assay 1 µM % blk | CaL Plate Assay 10 µM % blk |
|---|---|---|---|---|---|---|---|
| PT-332 | 20.0 | 11.3 | 2.7 | | | | |
| PT-333 | 13.1 | | | | | | |
| PT-334 | 29.9 | | | | | | |
| PT-335 | 58.1 | | | | | | |
| PT-336 | 60.1 | | | | | | |
| PT-337 | 30.2 | | | | | | |
| PT-338 | 56.3 | | | | | | |
| PT-339 | 51.4 | 22.2 | 9.0 | 11.5 | 43.5 | | |
| PT-340 | 71.9 | 89.1 | | 57.0 | 93.5 | | |
| PT-341 | 23.3 | | | | | | |
| PT-342 | 80.1 | | | 10.0 | 47.5 | | |
| PT-343 | 34.4 | | | | | | |
| PT-344 | 44.6 | | | | | | |
| PT-345 | 36.7 | | | | | | |
| PT-346 | 23.0 | | | | | | |
| PT-347 | 5.1 | | | | | | |
| PT-348 | 71.6 | 17.2 | | 10.0 | 38.5 | | |
| PT-349 | 77.3 | | | | | | |
| PT-350 | 63.2 | | | | | | |
| PT-351 | 81.6 | 49.9 | | | | | |
| PT-352 | 76.3 | 17.7 | | | | | |
| PT-353 | 5.8 | | | | | | |
| PT-354 | 64.7 | | | | | | |
| PT-355 | 14.8 | | | | | | |
| PT-356 | 16.4 | | | | | | |
| PT-357 | 19.6 | | | | | | |
| PT-358 | 7.4 | | | | | | |
| PT-359 | 21.3 | | | | | | |
| PT-360 | 7.2 | | | | | | |
| PT-361 | 41.0 | | | | | | |
| PT-362 | 14.4 | | | | | | |
| PT-363 | 40.9 | | | 10.0 | 19.5 | | |
| PT-364 | 25.8 | | | 10.0 | 17.5 | | |
| PT-365 | 26.9 | | | | | | |
| PT-366 | 87.8 | | | 28.0 | 92.0 | | |
| PT-367 | 16.1 | | | | | | |
| PT-368 | −4.2 | | | | | | |
| PT-369 | 47.3 | 26.3 | 13.5 | 10.0 | 25.0 | | |
| PT-370 | 24.7 | | | | | | |
| PT-372 | 20.8 | | | | | | |
| PT-373 | 64.9 | 22.5 | | | | | |
| PT-374 | 66.3 | 38.7 | | | | | |
| PT-375 | 50.7 | | | | | | |
| PT-376 | 61.0 | | | | | | |
| PT-377 | 30.3 | | | | | | |
| PT-378 | 42.0 | | | 10.0 | 41.5 | | |
| PT-379 | 55.0 | 11.1 | 9.8 | | | | |
| PT-380 | 70.9 | | | | | | |
| PT-381 | 43.7 | | | | | | |
| PT-382 | 13.9 | | | | | | |
| PT-383 | 79.5 | | | | | | |
| PT-384 | 29.4 | | | | | | |
| PT-385 | 56.5 | | | | | | |
| PT-386 | 79.2 | | | 10.0 | 16.5 | | |
| PT-387 | 84.8 | | | | | | |
| PT-388 | 2.7 | | | | | | |
| PT-389 | 49.7 | −1.6 | | 23.5 | 69.0 | | |
| PT-390 | 20.0 | | | | | | |
| PT-391 | 32.4 | | | | | | |
| PT-393 | 9.8 | | | | | | |
| PT-394 | 45.2 | 15.4 | 8.0 | | | | |
| PT-395 | 48.7 | | | | | | |
| PT-396 | 80.7 | | | 10.0 | 32.0 | | |
| PT-397 | 69.1 | | | 10.0 | 25.0 | | |
| PT-398 | 18.3 | | | | | | |
| PT-399 | 66.2 | | | | | | |
| PT-400 | 53.2 | | | | | | |
| PT-401 | 77.3 | 25.9 | | | | | |
| PT-402 | 18.3 | | | | | | |
| PT-403 | 9.7 | | | | | | |
| PT-404 | 80.9 | | | | | | |
| PT-405 | 18.4 | | | | | | |
| PT-406 | 20.3 | | | | | | |
| PT-407 | 10.6 | | | | | | |
| PT-408 | 30.4 | | | | | | |
| PT-409 | 43.1 | | | 27.0 | 78.5 | | |
| PT-410 | 11.4 | | | | | | |
| PT-411 | 11.4 | | | | | | |
| PT-412 | 27.6 | | | | | | |
| PT-414 | 78.0 | 21.6 | | | | | |
| PT-415 | 75.4 | | | 10.5 | 38.5 | | |
| PT-416 | 25.6 | | | | | | |
| PT-417 | 41.3 | | | | | | |
| PT-418 | 42.7 | | | | | | |
| PT-419 | 44.2 | | | | | | |
| PT-420 | 75.3 | | | | | | |
| PT-421 | 23.5 | | | | | | |
| PT-422 | 35.2 | | | | | | |
| PT-423 | 67.2 | 18.5 | 20.4 | | | | |
| PT-426 | 81.0 | 60.1 | 50.7 | | | | |
| PT-428 | 45.1 | 5.3 | 1.0 | | | | |
| PT-429 | 14.9 | | | | | | |
| PT-430 | 95.3 | 91.0 | 55.6 | 10.0 | 21.5 | | |
| PT-431 | 56.1 | | | | | | |
| PT-432 | 56.9 | | | | | | |
| PT-433 | 30.3 | | | | | | |
| PT-434 | 10.5 | | | | | | |
| PT-435 | 19.4 | | | | | | |
| PT-436 | 18.7 | | | | | | |
| PT-437 | 43.1 | | | | | | |
| PT-438 | 20.9 | | | | | | |
| PT-439 | 56.1 | | | | | | |
| PT-440 | 42.8 | | | 12.0 | 48.0 | | |
| PT-443 | 20.0 | | | | | | |
| PT-444 | 9.1 | | | | | | |
| PT-445 | 62.2 | 49.6 | 31.6 | 10.5 | 50.0 | | |
| PT-446 | 7.0 | | | | | | |
| PT-447 | 77.4 | | | | | | |
| PT-448 | 33.6 | | | 10.0 | 57.5 | | |
| PT-449 | 47.6 | | | | | | |
| PT-450 | 7.3 | | | | | | |
| PT-451 | 18.4 | | | | | | |
| PT-452 | 5.9 | | | | | | |
| PT-454 | 30.2 | | | | | | |
| PT-455 | 9.0 | | | | | | |
| PT-456 | 2.7 | | | | | | |
| PT-457 | 12.6 | | | 10.0 | 21.0 | | |
| PT-458 | 19.0 | | | | | | |
| PT-459 | 10.3 | | | | | | |
| PT-460 | 22.1 | | | | | | |
| PT-461 | 6.2 | | | | | | |
| PT-462 | 63.0 | | | | | | |
| PT-463 | 42.3 | | | | | | |
| PT-464 | 55.8 | 2.7 | | 11.0 | 55.0 | | |
| PT-465 | 10.5 | | | | | | |
| PT-467 | 4.3 | | | | | | |
| PT-470 | 26.0 | | | | | | |
| PT-471 | 30.0 | | | | | | |
| PT-472 | 22.6 | | | | | | |
| PT-473 | 9.4 | | | | | | |
| PT-474 | 22.0 | | | | | | |
| PT-475 | 5.5 | | | | | | |
| PT-476 | 2.6 | | | 17.5 | 23.0 | | |
| PT-477 | 6.2 | | | 12.0 | 44.0 | | |
| PT-478 | 34.3 | | | | | | |
| PT-479 | 35.7 | | | | | | |
| PT-480 | 5.4 | | | | | | |
| PT-481 | 18.0 | | | | | | |
| PT-482 | 3.2 | | | | | | |
| PT-483 | 31.8 | | | | | | |
| PT-484 | 36.1 | | | | | | |
| PT-485 | 5.2 | | | | | | |
| PT-486 | 30.8 | | | | | | |
| PT-487 | 20.9 | | | | | | |

TABLE 15-continued

Assay results

| ID (PT-nnn) | Late INa % blk | Tonic Peak INa % blk | UDB Peak INa % blk | hERG Patch Clamp hERG % blk | hERG % blk | CaL Plate Assay 1 μM % blk | 10 μM % blk |
|---|---|---|---|---|---|---|---|
| PT-488 | 82.3 | | | | | | |
| PT-489 | 80.7 | 46.2 | 29.2 | | | | |
| PT-490 | 7.3 | | | | | | |
| PT-491 | −0.9 | | | | | | |
| PT-492 | 39.3 | 0.3 | | | | | |
| PT-493 | 0.5 | | | 10.0 | 10.0 | | |
| PT-494 | 71.8 | 6.7 | 2.0 | | | | |
| PT-495 | 54.2 | 20.7 | 11.6 | | | | |
| PT-496 | 84.2 | 36.8 | 9.1 | | | | |
| PT-497 | 59.0 | 22.2 | 15.4 | | | | |
| PT-498 | 25.2 | | | | | | |
| PT-499 | 27.7 | | | | | | |
| PT-500 | 2.7 | | | | | | |
| PT-501 | 2.5 | | | | | | |
| PT-502 | 27.0 | | | | | | |
| PT-503 | 29.2 | | | | | | |
| PT-504 | 28.2 | | | | | | |
| PT-505 | 69.6 | | | | | | |
| PT-506 | 81.4 | 48.8 | 23.0 | | | | |
| PT-507 | 0.2 | | | | | | |
| PT-508 | 11.6 | | | | | | |
| PT-509 | 6.4 | | | | | | |
| PT-510 | 19.9 | | | | | | |
| PT-511 | 19.5 | | | | | | |
| PT-512 | 26.6 | | | 10.5 | 14.0 | | |
| PT-513 | 10.5 | | | | | | |
| PT-515 | 10.8 | | | | | | |
| PT-516 | 20.2 | | | | | | |
| PT-517 | 43.3 | | | | | | |
| PT-518 | 71.2 | 24.0 | | | | | |
| PT-519 | 27.3 | | | | | | |
| PT-520 | 78.4 | | | | | | |
| PT-521 | 37.5 | | | | | | |
| PT-522 | 37.7 | | | | | | |
| PT-523 | 66.7 | 20.8 | 16.2 | | | | |
| PT-524 | 61.1 | | | | | | |
| PT-525 | 67.5 | | | | | | |

L-type Calcium Channel Patch Clamp Screening Assay:

Compounds are screened to test for block of human cardiac L-type calcium channels (hCav1.2, encoded by the human CACNA1C gene and coexpressed with the beta 2 subunit, encoded by the human CACNB2 gene) expressed in an HEK293 cell line. Stable transfectants were selected using antibiotic resistance genes incorporated into the expression plasmids and selection pressure is maintained with selection antibiotics added to the culture medium. Cells are cultured using standard tissue culture methods for HEK293 cells.

Cells are harvested for addition to a PatchXpress automated patch clamp system. The external solution contains: 137 mM NaCl; 4 mM KCl; 1.8 mM $CaCl_2$; 1 mM $MgCl_2$; 10 mM HEPES; 10 mM Glucose (pH adjusted to 7.4 with NaOH). The internal solution contains: 130 mM Cs Aspartate; 5 mM $MgCl_2$; 5 mM EGTA; 4 mM ATP; 0.1 mM GTP; 10 mM HEPES (pH adjusted to 7.2 with N-methyl-D-glutamine).

Figure 5:
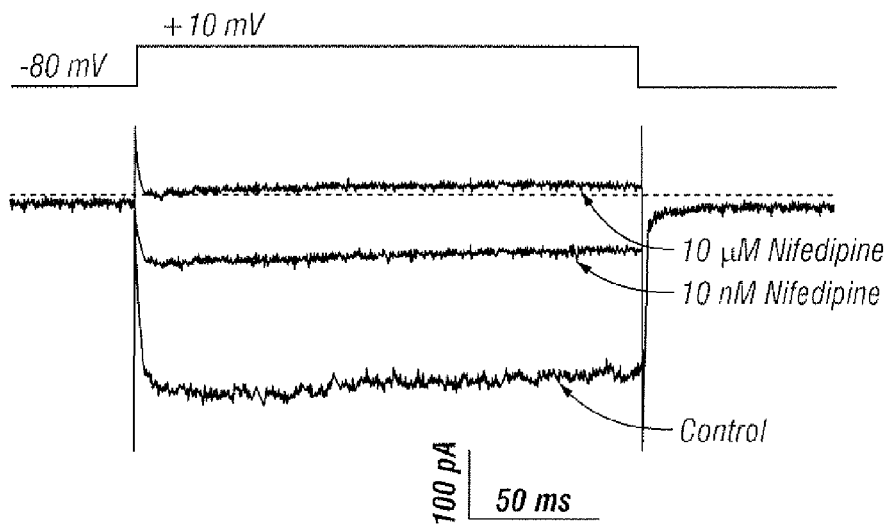
FIG. 5 shows typical L-type calcium channel current traces in response to a depolarizing stimulus before and after application of a calcium channel blocker (10 nM and 10 μM nifedipine).

Onset of block and steady state block of hCav1.2 channels are monitored using a stimulus voltage pattern consisting of a depolarizing test pulse (duration, 200 ms; amplitude, 10 mV) at 10 s intervals from a −80 mV holding potential (FIG. 5). Test compound concentrations (1 μM and 10 μM) are applied cumulatively in ascending order without washout between applications. Peak current is measured during the step to 10 mV. A saturating concentration of nifedipine (10 μM) is added at the end of each experiment to completely block hCav1.2 current and verify sensitivity to channel blockade. Leakage current is measured after nifedipine addition and digitally subtracted from the total membrane current record. Each compound is applied to naïve cells and each concentration is applied four times for a total exposure duration of five (5) minutes per concentration.

Test compound stock solutions are prepared in dimethyl sulfoxide (DMSO) and stored frozen. Test compound concentrations are prepared fresh daily by diluting stock solutions into the external HEPES-buffered physiological saline solution described above. Previous results have shown that =0.3% DMSO does not affect channel current, so all test formulations contain 0.3% DMSO. Each test compound formulation is sonicated (Model 2510/5510, Branson Ultrasonics, Danbury, Conn.), at ambient room temperature for at least 20 minutes to facilitate dissolution. In preparation for the recording session, a glass-lined 96-well compound plate is loaded with the appropriate amounts of test and control solutions, and placed in the plate well of PatchXpress® (Model 7000A, MDS Analytical Technologies, Sunnyvale, Calif.).

Data acquisition and analyses are performed using conventional software. Steady state is defined by the limiting constant rate of change with time (linear time dependence). The steady state before and after test compound application is used to calculate the percentage of current inhibited at each concentration. Results are shown in Table 16.

TABLE 16

Results from L-type Calcium Channel Patch Clamp Screening Assay:

| | $ICa_L$ Patch Clamp Assay | |
|---|---|---|
| ID (PT-nnn) | 1 μM % blk | 10 μM % blk |
| PT-437 | −0.1 | 13.2 |
| PT-409 | 2.7 | 19.9 |
| PT-431 | 3.7 | 2.4 |
| PT-432 | 3.7 | 35.3 |
| PT-430 | 91.8 | 98.6 |

The assay results shown in Table 15 and Table 16 establish that compounds tested showed activity as modulators of late sodium current, for example by inhibiting (or reducing) the late sodium current. In some embodiments, compounds tested potentiated late sodium current (see PT-163, PT-165, and PT-166); such compounds may be useful in stimulating late sodium current in test assays, such as the use of Tefluthrin or sea anemone toxin as described above.

It is generally desirable that the effects of a compound be specific for the late sodium current and show little or no activity with respect to one or more other ion channels. Thus, in some embodiments, a compound having an activity of reducing late sodium current will also exhibit little or no activity with regard to the peak sodium current. In particular embodiments, a compound having an activity of reducing late sodium current will also exhibit little or no activity with regard to the hERG potassium channel. In some embodiments, a compound having an activity of reducing late sodium current will also exhibit little or no activity with regard to the L-type calcium channel. For example, a given compound may provide a 30% (or greater, e.g. more than 40%, more than 50%, more than 60%, more than 70%, more than 80%) reduction in late sodium current in the assay described herein, and the same compound may exhibit little or no activity for one or more of the peak sodium current, the hERG potassium channel, and the L-type calcium channel. In this regard, a compound having "little" effect will typically show less then a 30% reduction (e.g. less than a 20% reduction, less than a 15% reduction, less than a 10% reduction) in the given activity (e.g. Peak INa, hERG, L-type calcium), when measured using the assay described herein. In this regard, "no" effect means that any activity measured will differ from the control by less than the standard error of the measurement. The assays conducted to measure activities in this regard should be performed as described above, with the compound at a concentration of 10 µM (or at the upper limit of solubility, if less).

In particular embodiments, a compound will exhibit a high selectivity for the late sodium current modulatory activity as compared to the activity in one or more other ion channels. The selectivity of a compound may be determined by determining the percentage reduction in late sodium current due to the compound, as measured by the assay described above. The percentage reduction in one other ion channel activity, such as the hERG potassium channel or L-type calcium channel, due to the compound is determined as described above. The selectivity is determined by taking the ratio of (percentage reduction in late sodium current) to (percentage reduction in one other ion channel activity). The assays conducted to measure activities in this regard should be performed as described above, with the compound at a concentration of 10 M (or at the upper limit of solubility, if less). In particular embodiments, the selectivity of a compound of the invention will be at least 5:1, e.g. at least 6:1, at least 7:1, at least 8:1, at least 9:1, at least 10:1, at least 12:1, at least 15:1, at least 20:1, or at least 25:1, when comparing the percentage reduction in late sodium current versus percentage reduction of one of the peak sodium current, the hERG potassium channel current, or the L-type calcium channel.

What is claimed is:

1. A compound selected from the group consisting of:
   diethyl 2,6-dimethyl-4-(naphthalen-2-yl)-1,4-dihydropyridine-3,5-dicarboxylate,
   diethyl 2,6-dimethyl-4-(naphthalen-1-yl)-1,4-dihydropyridine-3,5-dicarboxylate,
   diethyl 4-(2,3-dihydrobenzo[b][1,4]dioxin-6-yl)-2,6-dimethyl-1,4-dihydropyridine-3,5-dicarboxylate,
   diethyl 2,6-dimethyl-4-(thiophen-3-yl)-1,4-dihydropyridine-3,5-dicarboxylate,
   diethyl 2,6-dimethyl-4-(thiophen-2-yl)-1,4-dihydropyridine-3,5-dicarboxylate,
   5-(3,5-bis(ethoxycarbonyl)-2,6-dimethyl-1,4-dihydropyridin-4-yl)thiophene-2-carboxylic acid,
   diethyl 4-(5-ethylthiophen-2-yl)-2,6-dimethyl-1,4-dihydropyridine-3,5-dicarboxylate,
   diethyl 4-(benzo[b]thiophen-2-yl)-2,6-dimethyl-1,4-dihydropyridine-3,5-dicarboxylate,
   diethyl 4-(benzo[b]thiophen-3-yl)-2,6-dimethyl-1,4-dihydropyridine-3,5-dicarboxylate,
   diethyl 2,6-dimethyl-4-(3-methylbenzo[b]thiophen-2-yl)-1,4-dihydropyridine-3,5-dicarboxylate,
   diethyl 2,6-dimethyl-4-(3-methylbenzo[b]thiophen-2-yl)pyridine-3,5-dicarboxylate,
   diethyl 4-(5-(4-chlorophenyl)furan-2-yl)-2,6-dimethyl-1,4-dihydropyridine-3,5-dicarboxylate,
   diethyl 2,6-dimethyl-4-(5-(2-(trifluoromethyl)phenyl)furan-2-yl)-1,4-dihydropyridine-3,5-dicarboxylate,
   diethyl 4-(furan-3-yl)-2,6-dimethyl-1,4-dihydropyridine-3,5-dicarboxylate,
   diethyl 4-(5-ethylfuran-2-yl)-2,6-dimethyl-1,4-dihydropyridine-3,5-dicarboxylate,
   diethyl 4-(benzofuran-2-yl)-2,6-dimethyl-1,4-dihydropyridine-3,5-dicarboxylate,
   diisopropyl 2,6-dimethyl-4-(naphthalen-1-yl)-1,4-dihydropyridine-3,5-dicarboxylate,
   diisopropyl 4-(5-bromothiophen-2-yl)-2,6-dimethyl-1,4-dihydropyridine-3,5-dicarboxylate,
   bis(2-methoxyethyl) 4-(3-bromothiophen-2-yl)-2,6-dimethyl-1,4-dihydropyridine-3,5-dicarboxylate,
   diisopropyl 4-(5-(4-chlorophenyl)furan-2-yl)-2,6-dimethyl-1,4-dihydropyridine-3,5-dicarboxylate,
   diisopropyl 4-(1-(4-fluorophenyl)-5-methyl-1H-pyrazol-4-yl)-2,6-dimethyl-1,4-dihydropyridine-3,5-dicarboxylate,
   diisopropyl 4-(3-(4-fluorophenyl)-1H-pyrazol-4-yl)-2,6-dimethyl-1,4-dihydropyridine-3,5-dicarboxylate,
   dibenzyl 2,6-dimethyl-4-(naphthalen-2-yl)-1,4-dihydropyridine-3,5-dicarboxylate,
   bis(3,4-dimethoxybenzyl) 2,6-dimethyl-4-(naphthalen-2-yl)-1,4-dihydropyridine-3,5-dicarboxylate,
   diethyl 4-(5-bromothiophen-2-yl)-2,6-diethyl-1,4-dihydropyridine-3,5-dicarboxylate,
   diethyl 4-(5-bromothiophen-2-yl)-2,6-dipropyl-1,4-dihydropyridine-3,5-dicarboxylate,
   diethyl 4-(5-bromothiophen-2-yl)-2,6-diisopropyl-1,4-dihydropyridine-3,5-dicarboxylate,
   diethyl 1,2,6-trimethyl-4-(naphthalen-1-yl)-1,4-dihydropyridine-3,5-dicarboxylate,
   diethyl 4-(2,4-dimethoxyphenyl)-2,6-dimethyl-1,4-dihydropyridine-3,5-dicarboxylate,
   diethyl 4-(2-bromophenyl)-2,6-dimethyl-1,4-dihydropyridine-3,5-dicarboxylate,
   diethyl 4-(2-cyano-4-methoxyphenyl)-2,6-dimethyl-1,4-dihydropyridine-3,5-dicarboxylate,
   diethyl 4-(2-fluoro-4-methoxyphenyl)-2,6-dimethyl-1,4-dihydropyridine-3,5-dicarboxylate,
   diethyl 4-(2-methoxy-4-nitrophenyl)-2,6-dimethyl-1,4-dihydropyridine-3,5-dicarboxylate,
   diethyl 4-(2-methoxyphenyl)-2,6-dimethyl-1,4-dihydropyridine-3,5-dicarboxylate,
   diethyl 4-(4-(dimethylamino)-2-methoxyphenyl)-2,6-dimethyl-1,4-dihydropyridine-3,5-dicarboxylate,
   diethyl 4-(4-(dimethylamino)-2-nitrophenyl)-2,6-dimethyl-1,4-dihydropyridine-3,5-dicarboxylate,
   diethyl 4-(biphenyl-2-yl)-2,6-dimethyl-1,4-dihydropyridine-3,5-dicarboxylate, and
   diethyl 4-(biphenyl-3-yl)-2,6-dimethyl-1,4-dihydropyridine-3,5-dicarboxylate, or a pharmaceutically acceptable salt thereof.

2. A compound selected from the group consisting of:
   diethyl 2,6-dimethyl-4-(naphthalen-2-yl)-1,4-dihydropyridine-3,5-dicarboxylate,
   diethyl 2,6-dimethyl-4-(naphthalen-1-yl)-1,4-dihydropyridine-3,5-dicarboxylate,
   diethyl 4-(2,3-dihydrobenzo[b][1,4]dioxin-6-yl)-2,6-dimethyl-1,4-dihydropyridine-3,5-dicarboxylate,
   diethyl 2,6-dimethyl-4-(thiophen-3-yl)-1,4-dihydropyridine-3,5-dicarboxylate,
   diethyl 2,6-dimethyl-4-(thiophen-2-yl)-1,4-dihydropyridine-3,5-dicarboxylate,
   5-(3,5-bis(ethoxycarbonyl)-2,6-dimethyl-1,4-dihydropyridin-4-yl)thiophene-2-carboxylic acid,
   diethyl 4-(5-ethylthiophen-2-yl)-2,6-dimethyl-1,4-dihydropyridine-3,5-dicarboxylate,
   diethyl 4-(benzo[b]thiophen-2-yl)-2,6-dimethyl-1,4-dihydropyridine-3,5-dicarboxylate,
   diethyl 4-(benzo[b]thiophen-3-yl)-2,6-dimethyl-1,4-dihydropyridine-3,5-dicarboxylate,
   diethyl 2,6-dimethyl-4-(3-methylbenzo[b]thiophen-2-yl)-1,4-dihydropyridine-3,5-dicarboxylate,
   diethyl 2,6-dimethyl-4-(3-methylbenzo[b]thiophen-2-yl)pyridine-3,5-dicarboxylate, diethyl 4-(5-(4-chlorophenyl)furan-2-yl)-2,6-dimethyl-1,4-dihydropyridine-3,5-dicarboxylate,
diethyl 2,6-dimethyl-4-(5-(2-(trifluoromethyl)phenyl)furan-2-yl)-1,4-dihydropyridine-3,5-dicarboxylate,
diethyl 4-(furan-3-yl)-2,6-dimethyl-1,4-dihydropyridine-3,5-dicarboxylate,
diethyl 4-(5-ethylfuran-2-yl)-2,6-dimethyl-1,4-dihydropyridine-3,5-dicarboxylate,
diethyl 4-(benzofuran-2-yl)-2,6-dimethyl-1,4-dihydropyridine-3,5-dicarboxylate,
diisopropyl 2,6-dimethyl-4-(naphthalen-1-yl)-1,4-dihydropyridine-3,5-dicarboxylate,
diisopropyl 4-(5-bromothiophen-2-yl)-2,6-dimethyl-1,4-dihydropyridine-3,5-dicarboxylate,
bis(2-methoxyethyl) 4-(3-bromothiophen-2-yl)-2,6-dimethyl-1,4-dihydropyridine-3,5-dicarboxylate,
diisopropyl 4-(5-(4-chlorophenyl)furan-2-yl)-2,6-dimethyl-1,4-dihydropyridine-3,5-dicarboxylate,
diisopropyl 4-(1-(4-fluorophenyl)-5-methyl-1H-pyrazol-4-yl)-2,6-dimethyl-1,4-dihydropyridine-3,5-dicarboxylate,
diisopropyl 4-(3-(4-fluorophenyl)-1H-pyrazol-4-yl)-2,6-dimethyl-1,4-dihydropyridine-3,5-dicarboxylate,
dibenzyl 2,6-dimethyl-4-(naphthalen-2-yl)-1,4-dihydropyridine-3,5-dicarboxylate,
bis(3,4-dimethoxybenzyl) 2,6-dimethyl-4-(naphthalen-2-yl)-1,4-dihydropyridine-3,5-dicarboxylate,
diethyl 4-(5-bromothiophen-2-yl)-2,6-diethyl-1,4-dihydropyridine-3,5-dicarboxylate,
diethyl 4-(5-bromothiophen-2-yl)-2,6-dipropyl-1,4-dihydropyridine-3,5-dicarboxylate,
diethyl 4-(5-bromothiophen-2-yl)-2,6-diisopropyl-1,4-dihydropyridine-3,5-dicarboxylate,
diethyl 1,2,6-trimethyl-4-(naphthalen-1-yl)-1,4-dihydropyridine-3,5-dicarboxylate,
diethyl 4-(2,4-dimethoxyphenyl)-2,6-dimethyl-1,4-dihydropyridine-3,5-dicarboxylate,
diethyl 4-(2-bromophenyl)-2,6-dimethyl-1,4-dihydropyridine-3,5-dicarboxylate,
diethyl 4-(2-cyano-4-methoxyphenyl)-2,6-dimethyl-1,4-dihydropyridine-3,5-dicarboxylate,
diethyl 4-(2-fluoro-4-methoxyphenyl)-2,6-dimethyl-1,4-dihydropyridine-3,5-dicarboxylate,
diethyl 4-(2-methoxy-4-nitrophenyl)-2,6-dimethyl-1,4-dihydropyridine-3,5-dicarboxylate,
diethyl 4-(2-methoxyphenyl)-2,6-dimethyl-1,4-dihydropyridine-3,5-dicarboxylate,
diethyl 4-(4-(dimethylamino)-2-methoxyphenyl)-2,6-dimethyl-1,4-dihydropyridine-3,5-dicarboxylate,
diethyl 4-(4-(dimethylamino)-2-nitrophenyl)-2,6-dimethyl-1,4-dihydropyridine-3,5-dicarboxylate,
diethyl 4-(biphenyl-2-yl)-2,6-dimethyl-1,4-dihydropyridine-3,5-dicarboxylate, and
diethyl 4-(biphenyl-3-yl)-2,6-dimethyl-1,4-dihydropyridine-3,5-dicarboxylate, or a pharmaceutically acceptable salt thereof.

3. A pharmaceutical formulation comprising a compound according to claim 1 or a pharmaceutically acceptable salt or tautomeric form thereof, and at least one pharmaceutically acceptable excipient.

4. A pharmaceutical formulation comprising a compound according to claim 2 or a pharmaceutically acceptable salt or tautomeric form thereof, and at least one pharmaceutically acceptable excipient.

* * * * *